United States Patent
Nys et al.

(10) Patent No.: US 12,049,506 B2
(45) Date of Patent: Jul. 30, 2024

(54) THERAPEUTIC BINDING MOLECULES

(71) Applicant: MedImmune Limited, Cambridge (GB)

(72) Inventors: Josquin Nys, Cambridge (GB); Albert Thom, Cambridge (GB); Peter Cariuk, Cambridge (GB); Darren Schofield, Cambridge (GB); Aidan Riley, Cambridge (GB); Catherine Huntington, Cambridge (GB); David Rees, Cambridge (GB); Lorraine Irving, Cambridge (GB); Matthew Robinson, Cambridge (GB)

( * ) Notice: Subject to any disclaimer, the term of this patent is extended or adjusted under 35 U.S.C. 154(b) by 0 days.

(21) Appl. No.: 17/697,041

(22) Filed: Mar. 17, 2022

(65) Prior Publication Data

US 2022/0306754 A1    Sep. 29, 2022

Related U.S. Application Data

(60) Provisional application No. 63/162,603, filed on Mar. 18, 2021.

(51) Int. Cl.
    *C07K 16/28*   (2006.01)
    *A61P 1/00*    (2006.01)

(52) U.S. Cl.
    CPC .......... *C07K 16/2866* (2013.01); *A61P 1/00* (2018.01); *C07K 2317/24* (2013.01); *C07K 2317/33* (2013.01); *C07K 2317/41* (2013.01); *C07K 2317/52* (2013.01); *C07K 2317/565* (2013.01); *C07K 2317/72* (2013.01); *C07K 2317/732* (2013.01); *C07K 2317/77* (2013.01); *C07K 2317/92* (2013.01)

(58) Field of Classification Search
    CPC .......... C07K 16/2866; C07K 2317/24; C07K 2317/33; C07K 2317/41; C07K 2317/52; C07K 2317/565; C07K 2317/72; C07K 2317/732; C07K 2317/77; C07K 2317/92; A61P 1/00
    See application file for complete search history.

(56) References Cited

U.S. PATENT DOCUMENTS

2017/0355756 A1* 12/2017 Julien .................... C07K 16/18

FOREIGN PATENT DOCUMENTS

WO    WO-2008068048 A2 *   6/2008   ............. A61P 31/10
WO    2015/075269 A1        5/2015

OTHER PUBLICATIONS

Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*

Kussie PH, Parhami-Seren B, Wysocki LJ, Margolies Mn. J Immunol. Jan. 1, 1994;152(1):146-52. PMID: 8254187. (Year: 1994).*

(Continued)

*Primary Examiner* — Aurora M Fontainhas
*Assistant Examiner* — Selam Berhane

(57) ABSTRACT

The invention relates to binding molecules, such as antibodies, that bind to the chemokine receptor CCR9. More particularly, the invention relates to the treatment of CCR9-mediated diseases or conditions such as inflammatory bowel disease (IBD), and methods for the detection of CCR9, which make use of the binding molecules of the invention.

13 Claims, 21 Drawing Sheets

Figure 1A:
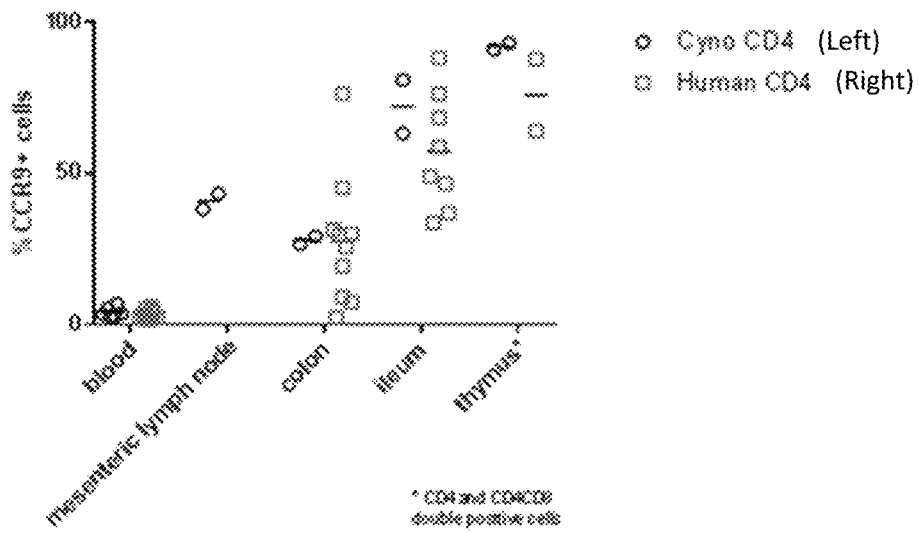

Specification includes a Sequence Listing.

(56) References Cited

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Somovilla-Crespo, B., et al., "92R Monoclonal Antibody Inhibits Human CCR9+ Leukemia Cells Growth in NSG Mice Xenografts," Frontiers In Immunology, 2018, vol. 9, article 77, pp. 1-12.

* cited by examiner

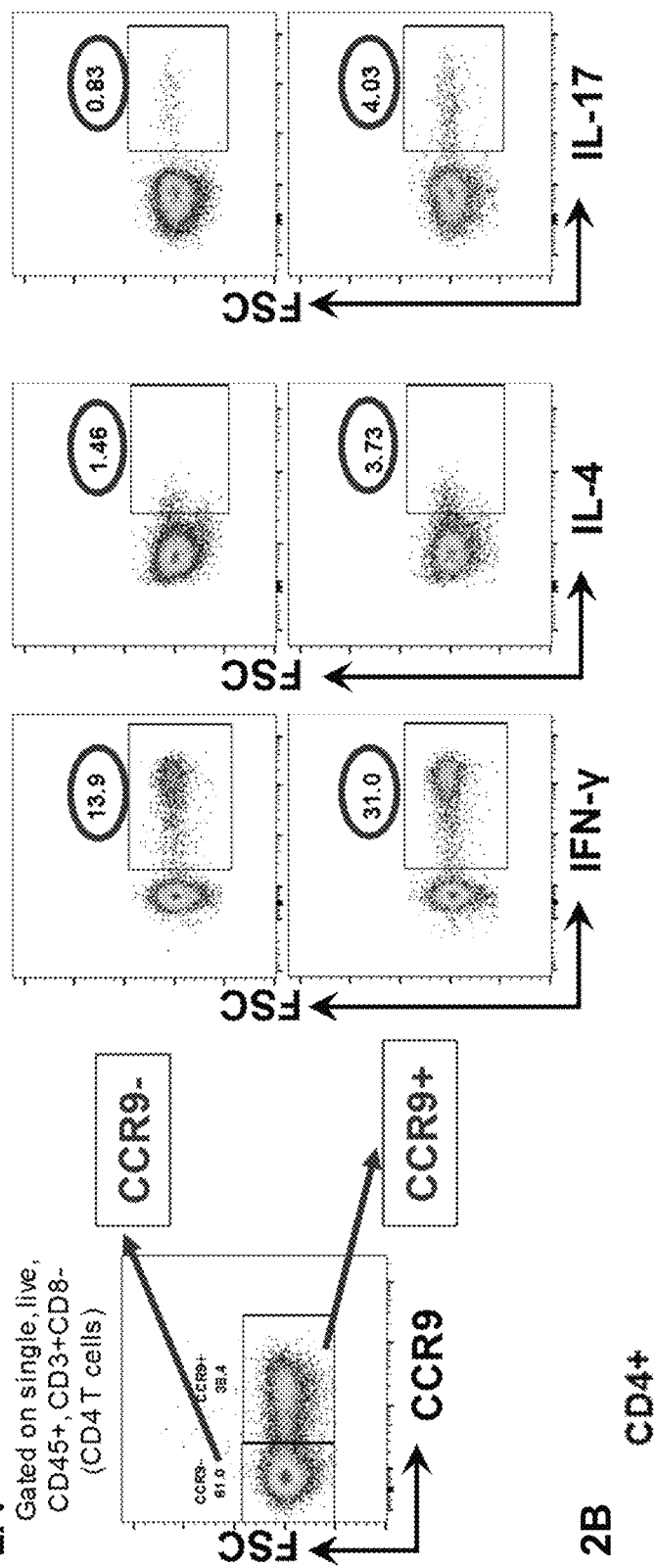
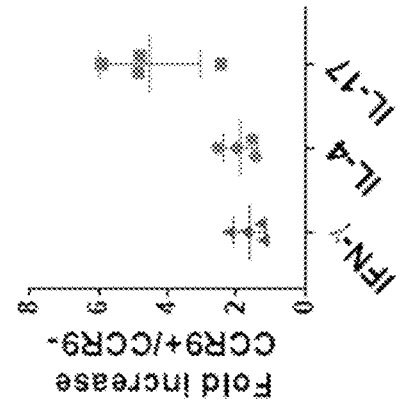
Figure 2A
Figure 2B

Figure 3A

```
                              FW1                                        HCDR1                    FW2                      HCDR2
AB1020011 (SEQ ID NO: 58)  EVQLVESGGGLVKPGGSRKLSCAASGFTFRDYGMH----WVRQAPERGLEWVAYINS-------GSSAIYYADTVKG
AB1020227 (SEQ ID NO: 62)  EVQLVESGGRLVQPKGSLKLSCAASGFTFNTYAMY----WIRQAPGKGLEWVARIRSKS-----NNYATYYADSVKD
AB1020229 (SEQ ID NO: 60)  EVQLVESGGGLVQPKGSLKLSCAASGFTFNTYAMY----WVRQTPEKRLEWVATISD------SNFATYYADSVKD
AB1020234 (SEQ ID NO: 64)  EVQLVESGGGLVKPGGSLKLSCAASGYTFTSYAMS----WVRQTPEKRLEWVATISD------GSSTYYPDNVKG
AB1020243 (SEQ ID NO: 56)  EVQLQQSGTVLARPGASVKMSCKASGYTFTSYWMH----WVKQRPGQGLEWIGVIYP------GNSDTRNQKFKG
AB1020264 (SEQ ID NO: 66)  QVQLQPGAELVKFGASVKISCKASGYTFTSYWMH----WVKQRPGRGLEWIGSIDP------NSGGTKNEKFKS
AB1020283 (SEQ ID NO: 68)  EVKLEESGGGLIVQPGGSMKLSCVASGFSNYWMN----WVRQSPEKGLEWVAQIRLKS----DNGTKNEKFKG
AB1020310 (SEQ ID NO: 70)  EVQLQQSGFELVKFGASVKMSCKASGYTFTSYVMH----WVKQKPGQGLEWIGYINP------YNDGTKNEKFKG
AB1020105 (SEQ ID NO: 72)  EVKLEESGGGLIVQPGGSMKLSCVASGFTFTMKIWMN---WVRQSPENGLEWVQIKLKS----DNYATHYAESVKG
AB1020069 (SEQ ID NO: 74)  EVKLEESGGGLVQPGGSMKLSCVASGFTFSNYWMN-----WVRQSPEKGLEWVAQIRLKS----DNYATHYAESVKG

FW3                                       HCDR3                                   FW4
AB1020011 (SEQ ID NO: 59)  RFTISRDNTKNTLFLQMTSL--RSEDTAMYYCARAGT---------------------------AYWGQGTLVTVSA
AB1020227 (SEQ ID NO: 63)  RFTISRDDSQSMLYLQMNNL--KTEDTAMYYCVRGGGF--------------------------DYWGQGTTLTVSS
AB1020229 (SEQ ID NO: 61)  RFTISRDDSQSMLYLQMNNL--KTEDTAMYYCVRGGS---------------------------DYWGQGTTLTVSS
AB1020234 (SEQ ID NO: 65)  RFTISRDNAKNNLYLQMSHL--KSEDTAMYYCARDPRYF-------------------------DYWGQGTSVTVSS
AB1020243 (SEQ ID NO: 57)  KARLTAVTSATTAYMELSSL--TNEDSAVYYCTRDYIGNYVYYAM-------------------DYWGQGTTLTVSS
AB1020264 (SEQ ID NO: 67)  KATLTVDKPSSTATMQLSSL--TSEDSAVYYCARGGLVYYF-----------------------DYWGQGTTLTVSS
AB1020283 (SEQ ID NO: 69)  RFTISREDSKSSVYLQMNNL--RAEDTGIYYCTRPF----------------------------DYWGQGTTLTVSS
AB1020310 (SEQ ID NO: 71)  KAFLTSDKSSSTAYMELSSL--TSEDSAVYYCARNGGRGRGYAM--------------------SYWGQGTSVTVSS
AB1020105 (SEQ ID NO: 73)  RFAISRDDSKSSVYLQMNNL--RAEDTGIYYCTLRPF---------------------------TYWGQGTLVTVSA
AB1020069 (SEQ ID NO: 75)  RFTISEDDSKSSVYLQMNNL--RAEDTGIYYCTRPF----------------------------AYWGQGTLVTVSS
```

Figure 3B

|  |  | FW1 | LCDR1 | FW2 | LCDR2 |
|---|---|---|---|---|---|
| AB1020011 | (SEQ ID NO: 59) | DVVMTQTPLTLSVTIGQPASISCKSSQSLLDS | ---DGKTYLNWLLQRPGQSPKRLIYQV | ----SRLDS |
| AB1020227 | (SEQ ID NO: 63) | DVVMTQTPLSLSVTIGQPASISCKSSQSLLYS | ---DGKTYLNWLQQRPGQSPKRLMYQV | ----SKLDP |
| AB1020229 | (SEQ ID NO: 61) | DVVMTQTFLSLPVSLGDQASISCRSSQSLVHS | ---DGKTYLNWLQQRPGQSPKRLMYQV | ----SKLDP |
| AB1020234 | (SEQ ID NO: 65) | DVVMTQTFLSLPVSLGDQASISCRSSQSLVHS | ---NGNTYLHWYLQKPGQSPKLLIYKV | ----SNRFS |
| AB1020243 | (SEQ ID NO: 57) | DVVMTQTFLSLPVSLGDQASISCRSSQSLVHS | ---NGNTYLYWYLQKPGQSPKLLIYPV | ----SNRFS |
| AB1020264 | (SEQ ID NO: 67) | DVVMTQTFLSLPVSLGDQASISCRSSQSIVHS | ---NGNTYLEWYLQKPGQSPKLLIYKV | ----SNRFS |
| AB1020283 | (SEQ ID NO: 69) | DVLMTQTFLSLPVSLGDQASISCRSSQSIVHS | ---NGNTYLEWYLQKPGQSPKLLIYKV | ----SNRFS |
| AB1020310 | (SEQ ID NO: 71) | DVLMTQTNPLSLPVSLGDQASISCRSSQSIIHS | ---NGNTYLEWYLQKPGQSPKLLIYKV | ----SNRFS |
| AB1020105 | (SEQ ID NO: 73) | DVLMTQTFLSLPVSLGDQASISCRSSQSIVHS | ---NGNTYLEWYLQKPGQSPKLLIYKV | ----SNRFS |
| AB1020069 | (SEQ ID NO: 75) | DVLMTQTFLSLPVSLGDQASISCRSSQSIVHS | ---NGNTYLEWYLQKPGQSPKLLIYKV | ----SKRLS |

|  |  | FW3 | LCDR3 | FW4 |
|---|---|---|---|---|
| AB1020011 | (SEQ ID NO: 59) | GVPDRFTGSGSGS---TDFTLETIRVEAEDLGVYYC | WQSHFP------ | RTFGGGTKLEI---K |
| AB1020227 | (SEQ ID NO: 63) | GIPDRFSGSGSE---TDFTLKISRVEAEDLGVYYC | LQGTYP------ | ETFGTGTKLEI---K |
| AB1020229 | (SEQ ID NO: 61) | GIPDRFSGSGSGE---TDFTLKISRVEAEDLGVYYC | LQGTYYP----- | YTFGSGTKLEI---K |
| AB1020234 | (SEQ ID NO: 65) | GVPDRFSGSGSGS---TDFTLKISRVEAEDLGVYFC | SQSTHVP----- | WTFGGGTKLEI---K |
| AB1020243 | (SEQ ID NO: 57) | GVPDRFSGSGSGS---TDFTLKISRVEAEDLGVYFC | SQSTHVP----- | WTFGGGTKLEI---K |
| AB1020264 | (SEQ ID NO: 67) | GVPDRFSGSGSGS---TDFTLKISRVEAEDLGVYYC | FQGTHVP----- | HTFGSGTKLEI---K |
| AB1020283 | (SEQ ID NO: 69) | GVPDRFSGSGSGS---TDFTLKISRVEAEDLGVYYC | FQGSHVP----- | LIFGSGTKLEI---K |
| AB1020310 | (SEQ ID NO: 71) | GVPDRFSGSGSGS---TDFTLKISRVEAEDLGVYYC | FQGSHVP----- | PTFGGGTKLEI---K |
| AB1020105 | (SEQ ID NO: 73) | GVPDRFSGSGSGS---TDFTLKISRVEAEDLGVYYC | FQGSHVP----- | WTFGGGTKLEI---K |
| AB1020069 | (SEQ ID NO: 75) | GVPDRFSGSGSGS---TEFTLKISRVEAEDLGVYYC | FQGSHVP----- | LIFGAGTKLEI---K |

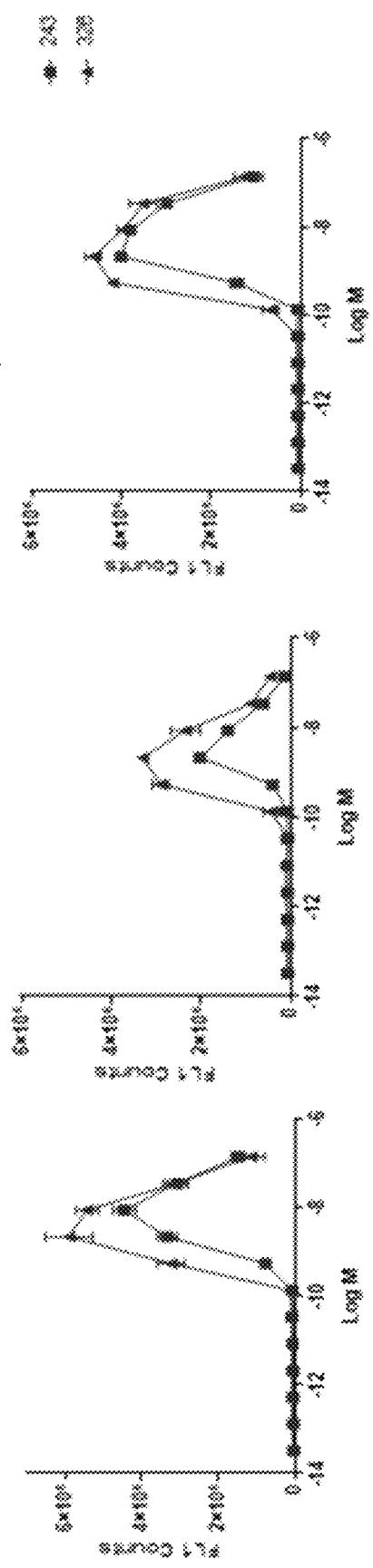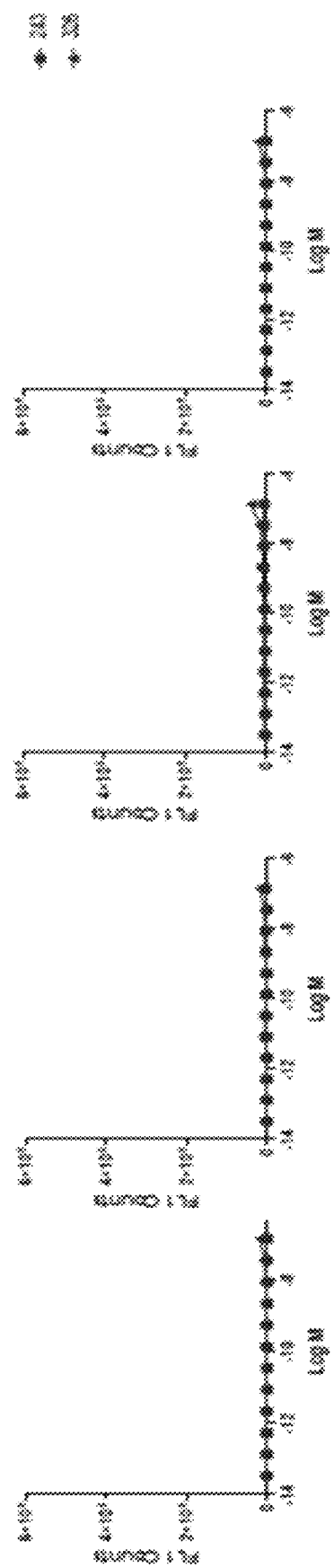

Figure 20

SEQUENCE LISTING

<160> NUMBER OF SEQ ID NOS: 82

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Ser Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide

<400> SEQUENCE: 2

Val Ile Tyr Pro Gly Asn Ser Asp Thr Arg Tyr Asn Gln Lys Phe Lys
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide

<400> SEQUENCE: 3

Asp Tyr Tyr Ser Asn Tyr Val Tyr Tyr Tyr Ala Met Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 9..9
<220> FEATURE:
<221> NAME/KEY: VARIANT
<222> LOCATION: 11..11
<223> OTHER INFORMATION: X = any amino acid

<400> SEQUENCE: 4

Arg Ser Ser Gln Ser Leu Val His Xaa Asn Xaa Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Lys Val Ser Asn Arg Phe Ser
1               5

<210> SEQ ID NO 6
<211> LENGTH: 9

```
<212> TYPE: PRT
<213> ORGANISM: Artificial Sequence
<220> FEATURE:
<223> OTHER INFORMATION: Synthetic peptide

<400> SEQUENCE: 6

Ser Gln Ser Thr His Val Pro Trp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Asp Tyr Gly Met His
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Tyr Ile Asn Ser Gly Ser Ser Ala Ile Tyr Tyr Ala Asp Thr Val Lys
1               5                   10                  15

Gly

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Ala Gly Thr Ala Tyr
1               5

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Lys Ser Ser Gln Ser Leu Leu Asp Ser Asp Gly Lys Thr Tyr Leu Asn
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Gln Val Ser Arg Leu Asp Ser
1               5

<210> SEQ ID NO 12
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Trp Gln Gly Ser His Phe Pro Arg Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Thr Tyr Ala Met Tyr
1               5

<210> SEQ ID NO 14
<211> LENGTH: 19
<212> TYPE: PRT
<213> ORGANISM: Artificial Sequence
<220> FEATURE:
<223> OTHER INFORMATION: Synthetic peptide

<400> SEQUENCE: 14

Arg Ile Arg Ser Lys Ser Ser Asn Phe Ala Thr Tyr Tyr Ala Asp Ser
1               5                   10                  15

Val Lys Asp

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

Gly Gly Ser Asp Tyr
1               5

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

Lys Ser Cys Gln Cys Leu Leu Tyr Ser Asp Gly Lys Thr Tyr Leu Asn
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Gln Val Ser Lys Leu Asp Pro
1               5
```

```
<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Leu Gln Gly Thr Tyr Tyr Pro Tyr Thr
1               5

<210> SEQ ID NO 19
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 9..9
<223> OTHER INFORMATION: X1 is P or S
<220> FEATURE:
<221> NAME/KEY: VARIANT
<222> LOCATION: 11..11
<223> OTHER INFORMATION: X2 is R, T or G

<400> SEQUENCE: 19

Arg Ser Ser Gln Ser Leu Val His Xaa Asn Xaa Asn Thr Tyr Leu His
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic peptide

<400> SEQUENCE: 20

Arg Ser Ser Gln Ser Leu Val His Pro Asn Arg Asn Thr Tyr Leu His
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic peptide

<400> SEQUENCE: 21

Arg Ser Ser Gln Ser Leu Val His Ser Asn Thr Asn Thr Tyr Leu His
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic peptide

<400> SEQUENCE: 22

Arg Ser Ser Gln Ser Leu Val His Ser Asn Gly Asn Thr Tyr Leu His
1               5                   10                  15

<210> SEQ ID NO 23
<211> LENGTH: 19
<212> TYPE: PRT
<213> ORGANISM: Artificial Sequence
<220> FEATURE:
<223> OTHER INFORMATION: Synthetic peptide
```

```
<400> SEQUENCE: 23

Arg Ile Arg Ser Lys Ser Asn Asn Tyr Ala Thr Tyr Tyr Ala Asp Ser
1               5                   10                  15

Val Lys Asp

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Gly Gly Gly Phe Asp Tyr
1               5

<210> SEQ ID NO 25
<211> LENGTH: 16
<212> TYPE: PRT
<213> ORGANISM: Artificial Sequence
<220> FEATURE:
<223> OTHER INFORMATION: Synthetic peptide

<400> SEQUENCE: 25

Lys Ser Ser Gln Ser Leu Leu Tyr Ser Asp Gly Lys Thr Tyr Leu Asn
1               5                   10                  15

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Leu Gln Gly Thr Tyr Tyr Pro Phe Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide

<400> SEQUENCE: 27

Ser Tyr Ala Met Ser
1               5

<210> SEQ ID NO 28
<211> LENGTH: 17
<212> TYPE: PRT
<213> ORGANISM: Artificial Sequence
<220> FEATURE:
<223> OTHER INFORMATION: Synthetic peptide

<400> SEQUENCE: 28

Thr Ile Ser Asp Gly Gly Ser Tyr Thr Tyr Tyr Pro Asp Asn Val Lys
1               5                   10                  15

Gly

<210> SEQ ID NO 29
<211> LENGTH: 8
<212> TYPE: PRT
```

```
<213> ORGANISM: Artificial Sequence
<220> FEATURE:
<223> OTHER INFORMATION: Synthetic peptide

<400> SEQUENCE: 29

Asp Pro Arg Tyr Tyr Phe Asp Tyr
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic peptide

<400> SEQUENCE: 30

Arg Ile Asp Pro Asn Ser Gly Gly Thr Lys Tyr Asn Glu Lys Phe Lys
1               5                   10                  15
Ser

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31

Gly Gly Leu Val Tyr Tyr Phe Asp Tyr
1               5

<210> SEQ ID NO 32
<211> LENGTH: 16
<212> TYPE: PRT
<213> ORGANISM: Artificial Sequence
<220> FEATURE:
<223> OTHER INFORMATION: Synthetic peptide

<400> SEQUENCE: 32

Arg Ser Ser Gln Ser Leu Val His Ser Asn Gly Asn Thr Tyr Leu Tyr
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Arg Val Ser Asn Arg Phe Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Phe Gln Gly Thr His Val Pro His Thr
1               5

<210> SEQ ID NO 35
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 35

Asn Tyr Trp Met Asn
1               5

<210> SEQ ID NO 36
<211> LENGTH: 19
<212> TYPE: PRT
<213> ORGANISM: Artificial Sequence
<220> FEATURE:
<223> OTHER INFORMATION: Synthetic peptide

<400> SEQUENCE: 36

Gln Ile Arg Leu Lys Ser Asp Asn Tyr Ala Thr His Tyr Ala Glu Ser
1               5                   10                  15

Val Lys Gly

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Arg Pro Phe Ser Tyr
1               5

<210> SEQ ID NO 38
<211> LENGTH: 16
<212> TYPE: PRT
<213> ORGANISM: Artificial Sequence
<220> FEATURE:
<223> OTHER INFORMATION: Synthetic peptide

<400> SEQUENCE: 38

Arg Ser Ser Gln Ser Ile Val His Ser Asn Gly Asn Thr Tyr Leu Glu
1               5                   10                  15

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Phe Gln Gly Ser His Val Pro Leu Thr
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide

<400> SEQUENCE: 40

Ser Tyr Val Met His
1               5

<210> SEQ ID NO 41
```

```
<211> LENGTH: 17
<212> TYPE: PRT
<213> ORGANISM: Artificial Sequence
<220> FEATURE:
<223> OTHER INFORMATION: Synthetic peptide

<400> SEQUENCE: 41

Tyr Ile Asn Pro Tyr Asn Asp Gly Thr Lys Tyr Asn Glu Lys Phe Lys
1               5                   10                  15

Gly

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Asn Gly Gly Arg Gly Tyr Ala Met Asp
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Phe Gln Gly Ser His Val Pro Pro Thr
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide

<400> SEQUENCE: 44

Lys Tyr Trp Met Asn
1               5

<210> SEQ ID NO 45
<211> LENGTH: 19
<212> TYPE: PRT
<213> ORGANISM: Artificial Sequence
<220> FEATURE:
<223> OTHER INFORMATION: Synthetic peptide

<400> SEQUENCE: 45

Gln Ile Lys Leu Lys Ser Asp Asn Tyr Ala Thr His Tyr Ala Glu Ser
1               5                   10                  15

Val Lys Gly

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Arg Pro Phe Thr Tyr
1               5
```

<210> SEQ ID NO 47
<211> LENGTH: 16
<212> TYPE: PRT
<213> ORGANISM: Artificial Sequence
<220> FEATURE:
<223> OTHER INFORMATION: Synthetic peptide

<400> SEQUENCE: 47

```
Arg Ser Ser Gln Ser Ile Ile His Ser Asn Gly Asn Thr Tyr Leu Glu
1               5                   10                  15
```

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

```
Phe Gln Gly Ser His Val Pro Trp Thr
1               5
```

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide

<400> SEQUENCE: 49

```
Arg Pro Phe Ala Tyr
1               5
```

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

```
Lys Val Ser Lys Arg Leu Ser
1               5
```

<210> SEQ ID NO 51
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 51

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Tyr Pro Gly Asn Ser Asp Thr Arg Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
```

```
                    85                  90                  95

Thr Arg Asp Tyr Tyr Ser Asn Tyr Val Tyr Tyr Ala Met Asp Tyr
                    100                 105                 110

Trp Gly Gln Gly Thr Thr Val Thr Val Ser Ser
            115                 120
```

<210> SEQ ID NO 52
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 52

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Pro
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Leu Glu Ile Lys
            100                 105                 110
```

<210> SEQ ID NO 53
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 53

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Thr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Leu Glu Ile Lys
            100                 105                 110
```

<210> SEQ ID NO 54
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 54

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Leu Glu Ile Lys
            100                 105                 110
```

<210> SEQ ID NO 55
<211> LENGTH: 112
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 32..32
<220> FEATURE:
<221> NAME/KEY: VARIANT
<222> LOCATION: 34..34
<223> OTHER INFORMATION: X1 and X2 are any amino acid; or X1 is P or S
      and X2 is R, T or G

<400> SEQUENCE: 55

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Xaa
            20                  25                  30

Asn Xaa Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Phe Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 56
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 56

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45
```

```
Gly Val Ile Tyr Pro Gly Asn Ser Asp Thr Arg Tyr Asn Gln Lys Phe
        50                  55                  60

Lys Gly Lys Ala Lys Leu Thr Ala Val Thr Ser Ala Thr Thr Ala Tyr
 65                  70                  75                  80

Met Glu Leu Ser Ser Leu Thr Asn Glu Asp Ser Ala Val Tyr Tyr Cys
                 85                  90                  95

Thr Arg Asp Tyr Tyr Ser Asn Tyr Val Tyr Tyr Ala Met Asp Tyr
                100                 105                 110

Trp Gly Gln Gly Thr Ser Val Thr Val Ser Ser
            115                 120
```

<210> SEQ ID NO 57
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 57

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Phe Phe Cys Ser Gln Ser
                 85                  90                  95

Thr His Val Pro Trp Thr Phe Gly Gly Gly Thr Lys Leu Glu Ile Lys
                100                 105                 110
```

<210> SEQ ID NO 58
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 58

```
Glu Val Gln Leu Val Glu Ser Gly Gly Gly Leu Val Lys Pro Gly Gly
 1               5                  10                  15

Ser Arg Lys Leu Ser Cys Ala Ala Ser Gly Phe Thr Phe Arg Asp Tyr
                20                  25                  30

Gly Met His Trp Val Arg Gln Ala Pro Glu Arg Gly Leu Glu Trp Val
            35                  40                  45

Ala Tyr Ile Asn Ser Gly Ser Ala Ile Tyr Tyr Ala Asp Thr Val
        50                  55                  60

Lys Gly Arg Phe Thr Ile Ser Arg Asp Asn Thr Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Ala Gly Thr Ala Tyr Trp Gly Gln Gly Thr Leu Val Thr Val
                100                 105                 110

Ser Ala
```

<210> SEQ ID NO 59
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 59

Asp Val Val Met Thr Gln Thr Pro Leu Thr Leu Ser Val Thr Phe Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Gln Val Ser Arg Leu Asp Ser Gly Val Pro
    50                  55                  60

Asp Arg Phe Thr Gly Ser Gly Ser Gly Thr Asp Phe Thr Leu Lys Ile
65                  70                  75                  80

Ile Arg Val Glu Ala Glu Asp Leu Gly Val Tyr Tyr Cys Trp Gln Gly
                85                  90                  95

Ser His Phe Pro Arg Thr Phe Gly Gly Gly Thr Lys Leu Glu Ile Lys
            100                 105                 110

<210> SEQ ID NO 60
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 60

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Val Arg Gln Ala Pro Gly Lys Gly Leu Glu Trp Val
        35                  40                  45

Ala Arg Ile Arg Ser Lys Ser Asn Phe Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Gly Ser Asp Tyr Trp Gly Gln Gly Thr Thr Leu
            100                 105                 110

Thr Val Ser Ser
        115

<210> SEQ ID NO 61
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 61

Asp Val Val Met Thr Gln Thr Pro Leu Ser Leu Ser Val Thr Ile Gly
1               5                   10                  15

Gln Pro Ala Ser Ile Ser Cys Lys Ser Cys Gln Cys Leu Leu Tyr Ser
            20                  25                  30

Asp Gly Lys Thr Tyr Leu Asn Trp Leu Gln Gln Arg Pro Gly Gln Ser
        35                  40                  45

Pro Lys Arg Leu Met Tyr Gln Val Ser Lys Leu Asp Pro Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Val Tyr Phe Cys Leu Gln Gly
                85                  90                  95

Thr Tyr Tyr Pro Tyr Thr Phe Gly Ser Gly Thr Lys Leu Glu Ile Lys
            100                 105                 110

<210> SEQ ID NO 62
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 62

Glu Val Gln Leu Val Glu Ser Gly Gly Arg Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Gly Gly Phe Asp Tyr Trp Gly Gln Gly Thr Thr
            100                 105                 110

Leu Thr Val Ser Ser
            115

<210> SEQ ID NO 63
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 63

Asp Val Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Leu Gln Gln Arg Pro Gly Gln Ser
        35                  40                  45

Pro Lys Arg Leu Met Tyr Gln Val Ser Lys Leu Asp Pro Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Val Tyr Tyr Cys Leu Gln Gly
                85                  90                  95

```
Thr Tyr Tyr Pro Phe Thr Phe Gly Thr Gly Thr Lys Leu Glu Ile Lys
            100                 105                 110
```

<210> SEQ ID NO 64
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 64

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Asp Gly Gly Ser Tyr Thr Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Asp Pro Arg Tyr Tyr Phe Asp Tyr Trp Gly Gln Gly Thr Thr
            100                 105                 110

Leu Thr Val Ser Ser
            115
```

<210> SEQ ID NO 65
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 65

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 66
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 66

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
            35                  40                  45

Gly Arg Ile Asp Pro Asn Ser Gly Gly Thr Lys Tyr Asn Glu Lys Phe
50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Leu Val Tyr Tyr Phe Asp Tyr Trp Gly Gln Gly Thr
                100                 105                 110

Thr Leu Thr Val Ser Ser
            115

<210> SEQ ID NO 67
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 67

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
            35                  40                  45

Pro Lys Leu Leu Ile Tyr Arg Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro His Thr Phe Gly Ser Gly Thr Lys Leu Glu Ile Lys
                100                 105                 110

<210> SEQ ID NO 68
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 68

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ser Phe Ser Asn Tyr
            20                  25                  30

Trp Met Asn Trp Val Arg Gln Ser Pro Glu Lys Gly Leu Glu Trp Val
            35                  40                  45

Ala Gln Ile Arg Leu Lys Ser Asp Asn Tyr Ala Thr His Tyr Ala Glu
50                  55                  60

Ser Val Lys Gly Arg Phe Thr Ile Ser Arg Asp Asp Ser Lys Ser Ser
65                  70                  75                  80

-continued

```
Val Tyr Leu Gln Met Asn Asn Leu Arg Ala Glu Asp Thr Gly Ile Tyr
            85                  90                  95

Tyr Cys Thr Glu Arg Pro Phe Ser Tyr Trp Gly Gln Gly Thr Leu Val
            100                 105                 110

Thr Val Ser Ala
        115
```

<210> SEQ ID NO 69
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 69

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 70
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 70

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Gly Gly Arg Gly Tyr Ala Met Asp Tyr Trp Gly Gln Gly
            100                 105                 110

Thr Ser Val Thr Val Ser Ser
        115
```

<210> SEQ ID NO 71
<211> LENGTH: 112
<212> TYPE: PRT

-continued

<400> SEQUENCE: 71

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 72
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 72

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Asn Lys Tyr
            20                  25                  30

Trp Met Asn Trp Val Arg Gln Ser Pro Glu Lys Gly Leu Glu Trp Val
        35                  40                  45

Val Gln Ile Lys Leu Lys Ser Asp Asn Tyr Ala Thr His Tyr Ala Glu
    50                  55                  60

Ser Val Lys Gly Arg Phe Ala Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Leu Arg Pro Phe Thr Tyr Trp Gly Gln Gly Thr Leu Val
            100                 105                 110

Thr Val Ser Ala
        115

<210> SEQ ID NO 73
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 73

Asp Val Leu Met Thr Gln Asn Pro Leu Ser Leu Pro Val Ser Leu Gly
1               5                   10                  15

Asp Gln Ala Ser Ile Ser Cys Arg Ser Ser Gln Ser Ile Ile His Ser
            20                  25                  30

Asn Gly Asn Thr Tyr Leu Glu Trp Tyr Leu Gln Lys Pro Gly Gln Ser
        35                  40                  45

```
Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65              70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
             100                 105                 110
```

<210> SEQ ID NO 74
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 74

```
Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
                 20                  25                  30

Trp Met Asn Trp Val Arg Gln Ser Pro Glu Lys Gly Leu Glu Trp Val
             35                  40                  45

Ala Gln Ile Arg Leu Lys Ser Asp Asn Tyr Ala Thr His Tyr Ala Glu
         50                  55                  60

Ser Val Lys Gly Arg Phe Thr Ile Ser Lys Asp Asp Ser Lys Ser Ser
 65              70                  75                  80

Val Tyr Leu Gln Met Asn Asn Leu Arg Ala Glu Asp Thr Gly Ile Tyr
                 85                  90                  95

Tyr Cys Thr Glu Arg Pro Phe Ala Tyr Trp Gly Gln Gly Thr Leu Val
             100                 105                 110

Thr Val Ser Ser
        115
```

<210> SEQ ID NO 75
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 75

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Lys Arg Leu Ser Gly Val Pro
        50                  55                  60

Asp Arg Phe Ser Gly Ser Gly Ser Gly Thr Glu Phe Thr Leu Lys Ile
 65              70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
             100                 105                 110
```

```
<210> SEQ ID NO 76
<211> LENGTH: 112
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 32..32
<223> OTHER INFORMATION: X1 = any amino acid
<220> FEATURE:
<221> NAME/KEY: VARIANT
<222> LOCATION: 34..34
<223> OTHER INFORMATION: X2 = any amino acid

<400> SEQUENCE: 76

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Xaa
            20                  25                  30

Asn Xaa Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Phe Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 77
<211> LENGTH: 112
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 32..32
<223> OTHER INFORMATION: X1 is P or S
<220> FEATURE:
<221> NAME/KEY: VARIANT
<222> LOCATION: 34..34
<223> OTHER INFORMATION: X2 is R, T or G

<400> SEQUENCE: 77

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Xaa
            20                  25                  30

Asn Xaa Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Phe Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 78
```

<211> LENGTH: 330
<212> TYPE: PRT
<213> ORGANISM: Artificial Sequence
<220> FEATURE:
<223> OTHER INFORMATION: Synthetic polypeptide

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 79
<211> LENGTH: 107
<212> TYPE: PRT
<213> ORGANISM: Artificial Sequence
<220> FEATURE:
<223> OTHER INFORMATION: Synthetic polypeptide

```
<400> SEQUENCE: 79

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 80
<211> LENGTH: 36
<212> TYPE: PRT
<213> ORGANISM: Artificial Sequence
<220> FEATURE:
<223> OTHER INFORMATION: epitiope

<400> SEQUENCE: 80

Met Ala Asp Asp Tyr Gly Ser Glu Ser Thr Ser Ser Met Glu Asp Tyr
1               5                   10                  15

Val Asn Phe Asn Phe Thr Asp Phe Tyr Cys Glu Lys Asn Asn Val Arg
            20                  25                  30

Gln Phe Ala Ser
        35

<210> SEQ ID NO 81
<211> LENGTH: 369
<212> TYPE: PRT
<213> ORGANISM: Homo sapiens

<400> SEQUENCE: 81

Met Thr Pro Thr Asp Phe Thr Ser Pro Ile Pro Asn Met Ala Asp Asp
1               5                   10                  15

Tyr Gly Ser Glu Ser Thr Ser Ser Met Glu Asp Tyr Val Asn Phe Asn
            20                  25                  30

Phe Thr Asp Phe Tyr Cys Glu Lys Asn Asn Val Arg Gln Phe Ala Ser
        35                  40                  45

His Phe Leu Pro Pro Leu Tyr Trp Leu Val Phe Ile Val Gly Ala Leu
    50                  55                  60

Gly Asn Ser Leu Val Ile Leu Val Tyr Trp Tyr Cys Thr Arg Val Lys
65                  70                  75                  80

Thr Met Thr Asp Met Phe Leu Leu Asn Leu Ala Ile Ala Asp Leu Leu
                85                  90                  95

Phe Leu Val Thr Leu Pro Phe Trp Ala Ile Ala Ala Ala Asp Gln Trp
            100                 105                 110

Lys Phe Gln Thr Phe Met Cys Lys Val Val Asn Ser Met Tyr Lys Met
        115                 120                 125

Asn Phe Tyr Ser Cys Val Leu Leu Ile Met Cys Ile Ser Val Asp Arg
    130                 135                 140

Tyr Ile Ala Ile Ala Gln Ala Met Arg Ala His Thr Trp Arg Glu Lys
145                 150                 155                 160
```

```
Arg Leu Leu Tyr Ser Lys Met Val Cys Phe Thr Ile Trp Val Leu Ala
                165                 170                 175

Ala Ala Leu Cys Ile Pro Glu Ile Leu Tyr Ser Gln Ile Lys Glu Glu
            180                 185                 190

Ser Gly Ile Ala Ile Cys Thr Met Val Tyr Pro Ser Asp Glu Ser Thr
        195                 200                 205

Lys Leu Lys Ser Ala Val Leu Thr Leu Lys Val Ile Leu Gly Phe Phe
    210                 215                 220

Leu Pro Phe Val Val Met Ala Cys Cys Tyr Thr Ile Ile His Thr
225                 230                 235                 240

Leu Ile Gln Ala Lys Lys Ser Ser Lys His Lys Ala Leu Lys Val Thr
                245                 250                 255

Ile Thr Val Leu Thr Val Phe Val Leu Ser Gln Phe Pro Tyr Asn Cys
            260                 265                 270

Ile Leu Leu Val Gln Thr Ile Asp Ala Tyr Ala Met Phe Ile Ser Asn
        275                 280                 285

Cys Ala Val Ser Thr Asn Ile Asp Ile Cys Phe Gln Val Thr Gln Thr
    290                 295                 300

Ile Ala Phe Phe His Ser Cys Leu Asn Pro Val Leu Tyr Val Phe Val
305                 310                 315                 320

Gly Glu Arg Phe Arg Arg Asp Leu Val Lys Thr Leu Lys Asn Leu Gly
                325                 330                 335

Cys Ile Ser Gln Ala Gln Trp Val Ser Phe Thr Arg Arg Glu Gly Ser
            340                 345                 350

Leu Lys Leu Ser Ser Met Leu Leu Glu Thr Thr Ser Gly Ala Leu Ser
        355                 360                 365

Leu

<210> SEQ ID NO 82
<211> LENGTH: 357
<212> TYPE: PRT
<213> ORGANISM: Homo sapiens

<400> SEQUENCE: 82

Met Ala Asp Asp Tyr Gly Ser Glu Ser Thr Ser Ser Met Glu Asp Tyr
1               5                   10                  15

Val Asn Phe Asn Phe Thr Asp Phe Tyr Cys Glu Lys Asn Asn Val Arg
            20                  25                  30

Gln Phe Ala Ser His Phe Leu Pro Pro Leu Tyr Trp Leu Val Phe Ile
        35                  40                  45

Val Gly Ala Leu Gly Asn Ser Leu Val Ile Leu Val Tyr Trp Tyr Cys
    50                  55                  60

Thr Arg Val Lys Thr Met Thr Asp Met Phe Leu Leu Asn Leu Ala Ile
65                  70                  75                  80

Ala Asp Leu Leu Phe Leu Val Thr Leu Pro Phe Trp Ala Ile Ala Ala
                85                  90                  95

Ala Asp Gln Trp Lys Phe Gln Thr Phe Met Cys Lys Val Val Asn Ser
            100                 105                 110

Met Tyr Lys Met Asn Phe Tyr Ser Cys Val Leu Leu Ile Met Cys Ile
        115                 120                 125

Ser Val Asp Arg Tyr Ile Ala Ile Ala Gln Ala Met Arg Ala His Thr
    130                 135                 140

Trp Arg Glu Lys Arg Leu Leu Tyr Ser Lys Met Val Cys Phe Thr Ile
145                 150                 155                 160
```

-continued

```
Trp Val Leu Ala Ala Ala Leu Cys Ile Pro Glu Ile Leu Tyr Ser Gln
            165                 170                 175
Ile Lys Glu Glu Ser Gly Ile Ala Ile Cys Thr Met Val Tyr Pro Ser
            180                 185                 190
Asp Glu Ser Thr Lys Leu Lys Ser Ala Val Leu Thr Leu Lys Val Ile
        195                 200                 205
Leu Gly Phe Phe Leu Pro Phe Val Val Met Ala Cys Cys Tyr Thr Ile
        210                 215                 220
Ile Ile His Thr Leu Ile Gln Ala Lys Lys Ser Ser Lys His Lys Ala
225                 230                 235                 240
Leu Lys Val Thr Ile Thr Val Leu Thr Val Phe Val Leu Ser Gln Phe
            245                 250                 255
Pro Tyr Asn Cys Ile Leu Leu Val Gln Thr Ile Asp Ala Tyr Ala Met
            260                 265                 270
Phe Ile Ser Asn Cys Ala Val Ser Thr Asn Ile Asp Ile Cys Phe Gln
            275                 280                 285
Val Thr Gln Thr Ile Ala Phe Phe His Ser Cys Leu Asn Pro Val Leu
        290                 295                 300
Tyr Val Phe Val Gly Glu Arg Phe Arg Arg Asp Leu Val Lys Thr Leu
305                 310                 315                 320
Lys Asn Leu Gly Cys Ile Ser Gln Ala Gln Trp Val Ser Phe Thr Arg
            325                 330                 335
Arg Glu Gly Ser Leu Lys Leu Ser Ser Met Leu Leu Glu Thr Thr Ser
            340                 345                 350
Gly Ala Leu Ser Leu
            355
```

THERAPEUTIC BINDING MOLECULES

1 FIELD OF THE INVENTION

The present invention relates to binding molecules, such as antibodies, that bind to the chemokine receptor CCR9. More particularly, the invention relates to the treatment of CCR9-mediated diseases or conditions such as inflammatory bowel disease (IBD), and methods for the detection of CCR9, which make use of the binding molecules of the invention.

2 BACKGROUND OF THE INVENTION

IBD is a group of chronic disorders of the gastrointestinal tract characterized pathologically by intestinal inflammation and epithelial injury. Two forms of IBD, Crohn's disease and ulcerative colitis, are associated with marked morbidity and can have a major impact on an individual's quality of life and their ability to work [1]. These morbidities highlight the need for improved therapies for IBD.

Therapeutic interventions for IBD are tailored to address symptomatic response and subsequent tolerance of the intervention. Current therapies include aminosalicylates, corticosteroids and antibodies. However, despite these treatments, it is estimated that surgical interventions are required in up to two thirds of Crohn's disease patients during their lifetime [2]. The clinical management of Crohn's disease has historically employed a step-up approach, starting with steroids, immunosuppressants (thiopurines and methotrexate), and/or aminosalicylates, although evidence for efficacy of the latter is very limited [3]. No licensed therapy achieves durable remission in the majority of patients.

Targeting anti-CCR9 antibodies has been proposed as a mechanism for the treatment of cancer. Aberrant CCR9 expression in ovarian carcinomas, prostate cancer, breast cancer and melanomas is correlated with in vitro invasiveness in response to CCL25. CCL25 engagement enhances cell survival and resistance to apoptosis. Somovilla-Crespo et al. 2018 [4] and WO2015075269 A1 describe mouse anti-CCR9 antibodies 91 R (mouse anti-human CCR9 IgG2b) and 92R (mouse anti-human CCR9 IgG2a).

Therefore, there exists a need for an improved medicament for treating or preventing such disorders. The present invention solves one or more of the above-mentioned problems.

3 SUMMARY OF THE INVENTION

The inventors have found that the chemokine receptor, CCR9, is highly expressed in the colon and ileum of patients with IBD where it co-expresses with the inflammatory cytokines IFN-γ, IL-4 and IL-17. The inventors have successfully generated binding molecules which bind to CCR9-expressing cells, inhibit the interaction between CCR9 and its natural ligand CCL25 and prevent CCL25 mediated CCR9 internalisation. Advantageously, the binding molecules can induce death of the CCR9-expressing cells to which they bind, for example by mediating an antibody dependent cell-mediated cytotoxicity (ADCC) against the CCR9-expressing cells to which they bind. The development of a binding molecule that inhibits binding of CCL25 to CCR9 and induces death of a CCR9-expressing cell to which it binds is particularly advantageous for subjects with IBD.

Thus, the invention relates to binding molecules that bind to CCR9. The binding molecules of the invention preferably inhibit binding of CCL25 to CCR9. The binding molecules of the invention are preferably capable of inducing death of CCR9-expressing cells to which they bind. For example, the binding molecules may be capable of mediating an ADCC response against cells to which they bind. The binding molecules of the invention are preferably capable of preventing or inhibiting migration of CCR9-expressing cells to which they bind. For example, the binding molecules may prevent migration of CCR9-expressing cells in response to CCL25, or the binding molecules may be capable of preventing migration of CCR9-expressing cells from the periphery into the gut of a subject.

In one aspect the invention provides a binding molecule that binds to CCR9 and comprises a heavy chain variable (VH) region having a set of CDRs HCDR1, HCDR2 and HCDR3 and a light chain variable (VL) region having a set of CDRs LCDR1, LCDR2 and LCDR3, wherein (a) the VH region amino acid sequence comprises HCDR1 of SEQ ID NO: 1, HCDR2 of SEQ ID NO: 2 and HCDR3 of SEQ ID NO: 3, and wherein the VL region amino acid sequence comprises LCDR1 of SEQ ID NO: 4 (RSSQSLVHX$_1$NX$_2$NTYLH wherein X$_1$ and X$_2$ are any amino acid), LCDR2 of SEQ ID NO: 5 and LCDR3 of SEQ ID NO: 6; (b) the VH region amino acid sequence comprises HCDR1 of SEQ ID NO: 7, HCDR2 of SEQ ID NO: 8 and HCDR3 of SEQ ID NO: 9, and wherein the VL region amino acid sequence comprises LCDR1 of SEQ ID NO: 10, LCDR2 of SEQ ID NO: 11 and LCDR3 of SEQ ID NO: 12; or (c) the VH region amino acid sequence comprises HCDR1 of SEQ ID NO: 13, HCDR2 of SEQ ID NO: 14 and HCDR3 of SEQ ID NO: 15, and wherein the VL region amino acid sequence comprises LCDR1 of SEQ ID NO: 16, LCDR2 of SEQ ID NO: 17 and LCDR3 of SEQ ID NO: 18; or wherein any one or more of said HCDR1, HCDR2, HCDR3, LCDR1, LCDR2 and LCDR3 comprises 1, 2 or 3 amino acid substitutions compared to said sequences.

The binding molecule of the invention may comprise a VH region amino acid sequence comprising HCDR1 of SEQ ID NO: 1, HCDR2 of SEQ ID NO: 2 and HCDR3 of SEQ ID NO: 3, and a VL region amino acid sequence comprising LCDR2 of SEQ ID NO: 5 and LCDR3 of SEQ ID NO: 6, and LCDR1 having an amino acid sequence selected from: SEQ ID NO: 4, SEQ ID NO: 19 (RSSQSLVHX$_1$NX$_2$NTYLH wherein X$_1$ of SEQ ID NO: 19 is P or S and X$_2$ of SEQ ID NO: 19 is R, T or G), SEQ ID NO: 20, SEQ ID NO: 21, and SEQ ID NO: 22.

The binding molecules of the invention preferably comprise an immunoglobulin Fc domain, or a fragment thereof that retains the ability to bind to one or more Fc receptors. For example, the binding molecule may comprise a human IgG1 Fc domain or fragment thereof. The binding molecules of the invention are preferably afucosylated. For example, the binding molecules may be afucosylated at amino acid position 297. The binding molecule of the invention may be present in a composition comprising multiple copies of said binding molecule, wherein at least 50%, 75%, 90%, 95%, 98%, 99% or 100% of the copies of the binding molecule in the composition are afucosylated.

In another aspect, the invention provides a binding molecule that binds to CCR9, wherein the binding molecule does not compete for binding to CCR9 with another binding molecule of the invention, such as does not compete for binding to CCR9 with a binding molecule as described above, such as does not compete for binding to CCR9 with a binding molecule as described herein for use in therapy. The binding molecule of this aspect may be used to determine the abundance of CCR9+ cells in a sample which has been contacted with a binding molecule of the invention.

Similarly, the invention provides a method of assessing the depletion of CCR9-expressing cells by a binding molecule of the invention, the method comprising: (i) contacting said binding molecule with a population of cells, wherein the population of cells comprises CCR9-expressing cells and immune effector cells, under conditions suitable to allow for antibody dependent cell-mediated cytotoxicity by the effector cells; (ii) contacting said population of cells with a binding molecule that binds to CCR9, and that does not compete for binding to CCR9 with the binding molecule of step (i); (iii) detecting CCR9-expressing cells in the population of cells that are bound by the binding molecule of (ii); (iv) comparing the amount of CCR9-expressing cells detected in step (iii) with the amount of CCR9-expressing cells in the original cell population used in step (i), and thereby determining the amount of CCR9-expressing cells that were depleted in step (i).

The invention also provides an isolated polynucleotide encoding any binding molecule of the invention. Also provided is a vector comprising a polynucleotide of the invention operably associated with a promoter. Also provided is a vector comprising a polynucleotide encoding the VH region of a binding molecule of the invention, and a polynucleotide encoding the VL region of a binding molecule of the invention, wherein said polynucleotides are operably associated with one or more promoters.

The invention provides a host cell comprising a polynucleotide of the invention or a vector of the invention. Also provided is a method of producing a binding molecule of the invention, comprising expressing a polynucleotide of the invention or a vector of the invention in a host cell.

The invention provides a pharmaceutical composition comprising the binding molecule of the invention, and a pharmaceutically acceptable carrier or diluent.

The invention also relates to using the binding molecules of the invention in medicine, such as a binding molecule of the invention for use in therapy. The invention relates to treating a CCR9-mediated disease or condition in a subject, by a method comprising administering to the subject an effective amount of a binding molecule of the invention, or a composition of the invention. The invention also relates to treating a CCR9-mediated disease or condition in a subject, by a method comprising administering to the subject an effective amount of a binding molecule which binds to CCR9, wherein said binding molecule is capable of (i) inhibiting binding of CCL25 to CCR9, and (ii) mediating antibody dependent cell-mediated cytotoxicity against a CCR9-expressing cell to which it binds.

The binding molecules as described herein may also be used to detect CCR9. For example, the invention provides a method for detecting the presence of a CCR9 polypeptide in a sample, comprising: (a) contacting a sample with a binding molecule that binds to CCR9, such as any binding molecule of the invention or binding molecule as described herein, to provide a binding molecule-antigen complex; (b) detecting the presence or absence of said binding molecule-antigen complex; (c) wherein the presence of the binding molecule-antigen complex confirms the presence of a CCR9 polypeptide.

The present invention relates to improved anti-CCR9 antibodies and there use in the treatment of inflammatory bowel disease. The present invention particularly relates to a humanized afucosylated monoclonal antibody that specifically binds to the C-C motif chemokine receptor 9 (CCR9). Via its Fc receptor functionality, binding of the antibody to the CCR9 receptor initiates an ADCC response resulting in depletion of the CCR9 expressing cell populations. The antibodies of the invention are humanised, CDR optimized. The antibodies are afucosylated without any loss of potency.

4 BRIEF DESCRIPTION OF THE DRAWINGS

Figure 1B:
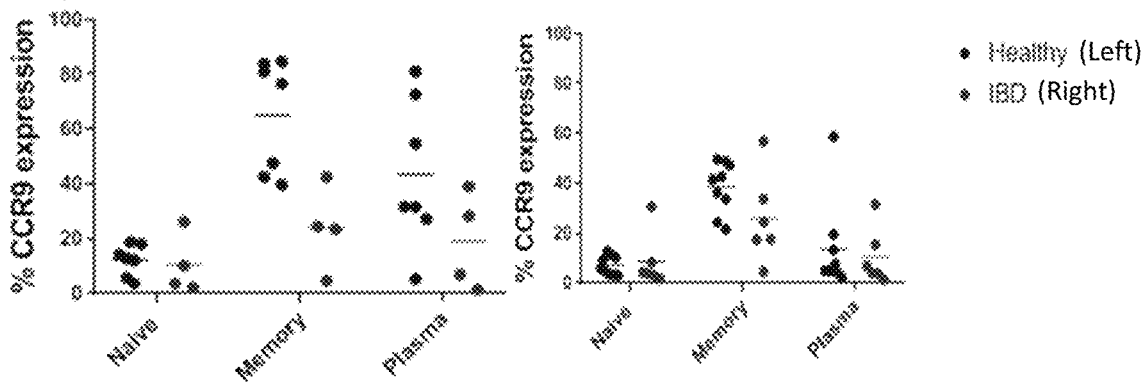
Figure 1C:
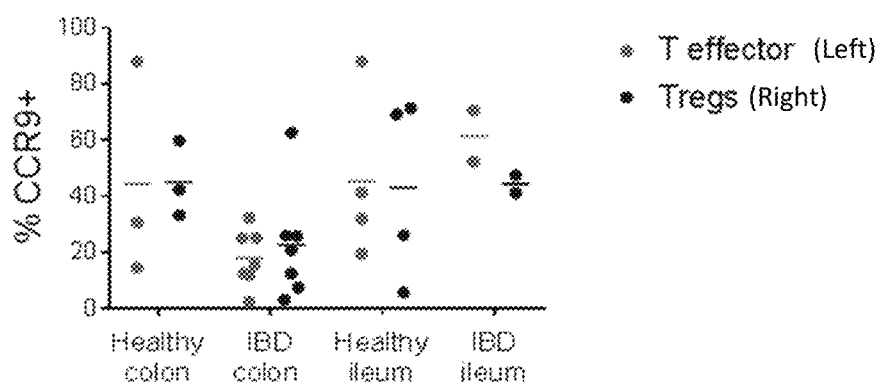

FIG. 1A-1C: CCR9 expression in various cell types.

FIG. 1A: Expression of CCR9 in CD4+ cells from cynomolgus and human cells blood, mesenteric lymph node (cynomolgus only), colon, ileum, and thymus; FIG. 1B: Expression of CCR9 in B cells in the ileum (left) and colon (right) of healthy and IBD patients; FIG. 1C: Expression of CCR9 in T effector cells and Tregs from the colon or ileum of healthy or IBD patients.

FIG. 2A-2B: The association of CCR9 with pro-inflammatory cytokines in CD4+ T cells.

FIG. 2A: IFN-γ, IL-4, and IL-17 expression in CCR9− and CCR9+ cells; FIG. 2B: Fold change in expression level of cytokines assessed in FIG. 2A between CD4+CCD9− cells and CD4+CCR9+ cells.

FIG. 3A-3B: The aligned amino acid sequences of the variable regions of nine anti-CCR9 antibodies FIG. 3A: VH region; FIG. 3B: VL region. Locations of CDRs (HCDR1, HCDR2, HCDR3, LCDR1, LCDR2 and LCDR3 are indicated underlined. Locations of framework (FW) regions are also indicated.

Figure 4:
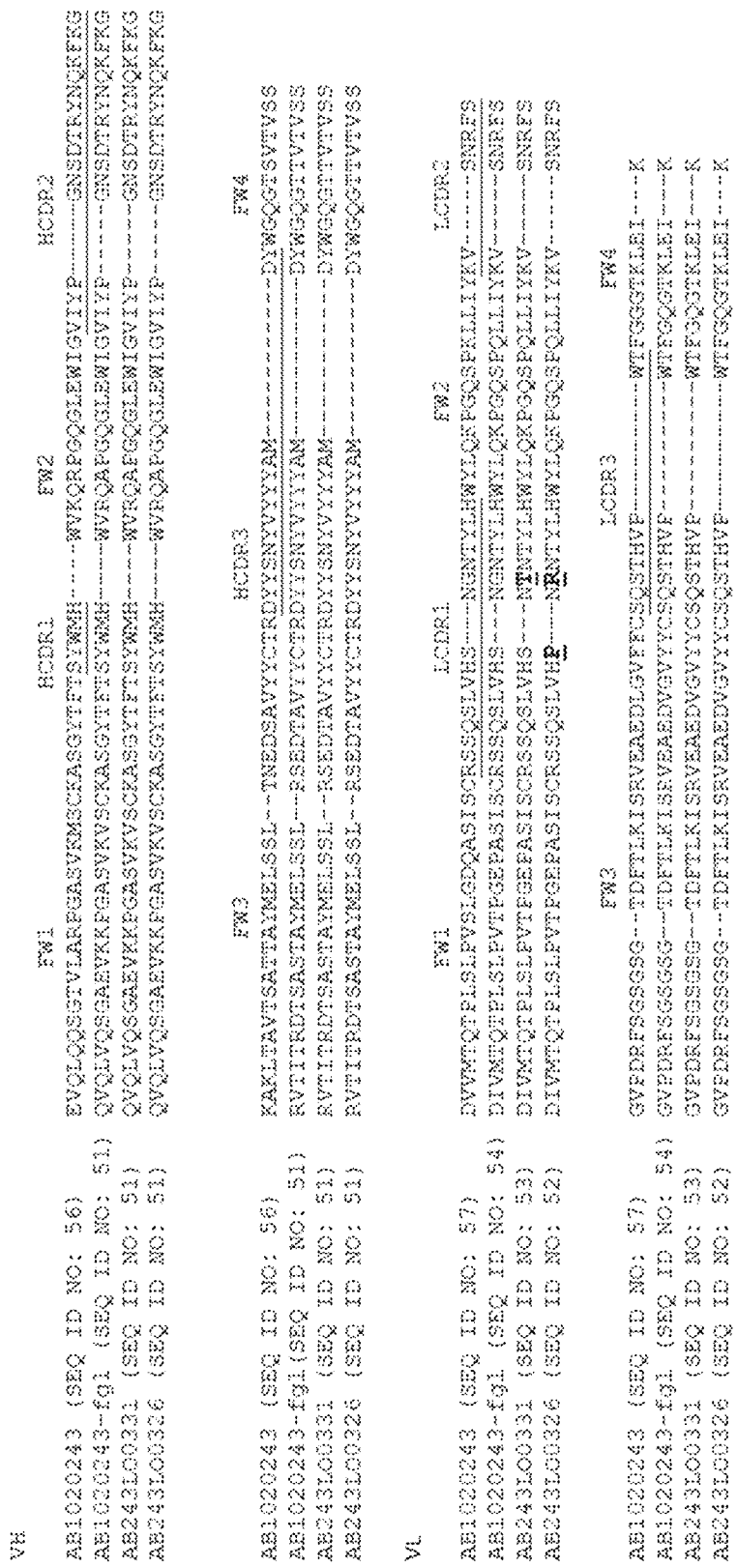

FIG. 4: The aligned VH and VL regions of antibody AB1020243, a humanised form of that antibody (AB1020243-fg1), and two CDR optimised forms of the antibody (243LO0326 and 243LO0331)

Figure 5A:
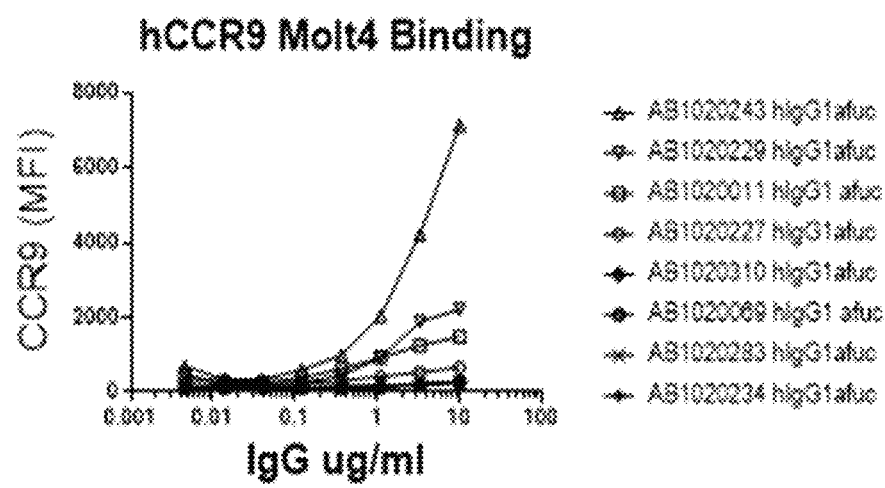
Figure 5B:
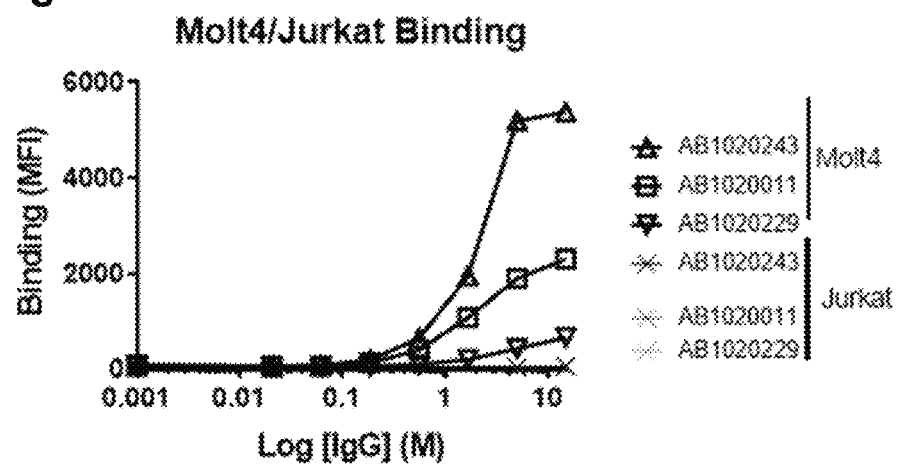

FIG. 5A-5B: The binding of anti-CCR9 antibodies to cells expressing, or not expressing CCR9

FIG. 5A: Binding to Molt 4 cell line; FIG. 5B: Binding to the Molt 4 and Jurkat cell lines FIG. 6: The binding of AB1020243 to different forms of CCR9 in HEK cells As a control, binding was assessed in HEK cells not transfected with CCR9 (Parental HEK), and binding was then also assessed in HEK cells overexpressing human CCR9A (Hu A HEK), human CCR9B (Hu B HEK), cynomolgus CCR9 (Cyno HEK), mouse CCR9 (Mouse HEK) and rat CCR9 (Rat HEK).

Figure 7:
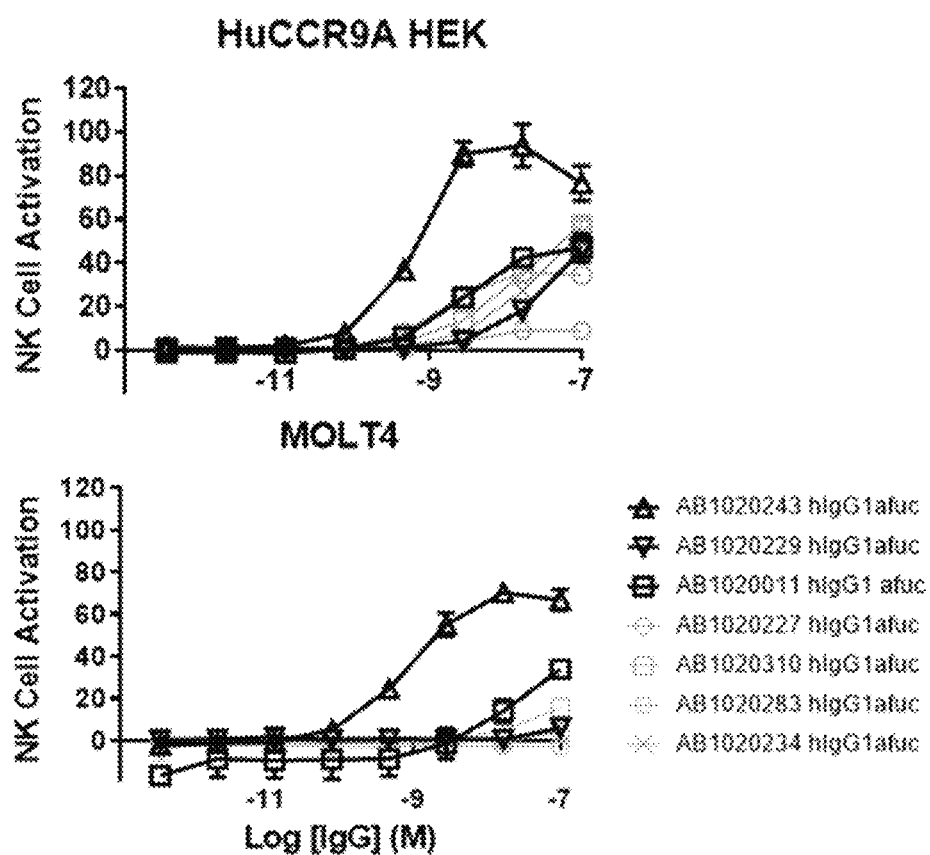

FIG. 7: The activation of NK cells by afucosylated anti-CCR9 antibodies pre-incubated with HEK cells expressing CCR9A (top) or Molt 4 cells (bottom).

Figure 8:
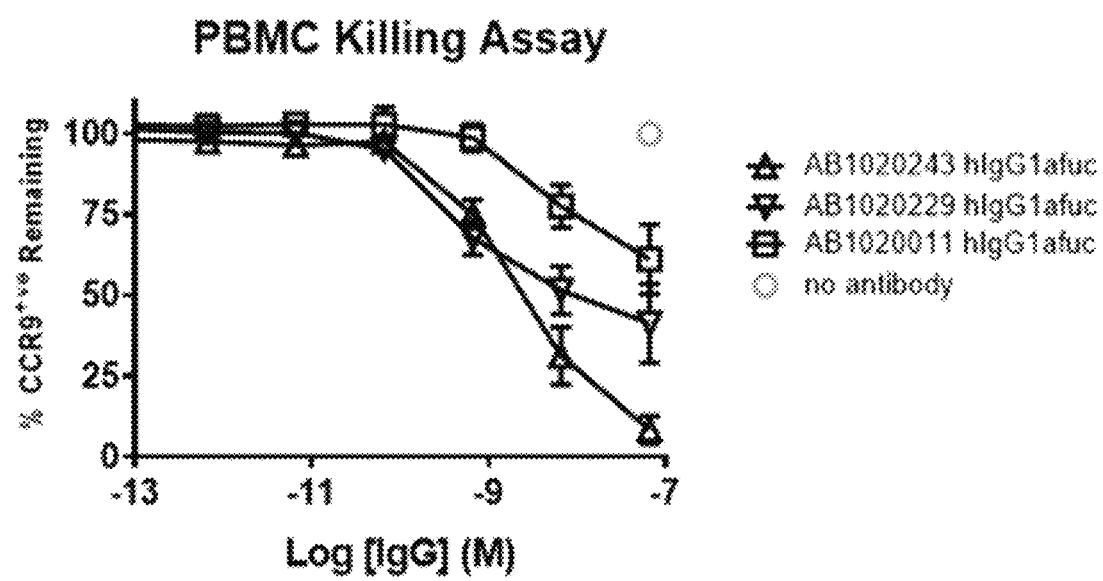

FIG. 8: The effects of treatment with anti-CCR9 antibodies on the number of CCR9+CD4+ PBMC.

FIG. 9A-9G: Comparison of the binding to various ligands of the chimeric antibody AB1020243 and its humanised version.

Figure 9A:
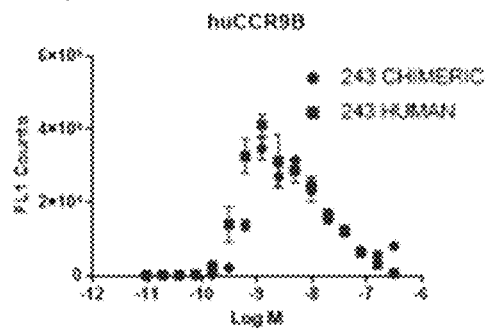
Figure 9B:
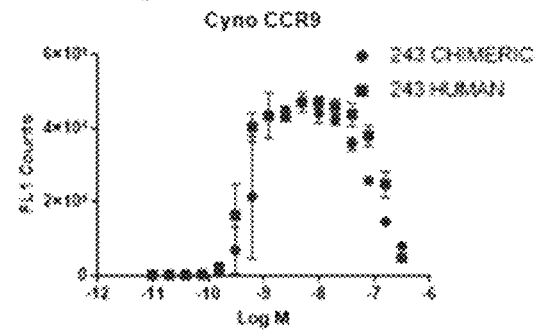
Figure 9C:
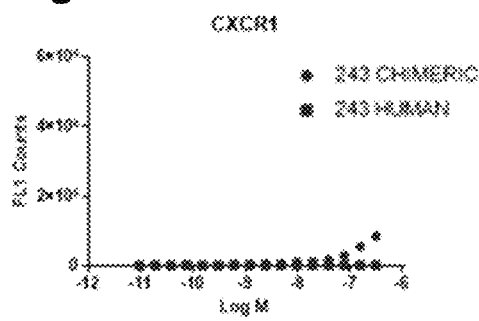
Figure 9D:
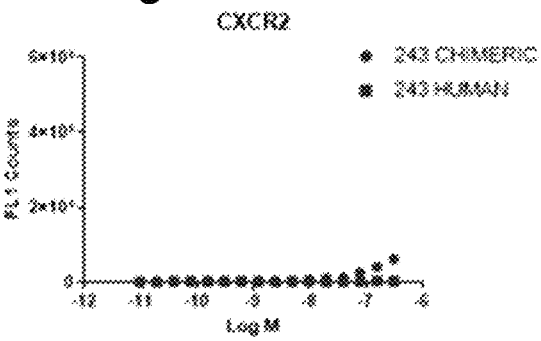
Figure 9E:
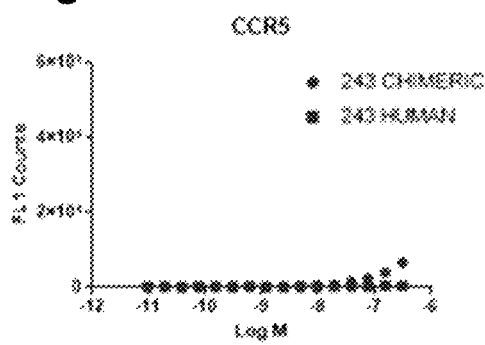
Figure 9F:
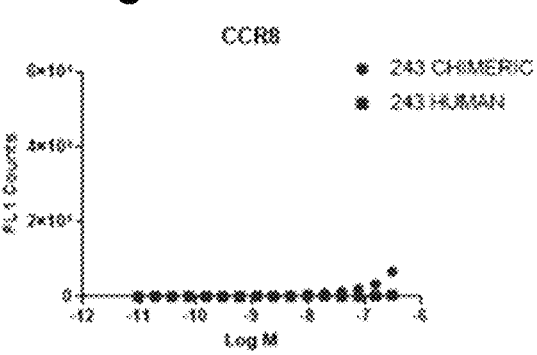
Figure 9G:
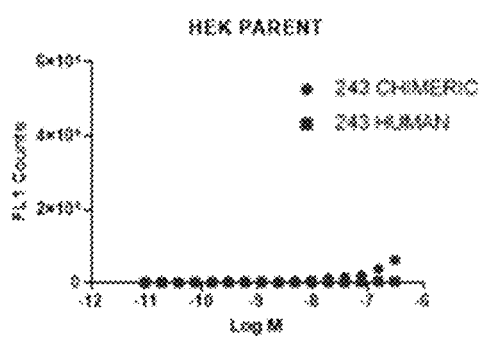

FIG. 9A: human CCR9B; FIG. 9B: cynomolgus CCR9; FIG. 9C: CXCR1; FIG. 9D: CXCR2; FIG. 9E: CCR5; FIG. 9F: CCR8; FIG. 9G: HEK cells not transfected with CCR9.

Figure 10A:
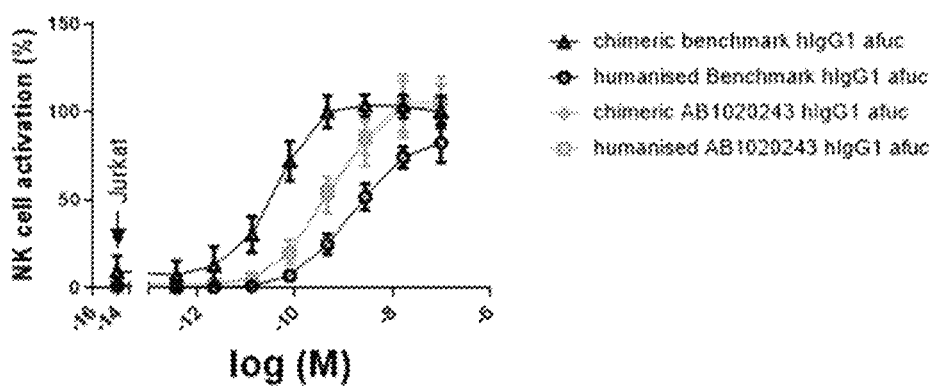
Figure 10B:
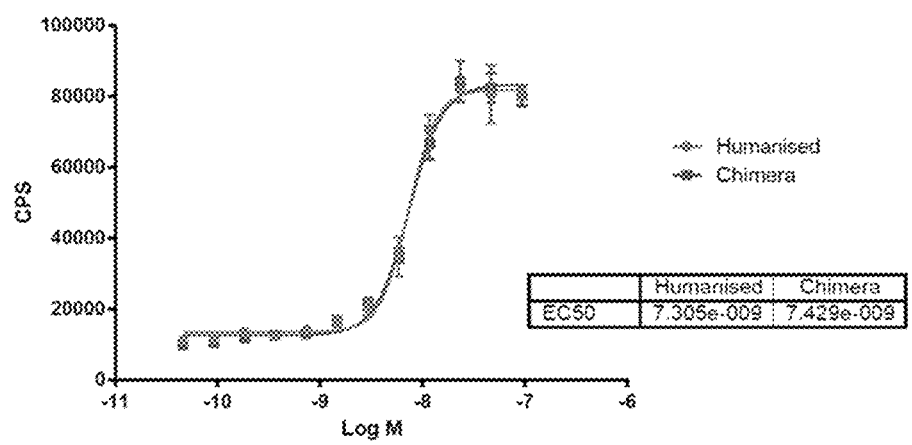

FIG. 10A-10B: Comparison of the AB1020243 antibody with its humanised version

FIG. 10A: NK cell activation after binding to the Molt 4 cell line; FIG. 10B: Kinetic properties of the humanised and chimeric AB1020243 afuc antibodies.

Figure 11:
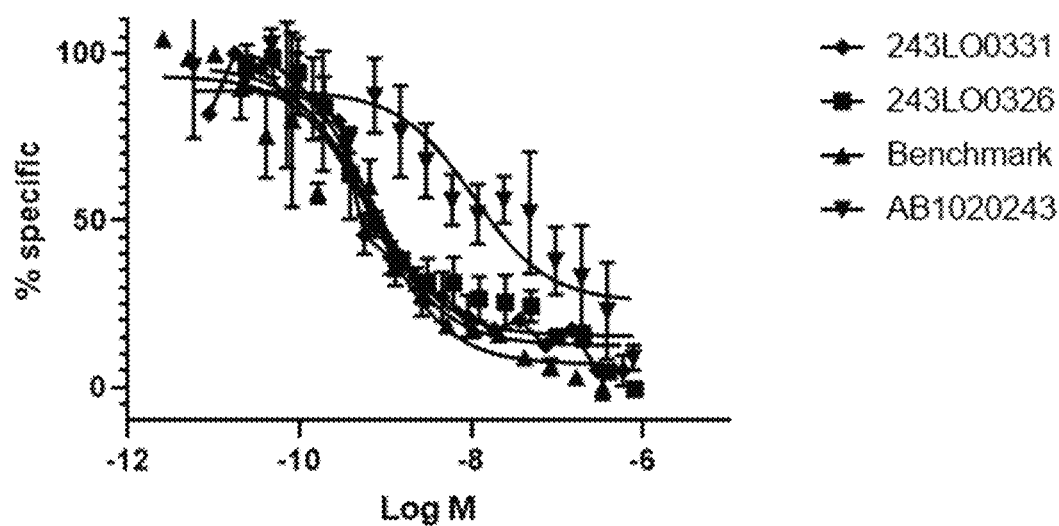

FIG. 11: The ability of anti-CCR9 antibodies to compete with CCL25 for binding to CCR9.

FIG. 12A-12G: The binding of 243LO0326 and AB1020243 to ligands

FIG. 12A: human CCR9A; FIG. 12B: human CCR9B; FIG. 12C: cynomolgus CCR9A;

FIG. 12D: CCR5; FIG. 12E: CCR8; FIG. 12F: CXCR1; and FIG. 12Q: CXCR2.

Figure 13A:
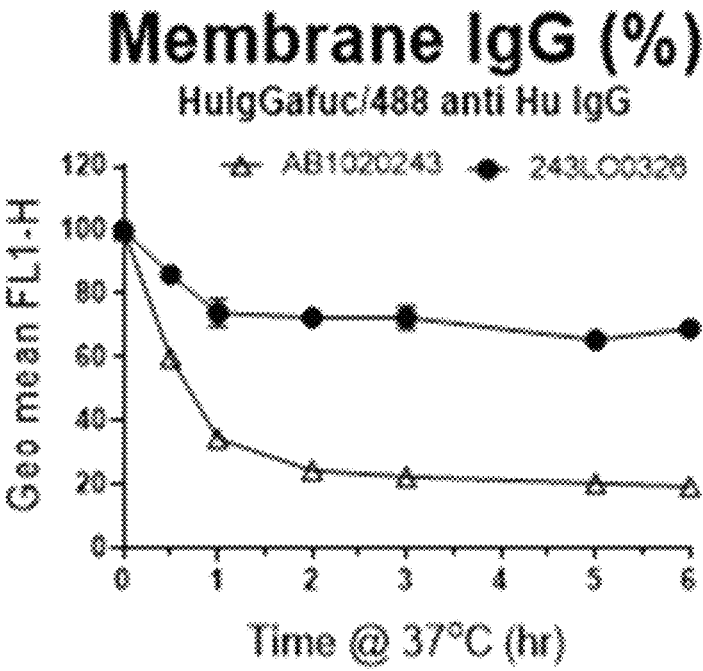
Figure 13B:
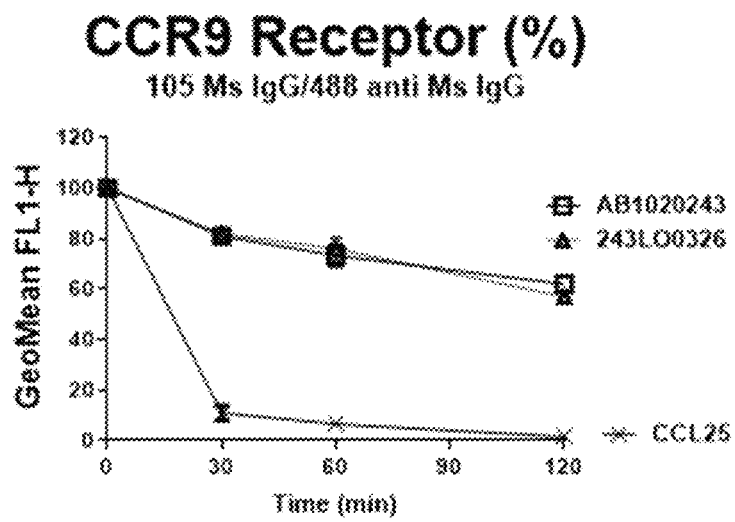

FIG. 13A-13B: The amount of antibody AB1020243 or antibody 243LO0326 bound at the cell surface over time The amount of antibody AB1020243 or antibody 243LO0326 bound at the cell surface over time (FIG. 13A) and the effect of antibody or CCL25 treatment on CCR9 receptor levels at the cell surface overtime (FIG. 13B).

Figure 14A:
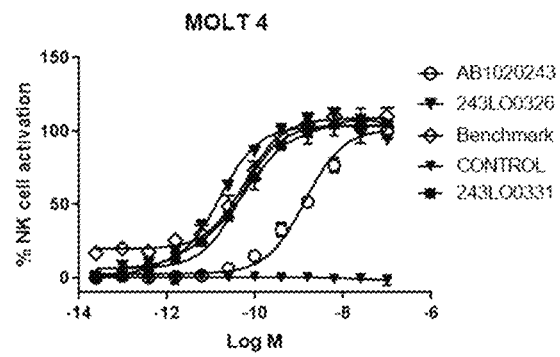
Figure 14B:
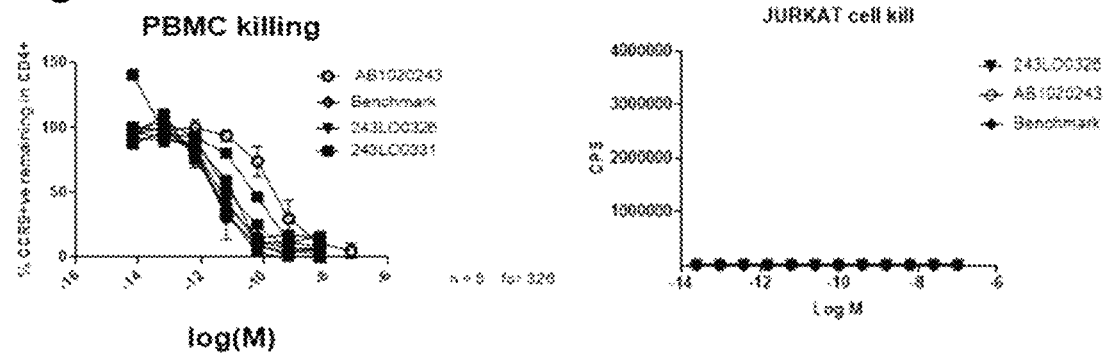
Figure 14C:
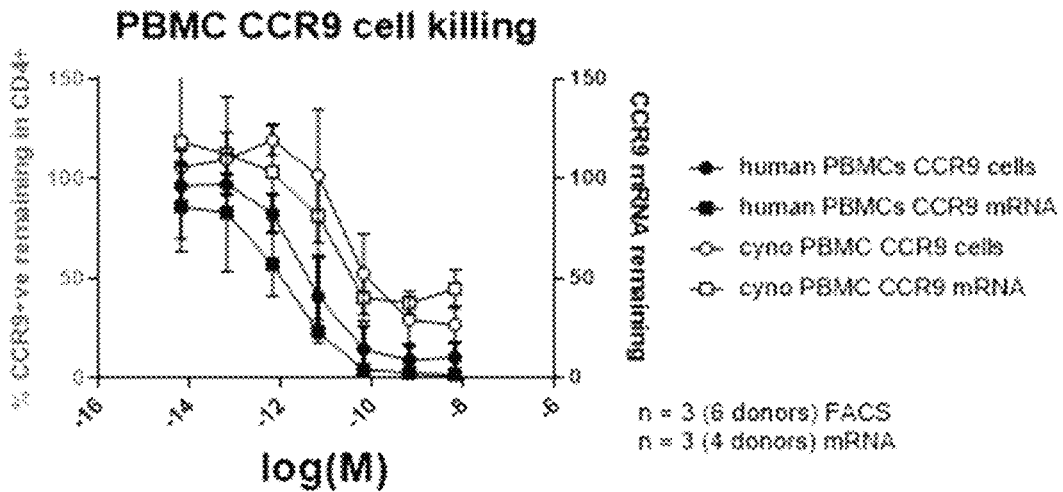

FIG. 14A-14C: The effects of anti-CCR9 antibodies in killing Molt 4 cells

FIG. 14A: NK cell activation assay; FIG. 14B: PBMC and Jurkat cells; FIG. 14C: human or cynomolgus PBMC.

Figure 15A:
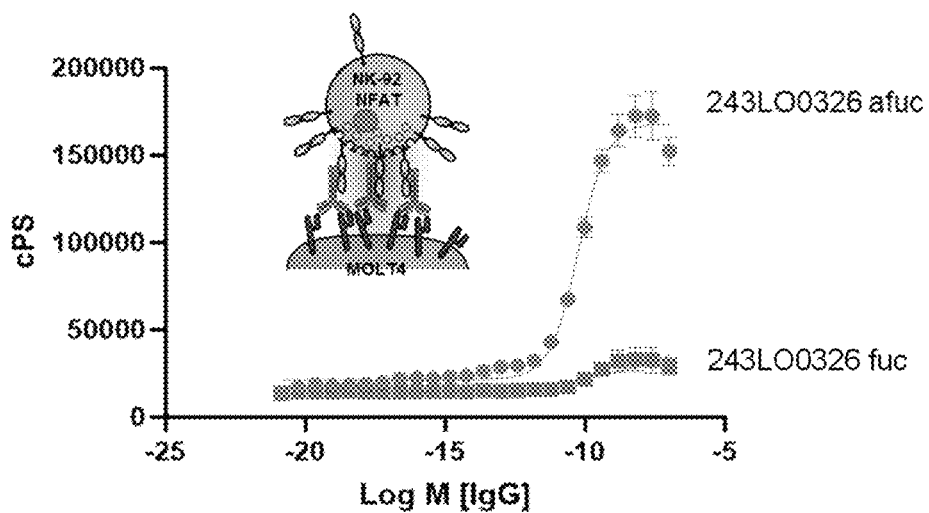
Figure 15B:
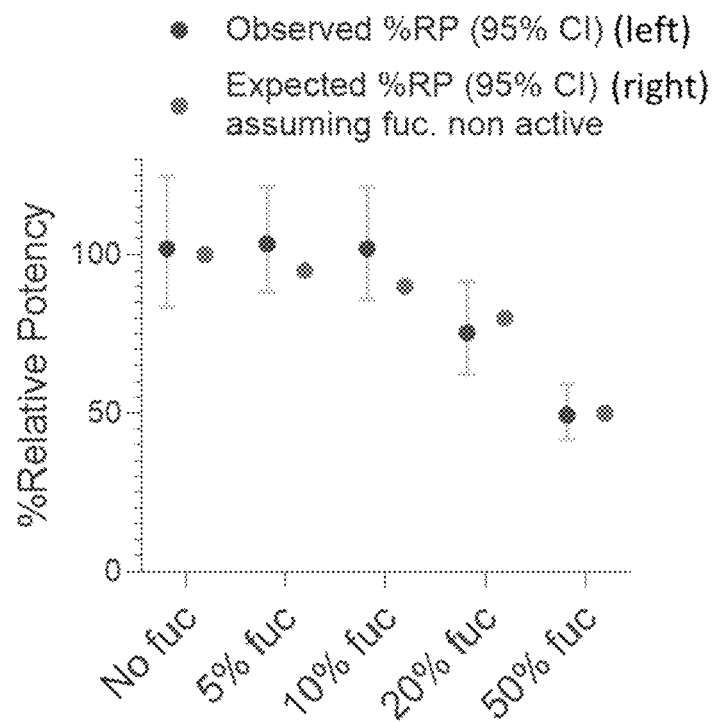

FIG. 15A-15B: Impact of fucosylation on potency

FIG. 15A: Effect of afucosuylation on ADDC. FIG. 15B: ADCC activity of fucosylated vs. afucosylated species in a fucosylation spiking study. RP: Relative potency.

FIG. 16A-16D: Targeted in vivo depletion of CCR9+ T cells

Figure 16A:
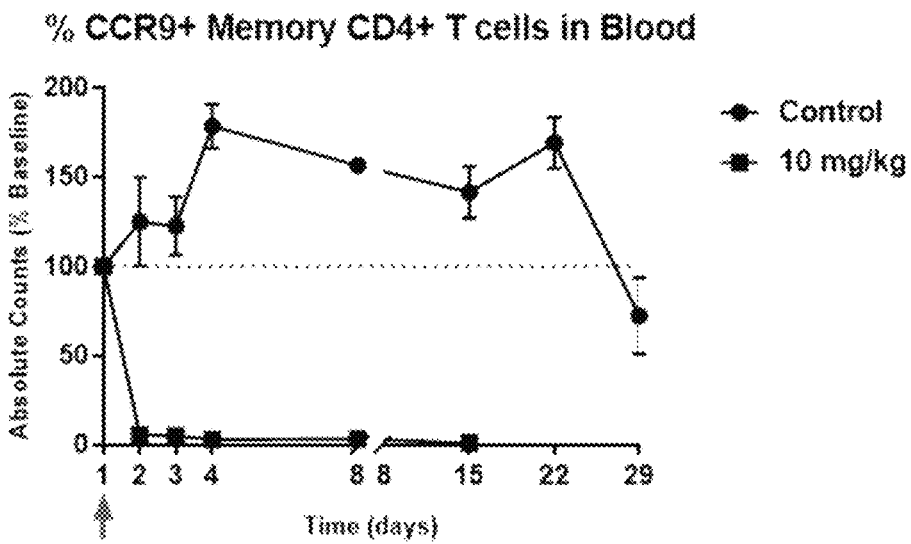
Figure 16B:
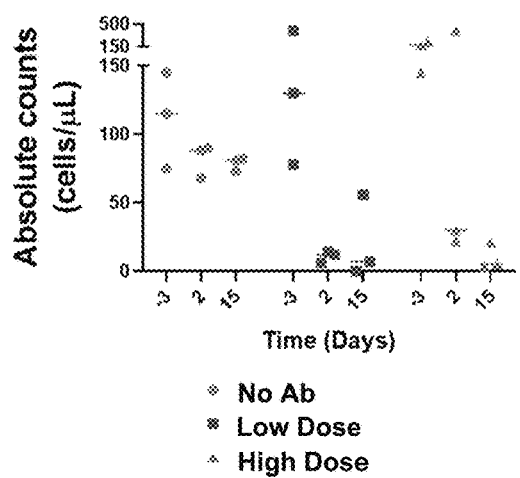
Figure 16C:
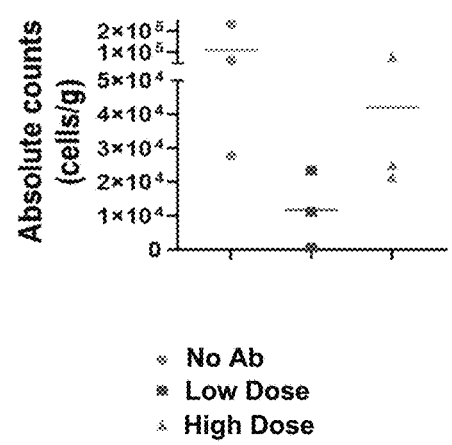
Figure 16D:
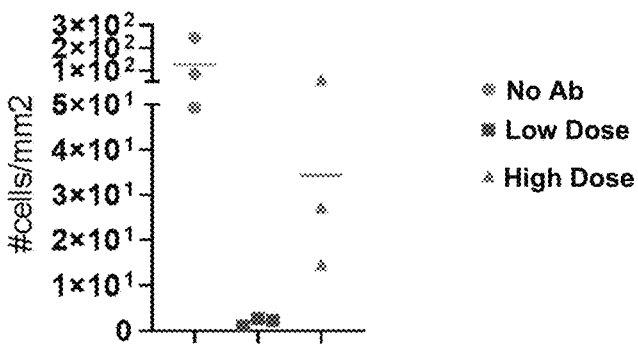

FIG. 16A: The effect of intravenous injection of 243LO0326 on the number of CCR9+ memory CD4+ T cells in the blood of cynomolgus monkeys. FIG. 16B: High and low doses of 243LO0326 decrease CDR4+CCR9+ cells in the peripheral blood of cynomolgus monkeys within 2 days. FIG. 16C: High and low doses of 243LO0326 decrease CDR4+CCR9+ cells in the illeum of cynomolgus monkeys, as measured at day 15 by FACS. FIG. 16D: High and low doses of 243LO0326 decrease CDR4+CCR9+ cells in the gut mucosa of cynomolgus monkeys, as measured at day 15 by IHC.

Figure 17:
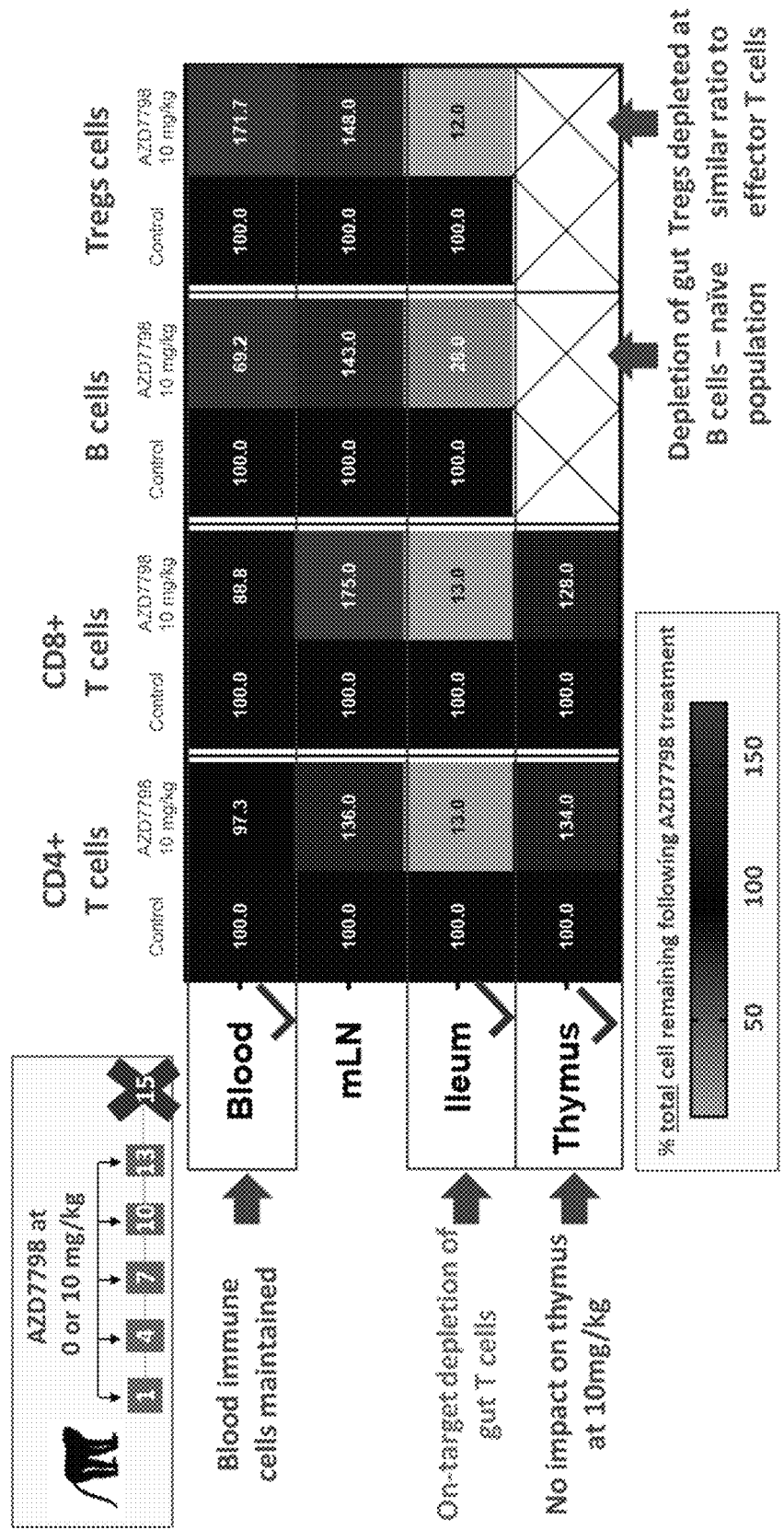

FIG. 17: Selective depletion of CCR9+ gut lymphocytes

FIG. 18A-18D: The effects of 243LO0326 on IBD markers in human gut explants taken from IBD patients.

Figure 18A:
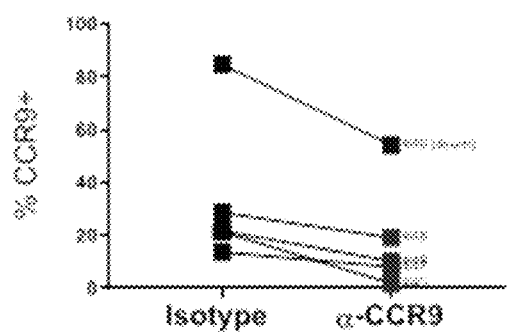
Figure 18B:
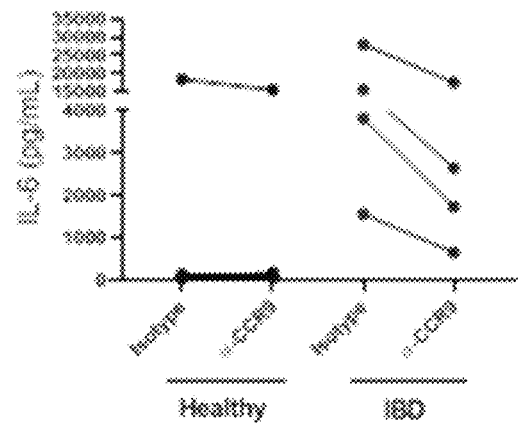
Figure 18C:
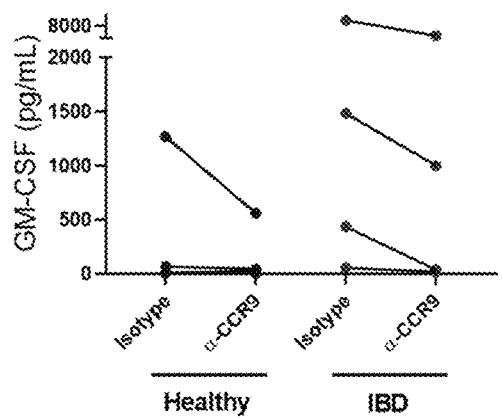
Figure 18D:
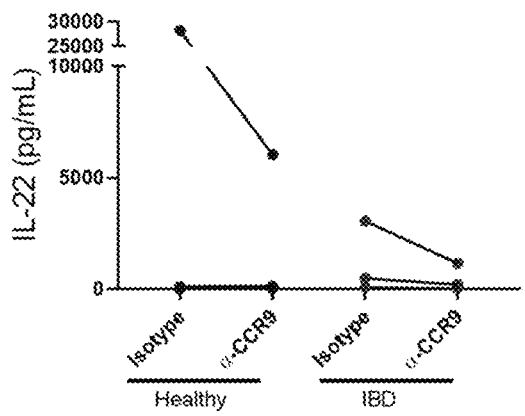

FIG. 18A: CCR9 levels; FIG. 18B: IL-6 levels; FIG. 18C: GM-CSF levels; FIG. 18D: IL-22 levels.

Figure 19:
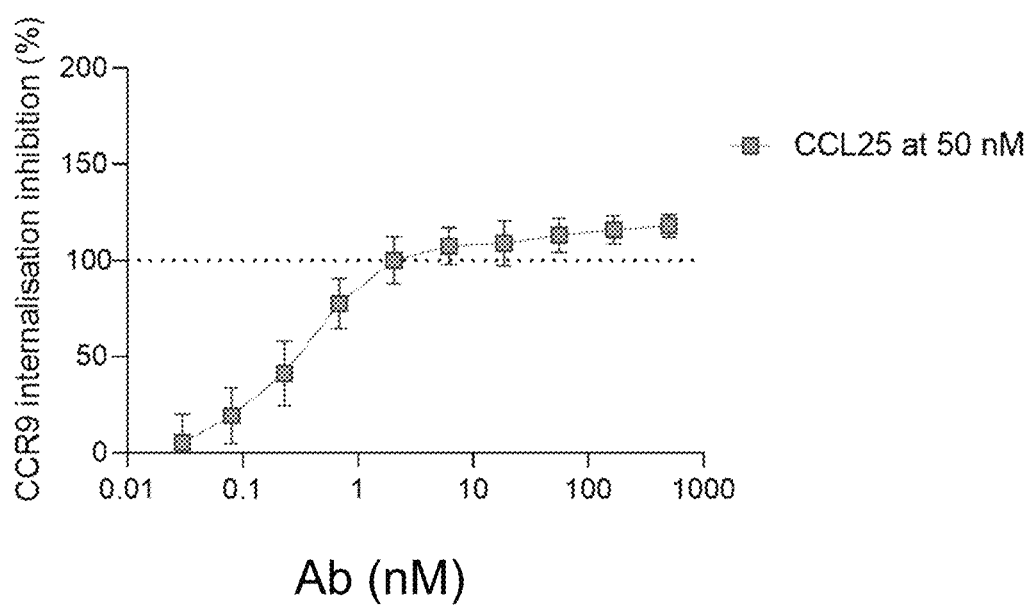

FIG. 19: Blocking CCR9 internalisation

243LO0326 inhibited CCL25 induced CCR9 internalisation.

Figure 20:
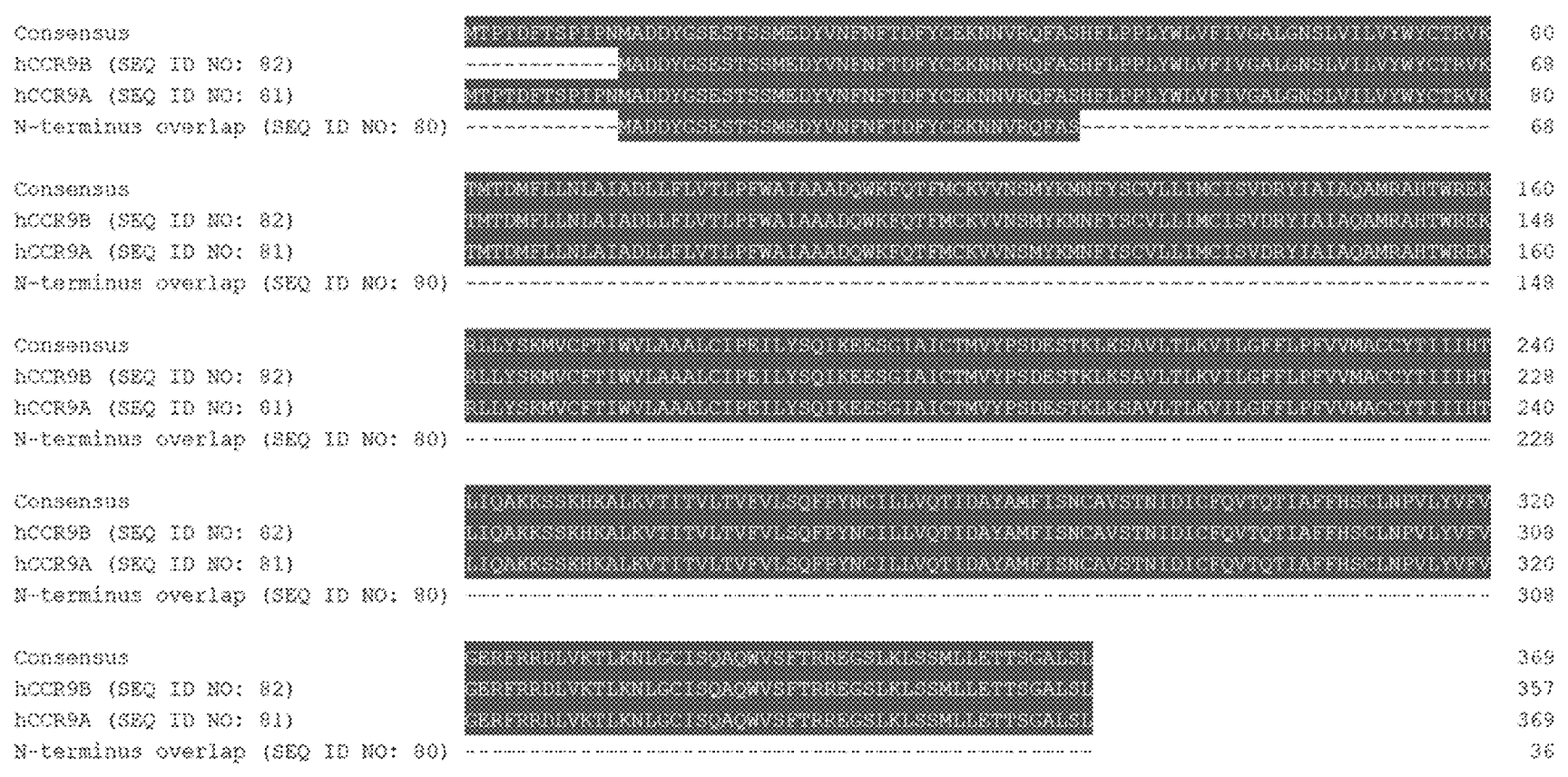

FIG. 20: CCR9A and CCR9B alignment

5 DETAILED DESCRIPTION OF THE INVENTION

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an agent" includes a plurality of such agents and reference to "the agent" includes reference to one or more agents and equivalents thereof known to those skilled in the art, and so forth.

"About" may generally mean an acceptable degree of error for the quantity measured given the nature or precision of the measurements. Exemplary degrees of error are within 20 percent (%), typically, within 10%, and more typically, within 5% of a given value or range of values. Preferably, the term "about" shall be understood herein as plus or minus (±) 5%, preferably ±4%, ±3%, ±2%, ±1%, ±0.5%, ±0.1%, of the numerical value of the number with which it is being used.

Embodiments described herein as "comprising" one or more features may also be considered as disclosure of the corresponding embodiments "consisting of" and/or "consisting essentially of" such features.

The term "pharmaceutically acceptable" as used herein means approved by a regulatory agency of the Federal or a state government, or listed in the U.S. Pharmacopeia, European Pharmacopeia or other generally recognized pharmacopeia for use in animals, and more particularly in humans.

Concentrations, amounts, volumes, percentages and other numerical values may be presented herein in a range format. It is also to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

The term "epitope" refers to a target protein region (e.g. polypeptide) capable of binding to (e.g. being bound by) a binding molecule of the invention.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

Potency of a binding molecule can be expressed as an IC50 value. IC50 is the median inhibitory concentration of a binding molecule. In functional assays, IC50 is the concentration that reduces a biological response by 50% of its maximum. IC50 can be calculated by any number of means known in the art.

Potency of a binding molecule can be expressed as an EC50 value. In functional assays, EC50 is the concentration that induces a median response between baseline and maximum after a specified exposure time. EC50 can be calculated by any number of means known in the art.

5.1 Binding Molecules

The present invention relates to binding molecules that bind to CCR9. Chemokine receptor 9, CCR9 (also known as CDw199 and GPR-9-6) is a member of the beta chemokine receptor family. CCR9 is organized into 15 domains, corresponding to an N-terminal extracellular domain (Nt), seven transmembrane domains, three intracellular domains, three extracellular domains and an intracellular C-terminal domain (Ct). In humans, CCR9 exists in two isoforms CCR9A and CCR9B. Isoform A has an additional 12 N-terminal amino acids and has higher affinity for the ligand CCL25 compared with isoform B. Isoforms A and B are reported to be co-expressed at a ratio of 10:1. Previous described anti-CCR9 antibodies 91 R and 92R only bind isoform CCR9A, and do not bind CCR9B [4].

Without wishing to be bound by theory, the present inventors' observation that a higher proportion of the CCR9 positive CD4 T lymphocytes co-expresses the proinflammatory cytokines IFN-γ, IL-4 and IL-17 in the gut compared with CCR9 negative CD4 T lymphocytes suggests that CCR9 can identify CD4 T lymphocytes that contribute to the pathogenesis of IBD.

The RNA, DNA, and amino acid sequences of CCR9 are known to those skilled in the art and can be found in many databases, for example, in the databases of the National Center for Biotechnology Information (NCBI) and UniProt. Examples of these sequences found at UniProt are at P51686-1 for human CCR9A and P51686-2 for human CCR9B; Q0H741 for cynomolgus CCR9; Q9WUT7 for mouse CCR9; and Q8CH33 for rat CCR9.

In some embodiments, the binding molecule of the invention binds to human CCR9. In some embodiments the binding molecule binds to human CCR9A and/or human CCR9B. In some embodiments, the binding molecule binds to human CCR9A and binds to human CCR9B.

In some embodiments, the binding molecule binds to CCR9 from a non-human mammalian species, such as from a non-human primate. In some embodiments, the binding molecule binds to cynomolgus CCR9. In some embodiments the binding molecule binds to human and cynomolgus CCR9, such as binding to human CCR9A and human CCR9B and cynomolgus CCR9.

In some embodiments, the binding molecule does not bind to mouse and/or rat CCR9. In some embodiments the binding molecule binds to human and cynomolgus CCR9, such as human CCR9A and human CCR9B and cynomolgus CCR9, but does not bind to mouse or rat CCR9.

In some embodiments, the binding molecule binds selectively to (also referred to interchangeably herein as specifically to) CCR9. By selective binding, it will be understood that the CDRs of a binding molecule together bind to CCR9, with no significant cross-reactivity to any other molecule. In particular a binding molecule that binds selectively to CCR9 may have no significant cross-reactivity to any other cytokine receptor. A binding molecule that binds selectively to CCR9 may have no significant cross-reactivity to any one, any two, any three or all four of CCR5, CCR8, CXCR1 and CXCR2. For example, in some embodiments, the binding molecule does not bind to CCR5, CCR8, CXCR1 or CXCR2.

In some embodiments, a binding molecule that binds selectively to human CCR9, such as human CCR9A and/or human CCR9B, may have no significant cross-reactivity with CCR9 from another species, such as with mouse and/or rat CCR9. In some embodiments a binding molecule that binds selectively to human CCR9 may have cross-reactivity with a closely related CCR9 molecule, such as cynomolgus CCR9, but may have no significant cross-reactivity with a more distantly related CCR9 such as mouse and/or rat CCR9.

Cross-reactivity may be assessed by any suitable method. For example, binding may be measured by assaying binding of the binding molecule to overexpressing cell lines expressing the receptor of interest. Binding may also be measured by a radioimmunoassay (RIA), BIACORE® (using recombinant CCR9 as the analyte and binding molecule as the ligand, or vice versa), KINEXA®, ForteBio Octet system, or other binding assays known in the art. By way of non-limiting example, cross-reactivity of binding molecule with a molecule other than CCR9 may be considered significant if the binding molecule binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to CCR9. A binding molecule that binds selectively to CCR9 may bind to another molecule, such as a different cytokine receptor, such as any one, two, three or all four of CCR5, CCR8, CXCR1, and CXCR2, at less than 90%, 85%, 80%, 75%, 70%, 65%, 60%, 55%, 50%, 45%, 40%, 35%, 30%, 25% or 20% the strength that it binds to CCR9. Preferably, the binding molecule binds to the other molecule at less than 20%, less than 15%, less than 10% or less than 5%, less than 2% or less than 1% the strength that it binds to CCR9. Where used herein, the CCR9 is preferably a naturally occurring CCR9, such as human CCR9, such as human CCR9A and/or human CCR9B.

In some embodiments, the binding molecule binds to a cell that expresses CCR9. The binding molecule may bind to a CCR9 receptor that is present in the cell membrane of a cell. The cell may be a cell that naturally expresses CCR9, or the cell may be engineered to express CCR9, such as by introducing a nucleic acid encoding CCR9 under conditions that allow for the expression of CCR9. The cell may be engineered to overexpress CCR9 such that the engineered cell line expresses higher levels of CCR9 than a corresponding un-engineered cell. The cell may express human CCR9A or human CCR9B.

The cell may be a HEK cell line that has been engineered to express CCR9, such as human CCR9A and/or human CCR9B.

The Molt 4 cell line is a human T-lymphocyte cell line from acute lymphoblastic leukemia that naturally expresses CCR9 at high levels. The Molt 4 cell line is obtainable from ATCC, CRL-1582. In some embodiments, the binding molecule binds to a Molt 4 cell. In some embodiments, the binding molecule binds to a Molt 4 cell by binding to CCR9 on the surface of said Molt 4 cell or CCR9 present in the cell membrane of said Molt 4 cell.

In some embodiments, the binding molecule does not bind to a cell that does not express CCR9, such as a Jurkat cell. The Jurkat cell line is obtainable from ATCC as Jurkat, Clone E6.1. In some embodiments, the binding molecule binds to a CCR9 (e.g., a human CCR9) with a dissociation constant (KD) of ≤1 µM, ≤100 nM, ≤10 nM, ≤5 nM, ≤1 nM, ≤0.5 nM, ≤0.1 nM, or ≤10 pM. In some embodiments, the binding molecule binds to CCR9 (e.g., CCR9 present on a Molt 4 cell) with a KD of between about 0.01 nM to about 0.45 nM, between about 0.025 nM to about 0.25 nM, or between about 0.05 nM to about 0.1 nM. In some embodiments, the binding molecule binds to CCR9 (e.g., CCR9 present on a Molt 4 cell) with a KD of about 0.09 nM.

In some embodiments, the binding molecule binds to CCR9 (e.g., CCR9 present on a Molt 4 cell) with a KD of between about 2 nM to about 5 nM, between about 2.5 nM to about 4 nM, or between about 3 nM to about 3.5 nM. In some embodiments, the binding molecule binds to CCR9 (e.g., CCR9 present on a Molt 4 cell) with a KD of about 3.4 nM.

The KD measurements (binding affinity) may be carried out by any suitable assay known in the art. Suitable assays include an affinity assay performable via a Ligand Tracer system, KinExA system (e.g., KinExA 3100, KinExA 3200, or KinExA 4000) (Sapidyne Instruments, Idaho), or ForteBio Octet system.

In some embodiments, the binding molecule is a CCR9 antagonist. For example, the binding molecule may prevent or inhibit the normal function of CCR9. For example, the binding molecule may prevent or inhibit migration of a CCR9-expressing cell by antagonising CCR9 present on the cell.

In some embodiments, the binding molecule inhibits binding of a ligand to CCR9. For example, in some embodiments, the binding molecule binds to CCR9 and blocks or inhibits the binding of a ligand to the CCR9 molecule. This may be assessed by common methods known in the art, including those described herein.

The binding molecule may be a competitive inhibitor of CCR9. For example, the binding molecule may compete with a ligand of CCR9 for binding to CCR9. Competitive binding may be assessed by common methods known in the art, including those described herein.

In some embodiments, the ligand of CCR9 is CCL25. CCL25 (also known as TECK) is a cytokine belonging to the CC chemokine family. The RNA, DNA, and amino acid sequences of CCL25 are known to those skilled in the art and can be found in many databases, for example, in the databases of the National Center for Biotechnology Information (NCBI) and UniProt. Examples of these sequences found at UniProt are at O15444 for human CCL25; O35903 for mouse CCL25; Q32PX4 for rat CCL25 and A0A2K5TSD9 and A0A2K5TSC0 for cynomolgus CCL25.

In some embodiments, the binding molecule blocks or inhibits binding of CCL25 to CCR9. For example, CCL25 may have reduced binding to CCR9 in the presence of a binding molecule of the present invention. In some embodiments, the binding molecule is capable of binding to CCR9 present on the surface or membrane of a cell and inhibiting binding of CCL25 to CCR9 on the cell.

In some embodiments, the binding molecule is capable of preventing or inhibiting migration of a CCR9-expressing cell to which it binds. For example, a cell bound by a binding molecule of the invention may migrate less efficiently in response to a stimulus than a cell not bound by a binding molecule of the invention. In some embodiments, the binding molecule prevents or inhibits migration of a CCR9-expressing cell in response to CCL25. In some embodiments, the binding molecule is capable of preventing or inhibiting migration of a CCR9-expressing cell from the periphery to the gut of a subject.

In some embodiments, the binding molecule of the invention is capable of inducing death of a CCR9-expressing cell to which it binds. For example, in some embodiments the binding molecule is capable of mediating antibody dependent cell-mediated cytotoxicity (ADCC) against a CCR9-expressing cell to which it binds. In some embodiments the binding molecule is capable of mediating antibody dependent cell-mediated cytotoxicity (ADCC) against a CCR9-expressing lymphocyte to which it binds. As used herein, "mediating antibody dependent cell-mediated cytotoxicity" or "mediating ADCC" means that the binding molecule is capable of inducing ADCC.

ADCC is a mechanism of cell-mediated immune defence whereby an immune effector cell is activated to lyse a target cell whose membrane-surface antigens have been bound by binding molecules. Examples of such immune effector cells include natural killer cells (NK cells), macrophages, neutrophils and eosinophils. Therefore, in some embodiments, the binding molecule is capable of inducing activation of such an immune effector cell. For example, a binding molecule of the invention may be capable of inducing activation of such an immune effector cell when the binding molecule is bound to a CCR9-expressing cell.

In some embodiments, the binding molecule of the invention is capable of depleting CCR9-expressing cells in a population of cells comprising CCR9-expressing cells and immune effector cells.

The ability of a binding molecule to induce death of, deplete, or mediate ADCC against a CCR9-expressing cell to which it binds can be determined using any of the methods described herein. For example, a binding molecule of the invention may be incubated with PBMCs and the percentage of CD4+CCR9+ cells remaining at the end of the incubation period determined using a non-competing CCR9 binding molecule. Varying concentrations of a binding molecule may be used to calculate a concentration-dependent killing effect of the binding molecule. From this, the EC50 of the binding molecule may be calculated. As used herein, the EC50 may be calculated based on the killing of CD4+CCR9+ cells by PBMCs after binding of a binding molecule of the invention to the CD4+CCR9+ cells.

In some embodiments, the EC50 of a binding molecule of the invention (e.g. measured as described herein) is less than 100 nM, such as less than 50 nM, less than 25 nM, less than 10 nM, or less than 5 nM. The EC50 may be less than 3 nM, less than 2 nM, less than 1 nM, less than 500 pM, or less than 250 pM. The EC50 may be from about 2 pM to about 200 pM, such as from about 3.5 pM to about 200 pM. In some embodiments, the EC50 is from about 1 pM to about 5 nM, such as from about 4 pM to about 3 nM. In some embodiments, the EC50 is from about 2 nM to about 3 nM, such as from about 2.5 nM to about 3 nM, such as about 2.6 nM. In some embodiments, the EC50 is from about 0.25 nM to about 2.5 nM, such as from about 0.5 nM to about 1 nM, such as about 0.5 nM. In some embodiments, the EC50 is from about 50 pM to about 250 pM, such as about 150 pM to about 250 pM, such as about 200 pM. In some embodiments, the EC50 is from about 3.5 pM to about 50 pM, such as from about 3.5 pM to about 25 pM. In some embodiments, the EC50 is from about 3.5 pM to about 5 pM or from about 4 pM to about 10 pM. In some embodiments, the EC50 is from about 6 pM to about 60 pM, such as from about 25 pM to about 60 pM, preferably from about 25 pM to about 35 pM such as about 30 pM.

In some embodiments, the EC50 when the binding molecule is bound to human CCR9 is from about 3.5 pM to about 10 pM, such as from about 4 pM to about 5 pM. In some embodiments, the EC50 where the binding molecule is bound to cynomolgus CCR9 is from about 6 pM to about 60 pM, such as from about 25 pM to about 60 pM, preferably from about 25 pM to about 35 pM such as about 30 pM.

To initiate ADCC, binding molecules can cross-link an immune effector cell to a CCR9-expressing cell. Thus, in some embodiments, the binding molecules of the invention are capable of cross-linking an immune effector cell to a CCR9-expressing cell. For example, binding molecules may be capable of cross-linking an immune effector cell to a CCR9-expressing cell by binding an Fc receptor on an immune effector cell. There are a number of Fc receptors that are specific for different classes of antibody, including IgG (gamma receptors), IgE (eta receptors), IgA (alpha receptors) and IgM (mu receptors). Therefore, in some embodiments, the binding molecule is capable of binding to an Fc receptor. In some embodiments, the binding molecule is capable of binding to an FcγR, such as a receptor selected from FcγRI, FcγRIIa, FcγRIIb, FcγRIIIa, and FcγRIIIb. In some embodiments, the binding molecule is capable of binding to FcγRIIIa. In some embodiments, the binding molecule is capable of binding to an Fc receptor that is present on an immune effector cell.

Binding molecules can be bound by an Fc receptor on an immune effector cell via an Fc domain present in the binding molecule. Therefore, in some embodiments a binding molecule of the invention comprises a region that is capable of binding to an Fc receptor, such as an Fc receptor as defined above. In some embodiments, the binding molecule comprises an immunoglobulin Fc domain, or a fragment thereof that retains the ability to bind to one or more Fc receptors, such as one or more Fc receptors as defined above. As used herein, the term "Fc domain" refers to the portion of a single immunoglobulin heavy chain beginning in the hinge region and ending at the C-terminus of the antibody. Accordingly, a complete Fc domain may comprise at least a portion of a hinge (e.g. upper, middle, and/or lower hinge region) domain, a CH2 domain, and a CH3 domain. In some embodiments, the binding molecule comprises a homodimer of an Fc domain. In some embodiments, the binding molecule comprises a region that binds to CCR9, and further comprises such an immunoglobulin Fc domain or fragment thereof. In some embodiments, the binding molecule is an immunoglobulin molecule or fragment thereof, which comprises an antigen-binding region that binds CCR9, and an Fc-binding region that binds to one or more Fc receptors as defined above.

In some embodiments, the Fc-binding region, immunoglobulin Fc domain, or fragment thereof is an IgG Fc domain or fragment thereof, such as an IgG1, IgG2, IgG3 or IgG4 Fc domain or fragment thereof. In some embodiments, the Fc-binding region, immunoglobulin Fc domain or fragment thereof is an IgG1 Fc domain or fragment thereof. In some embodiments, the Fc-binding region, immunoglobulin Fc domain or fragment thereof is a human immunoglobulin Fc domain or fragment thereof, such as a human IgG1 Fc domain or fragment thereof. In some embodiments, the binding molecule comprises an immunoglobulin Fc domain having an amino acid sequence set forth in SEQ ID NO: 78. For example, in some embodiments the Fc domain comprises amino acids 111-330 of SEQ ID NO: 78.

Binding of a binding molecule of the invention to an Fc receptor on an immune effector cell can cross-link the immune effector cell with a cell to which the antigen-binding portion of the binding molecule is bound. Thus, in some embodiments, the binding molecule of the invention is capable of inducing immune effector cell activation. In some embodiments, cross-linking of an immune effector cell to a CCR9-expressing cell by the binding molecule activates ADCC by the effector cell.

Immune effector cell activation may be assessed by the methods described herein such as by an in vitro ADCC bioassay. Briefly, immune effector cells may be modified to express a reporter, such as a luciferase reporter, which acts as a surrogate for effector function. Immune effector cells comprising such a reporter are added to target cells which have been pre-incubated with a binding molecule. After incubation of the effector and target cells, reporter function (e.g. luminescence) is quantified. Such a method may thus be used to identify a binding molecule that is capable of activating an immune effector cell. For example, if the assay is intended to assess the effectiveness of a binding molecule to activate immune effector cells, the target cell may be a cell that is known to express CCR9. Such a method may be used to identify a target cell that expresses CCR9. For example, if the assay is intended to assess whether a target cell expresses CCR9, then the binding molecule may be a binding molecule that is known to bind to CCR9, such as a binding molecule of the invention.

In some embodiments, the binding molecule of the invention has an NK cell activation potency of ≤5 nM, such as ≤3 nM, ≤2 nM, ≤1 nM or ≤0.5 nM as determined using a HEK cell line expressing CCR9A. In some embodiments, the binding molecule of the invention has an NK cell activation potency of 0.8 nM as determined using a Molt 4 cell line. In some embodiments, the activation of antibody dependent cell-mediated cytotoxicity by the effector cell causes lysis of the CCR9-expressing cell.

For a binding molecule to be considered capable of mediating ADCC against a CCR9-expressing cell to which it binds, the binding molecule should have an immune effector cell activation potency, such as a NK cell activation potency, of (≤20 nM as determined using a Molt 4 cell line, or ≤30 nM as determined using a HEK cell line expressing CCR9A and/or a PBMC killing EC50 of ≤3 nM.

In some embodiments, a binding molecule of the invention provides for altered effector functions that, in turn, affect the biological profile of the binding molecule. For example, alteration of the glycosylation profile of a constant region domain of an immunoglobulin molecule can increase Fc receptor binding of the modified binding molecule. In other cases constant region modifications, consistent with this invention, may moderate complement binding. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well-known biochemical or molecular engineering techniques well within the purview of the skilled artisan.

Therefore, in some embodiments, a binding molecule of the invention may have enhanced effector functions that increase the ability of the binding molecule to interact with an immune effector cell, such as that increase the ability of the binding molecule to cross-link an immune effector cell with a CCR9-expressing cell that is bound by the binding molecule, or that increase the ability opt the binding molecule to induce ADCC. In some embodiments, the immunoglobulin Fc domain of a binding molecule provided herein is modified compared to the corresponding wild-type Fc domain, wherein said modification leads to an increased affinity for one or more Fc receptors, preferably one or more Fcγ receptors. In some embodiments, the immunoglobulin Fc domain is modified compared to the corresponding wild-type Fc domain, wherein said modification leads to an enhanced antibody dependent cell-mediated cytotoxicity response.

A binding molecule can be made that has an altered type of glycosylation, such as an afucosylated/hypofucosylated binding molecule having reduced amounts of fucosyl residues or a binding molecule having increased bisecting GlcNac structures. Such altered glycosylation profiles have been demonstrated to increase the ADCC ability of binding molecules. These modifications can be accomplished by any known means in the art such as those described in the Examples section herein.

Therefore, in some embodiments, a binding molecule provided herein may be afucosylated. The binding molecule may comprise no fucose. The binding molecule may include at least one N-linked glycan which lacks a core fucose sugar unit.

In some embodiments, the binding molecule is afucosylated at EU position 297, also referred to herein as position N297 (Edelman et al., 1969, Proc Natl Acad Sci USA 63(1): 78-85). That is, the N-linked glycan at position N297 may be absent, may lack fucose, or may lack a core fucose sugar unit. The N-linked glycan at amino acid position N297 corresponds to position N180 in SEQ ID NO: 78. In some embodiments, the binding molecule comprises SEQ ID NO: 78 wherein N180 of SEQ ID NO: 78 is afucosylated. In some embodiments, the binding molecule comprises an Fc domain comprising amino acids 111-330 of SEQ ID NO: 78 wherein N180 of SEQ ID NO: 78 is afucosylated.

As described herein, the binding molecule may comprise an Fc domain or a fragment thereof, such as an hIgG1 Fc domain or a fragment thereof. In some embodiments, the binding molecule comprises an afucosylated Fc domain or fragment thereof, such as an afucosylated hIgG1 Fc domain or fragment thereof. Any of the Fc domains or Fc domain fragments as described herein may be present in an afucosylated form. The Fc domain or fragment may comprise no fucose. At least one N-linked glycan of the Fc domain or fragment may lack a core fucose sugar unit. The Fc domain or fragment may be afucosylated at EU position 297. In some embodiments, the binding molecule comprises an afucosylated Fc domain comprising amino acids 111-330 of SEQ ID NO: 78. For example, the binding molecule may comprise an afucosylated Fc domain comprising amino acids 111-330 of SEQ ID NO: 78 wherein N180 of SEQ ID NO: 78 is afucosylated. In some embodiments, the binding molecule comprises an afucosylated Fc domain and a non-afucosylated Fc domain. For example, the binding molecule may comprise an afucosylated Fc domain comprising amino acids 111-330 of SEQ ID NO: 78, wherein N180 of SEQ ID NO: 78 is afucosylated, and a non-afucosylated Fc domain comprising amino acids 111-330 of SEQ ID NO: 78. In some embodiments, the binding molecule is fully afucosylated. For example, all of the N-linked glycans of the binding molecule may be afucosylated. In some embodiments, the Fc domain of the binding molecule is fully afucosylated. For example, all of the N-linked glycans of the Fc domain may be afucosylated.

In some embodiments, the binding molecule is present in a composition comprising multiple copies of said binding molecule, wherein at least 50%, 75%, 90%, 95%, 98%, 99% or 100% of the copies of the binding molecule in the composition are afucosylated, e.g. lacking fucose, lacking a core fucose sugar unit in at least one N-linked glycan, or afucosylated at EU position 297, as described herein. In such a composition, the binding molecule has an amino acid sequence as disclosed herein, but the copies of the binding molecule in the composition may vary in their glycosylation pattern, e.g. some copies may comprise fucose and some copies may lack fucose, e.g. lacking a core fucose sugar unit in at least one N-linked glycan, or being afucosylated at EU position 297, as described herein.

In any of the embodiments disclosed herein, the CCR9-expressing cell is a gut-resident cell. In any of the embodiments disclosed herein, the CCR9-expressing cell is a peripheral blood cell. In any of the embodiments disclosed herein, the CCR9-expressing cell expresses CD4, CD8, CD20, CD19, CD69 and/or CD103. In any of the embodiments disclosed herein, the CCR9-expressing cell expresses GM-CSF, IL-22, TNFα, IL-6, IFNγ, IL-4 and/or IL-17. For example, the CCR9-expressing cell may express IFNγ, IL-4 and/or IL-17. In any of the embodiments disclosed herein, the CCR9-expressing cell is a lymphocyte, e.g. a gut-resident lymphocyte or a peripheral blood lymphocyte. In some embodiments, the lymphocyte is a T-lymphocyte such as a CD4+ T-lymphocyte. In some embodiments, the lymphocyte is a B-lymphocyte.

In any of the embodiments disclosed herein, the immune effector cell is a NK cell, a macrophage, a neutrophil, an eosinophil or a combination thereof. In any of the embodiments disclosed herein, the immune effector cell is a NK cell.

A binding molecule of the invention may have any one or more of the functional characteristics set out above. Additionally or alternatively, it may have any one or more of the structural (e.g. sequence) characteristics set out below.

FIG. 3 and FIG. 4 illustrate sequences from exemplified binding molecules of the invention. The binding molecules illustrated in FIG. 3 and FIG. 4 are antibodies, where the antibodies comprise a variable heavy domain (VH) and variable light domain (VL) region sequence as illustrated in these Figures. The binding molecule of the invention may comprise a VH and VL of any antibody illustrated in FIG. 3 or FIG. 4. The binding molecule of the invention may comprise a VH and VL of any antibody illustrated in FIG. 4.

Table 3 provides the amino acid sequences of the VH and VL regions, and Table 4 provides CDR sequences, for exemplary binding molecules of the invention. The binding molecule of the invention may comprise the VH and VL of any binding molecule illustrated in Table 3. The binding molecule of the invention may comprise a set of six CDRs (HCDR1, HCDR2, HCDR3, LCDR1, LCDR2, and LCDR3) of any binding molecule illustrated in Table 4.

A binding molecule of the invention may comprise the CDR sequences of any antibody as shown in FIG. 3 or FIG. 4. For example, a binding molecule may comprise all six of the HCDR1, HCDR2, HCDR3, LCDR1, LCDR2 and LCDR3 sequences as indicated for any one of the antibodies illustrated in FIG. 3 or FIG. 4. A binding molecule of the invention may comprise the CDR sequences of any antibody as shown in FIG. 4. For example, a binding molecule may comprise all six of the HCDR1, HCDR2, HCDR3, LCDR1, LCDR2 and LCDR3 sequences as indicated for any one of the antibodies illustrated in FIG. 4. A binding molecule of the invention may comprise a set of six CDRs as illustrated in Table 4. For example, a binding molecule may comprise all six of the HCDR1, HCDR2, HCDR3, LCDR1, LCDR2 and LCDR3 sequences as indicated for any one of the antibodies illustrated in Table 4.

A binding molecule of the invention may comprise a heavy chain variable (VH) region having a set of CDRs HCDR1, HCDR2 and HCDR3 and a light chain variable (VL) region having a set of CDRs LCDR1, LCDR2 and LCDR3. Thus, the binding molecule may comprise a heavy chain variable region (VH) which comprises HCDR1, HCDR2, HCDR3 as indicated for any one of the antibodies illustrated in FIG. 3 or FIG. 4, and a light chain variable region (VL) which comprises LCDR1, LCDR2 and LCDR3 as indicated for the same antibody illustrated in FIG. 3 or FIG. 4. The binding molecule may comprise a heavy chain variable region (VH) which comprises HCDR1, HCDR2, HCDR3 as indicated for any one of the antibodies illustrated in FIG. 4, and a light chain variable region (VL) which comprises LCDR1, LCDR2 and LCDR3 as indicated for the same antibody illustrated in FIG. 4. The binding molecule may comprise a heavy chain variable region (VH) which comprises HCDR1, HCDR2, HCDR3 as indicated for any one of the antibodies illustrated in Table 4, and a light chain variable region (VL) which comprises LCDR1, LCDR2 and LCDR3 as indicated for the same antibody illustrated in Table 4.

For example, in some embodiments, the binding molecule comprises:
a) HCDR1 of SEQ ID NO: 1, HCDR2 of SEQ ID NO: 2, HCDR3 of SEQ ID NO: 3, LCDR1 of SEQ ID NO: 4, LCDR2 of SEQ ID NO: 5 and LCDR3 of SEQ ID NO: 6 wherein $X_1$ and $X_2$ of SEQ ID NO: 4 are any amino acid;
b) HCDR1 of SEQ ID NO: 7, HCDR2 of SEQ ID NO: 8, HCDR3 of SEQ ID NO: 9, LCDR1 of SEQ ID NO: 10, LCDR2 of SEQ ID NO: 11 and LCDR3 of SEQ ID NO: 12; or
c) HCDR1 of SEQ ID NO: 13, HCDR2 of SEQ ID NO: 14, HCDR3 of SEQ ID NO: 15, LCDR1 of SEQ ID NO: 16, LCDR2 of SEQ ID NO: 17 and LCDR3 of SEQ ID NO: 18.

In some embodiments, the binding molecule comprises:
a) a VH region comprising HCDR1 of SEQ ID NO: 1, HCDR2 of SEQ ID NO: 2 and HCDR3 of SEQ ID NO: 3, and a VL region comprising LCDR1 of SEQ ID NO: 4, LCDR2 of SEQ ID NO: 5 and LCDR3 of SEQ ID NO: 6 wherein $X_1$ and $X_2$ of SEQ ID NO: 4 are any amino acid;
b) a VH region comprising HCDR1 of SEQ ID NO: 7, HCDR2 of SEQ ID NO: 8 and HCDR3 of SEQ ID NO: 9, and a VL region comprising LCDR1 of SEQ ID NO: 10, LCDR2 of SEQ ID NO: 11 and LCDR3 of SEQ ID NO: 12; or
c) a VH region comprising HCDR1 of SEQ ID NO: 13, HCDR2 of SEQ ID NO: 14 and HCDR3 of SEQ ID NO: 15, and a VL region comprising LCDR1 of SEQ ID NO: 16, LCDR2 of SEQ ID NO: 17 and LCDR3 of SEQ ID NO: 18.

The binding molecule may comprise HCDR1 of SEQ ID NO: 1, HCDR2 of SEQ ID NO: 2, HCDR3 of SEQ ID NO: 3, LCDR2 of SEQ ID NO: 5, LCDR3 of SEQ ID NO: 6 and LCDR1 having an amino acid sequence selected from: (a) SEQ ID NO: 4; (b) SEQ ID NO: 19; (c) SEQ ID NO: 20; (d) SEQ ID NO: 21; and (e) SEQ ID NO: 22 wherein $X_1$ and $X_2$ of SEQ ID NO: 4 are any amino acid, and wherein $X_1$ of SEQ ID NO: 19 is P or S and $X_2$ of SEQ ID NO: 19 is R, T or G. Accordingly, in some embodiments, the binding molecule comprises:
a) HCDR1 of SEQ ID NO: 1, HCDR2 of SEQ ID NO: 2, HCDR3 of SEQ ID NO: 3, LCDR1 of SEQ ID NO: 4, LCDR2 of SEQ ID NO: 5, and LCDR3 of SEQ ID NO: 6 wherein $X_1$ and $X_2$ of SEQ ID NO: 4 are any amino acid;
b) HCDR1 of SEQ ID NO: 1, HCDR2 of SEQ ID NO: 2, HCDR3 of SEQ ID NO: 3, LCDR1 of SEQ ID NO: 19, LCDR2 of SEQ ID NO: 5, and LCDR3 of SEQ ID NO: 6 wherein $X_1$ of SEQ ID NO: 19 is P or S and $X_2$ of SEQ ID NO: 19 is R, T or G;
c) HCDR1 of SEQ ID NO: 1, HCDR2 of SEQ ID NO: 2, HCDR3 of SEQ ID NO: 3, LCDR1 of SEQ ID NO: 20, LCDR2 of SEQ ID NO: 5, and LCDR3 of SEQ ID NO: 6;
d) HCDR1 of SEQ ID NO: 1, HCDR2 of SEQ ID NO: 2, HCDR3 of SEQ ID NO: 3, LCDR1 of SEQ ID NO: 21, LCDR2 of SEQ ID NO: 5, and LCDR3 of SEQ ID NO: 6; or
e) HCDR1 of SEQ ID NO: 1, HCDR2 of SEQ ID NO: 2, HCDR3 of SEQ ID NO: 3, LCDR1 of SEQ ID NO: 22, LCDR2 of SEQ ID NO: 5, and LCDR3 of SEQ ID NO: 6.

In some embodiments, the binding molecule comprises:
a) a VH region comprising HCDR1 of SEQ ID NO: 1, HCDR2 of SEQ ID NO: 2, and HCDR3 of SEQ ID NO: 3, and a VL region comprising LCDR1 of SEQ ID NO: 4, LCDR2 of SEQ ID NO: 5, and LCDR3 of SEQ ID NO: 6 wherein $X_1$ and $X_2$ of SEQ ID NO: 4 are any amino acid;
b) a VH region comprising HCDR1 of SEQ ID NO: 1, HCDR2 of SEQ ID NO: 2, and HCDR3 of SEQ ID NO: 3, and a VL region comprising LCDR1 of SEQ ID NO: 19, LCDR2 of SEQ ID NO: 5, and LCDR3 of SEQ ID NO: 6 wherein $X_1$ of SEQ ID NO: 19 is P or S and $X_2$ of SEQ ID NO: 19 is R, T or G;
c) a VH region comprising HCDR1 of SEQ ID NO: 1, HCDR2 of SEQ ID NO: 2, and HCDR3 of SEQ ID NO: 3, and a VL region comprising LCDR1 of SEQ ID NO: 20, LCDR2 of SEQ ID NO: 5, and LCDR3 of SEQ ID NO: 6;
d) a VH region comprising HCDR1 of SEQ ID NO: 1, HCDR2 of SEQ ID NO: 2, and HCDR3 of SEQ ID NO: 3, and a VL region comprising LCDR1 of SEQ ID NO: 21, LCDR2 of SEQ ID NO: 5, and LCDR3 of SEQ ID NO: 6; or
e) a VH region comprising HCDR1 of SEQ ID NO: 1, HCDR2 of SEQ ID NO: 2, and HCDR3 of SEQ ID NO: 3, and a VL region comprising LCDR1 of SEQ ID NO: 22, LCDR2 of SEQ ID NO: 5, and LCDR3 of SEQ ID NO: 6.

The present invention encompasses the binding molecules defined herein having the recited CDR sequences (reference binding molecules), as well as functional variants thereof. A functional variant binds to the same target antigen as the reference binding molecule, and preferably exhibits the same antigen cross-reactivity profile as the reference binding molecule. For example, the functional variant may bind to the same naturally occurring forms of CCR9 as the reference binding molecule, such as binding to the same subset of molecules from the following list: human CCR9A, human CCR9B, cynomolgus CCR9, rat CCR9 and mouse CCR9. The functional variants may have a different affinity for a target antigen when compared to the reference binding molecule, but substantially the same affinity is preferred.

In some embodiments, functional variants of a reference binding molecule show sequence variation at one or more CDRs when compared to corresponding reference CDR sequences. Thus, a functional binding molecule variant may comprise a functional variant of a CDR. Where the term "functional variant" is used in the context of a CDR sequence, this means that the CDR has 1, 2 or 3 amino acid differences when compared to a corresponding reference CDR sequence, and when combined with the remaining 5 CDRs (or variants thereof) enables the variant binding molecule to bind to the same target antigen as the reference binding molecule, and preferably to exhibit the same antigen cross-reactivity profile as the reference binding molecule.

In some embodiments a binding molecule comprises: a light chain CDR1 having 1, 2 or 3 amino acid differences when compared to a corresponding reference CDR sequence; a light chain CDR2 having 1, 2 or 3 amino acid differences when compared to a corresponding reference CDR sequence; a light chain CDR3 having 1, 2 or 3 amino acid differences when compared to a corresponding reference CDR sequence; a heavy chain CDR1 having 1, 2 or 3 amino acid differences when compared to a corresponding reference CDR sequence; a heavy chain CDR2 having 1, 2 or 3 amino acid differences when compared to a corresponding reference CDR sequence; and a heavy chain CDR3 having 1, 2 or 3 amino acid differences when compared to a corresponding reference CDR sequence; wherein the binding molecule binds to the same target antigen as the reference binding molecule, and preferably exhibits the same antigen cross-reactivity as the reference binding molecule.

In some embodiments a binding molecule comprises: a light chain CDR1 having at most 2 amino acid differences when compared to a corresponding reference CDR sequence; a light chain CDR2 having at most 2 amino acid differences when compared to a corresponding reference CDR sequence; a light chain CDR3 having at most 2 amino acid differences when compared to a corresponding reference CDR sequence; a heavy chain CDR1 having at most 2 amino acid differences when compared to a corresponding reference CDR sequence; a heavy chain CDR2 having at most 2 amino acid differences when compared to a corresponding reference CDR sequence; and a heavy chain CDR3 having at most 2 amino acid differences when compared to a corresponding reference CDR sequence; wherein the binding molecule binds to the same target antigen as the reference binding molecule, and preferably exhibits the same antigen cross-reactivity profile as the reference binding molecule. In some embodiments, a binding molecule comprises a light chain CDR1 having at most 2 amino acid differences when compared to a corresponding reference CDR sequence.

A binding molecule may comprise: a light chain CDR1 having at most 1 amino acid difference when compared to a corresponding reference CDR sequence; a light chain CDR2 having at most 1 amino acid difference when compared to a corresponding reference CDR sequence; a light chain CDR3 having at most 1 amino acid difference when compared to a corresponding reference CDR sequence; a heavy chain CDR1 having at most 1 amino acid difference when compared to a corresponding reference CDR sequence; a heavy chain CDR2 having at most 1 amino acid difference when compared to a corresponding reference CDR sequence; and a heavy chain CDR3 having at most 1 amino acid difference when compared to a corresponding reference CDR sequence; wherein the binding molecule binds to the same target antigen as the reference binding molecule, and preferably exhibits the same antigen cross-reactivity profile as the reference binding molecule.

In some embodiments, a variant binding molecule may have at most 5, 4 or 3 amino acid differences total in the CDRs thereof when compared to a corresponding reference binding molecule, with the proviso that there are at most 3, at most 2 or at most 1 amino acid differences per CDR. Preferably a variant binding molecule has at most 2 (more preferably at most 1) amino acid differences total in the CDRs thereof when compared to a corresponding reference binding molecule, with the proviso that there are at most 2 amino acid differences per CDR. More preferably a variant binding molecule has at most 2 (more preferably at most 1) amino acid differences total in the CDRs thereof when compared to a corresponding reference binding molecule, with the proviso that there is at most 1 amino acid difference per CDR.

For example, such a binding molecule may comprise all six of the HCDR1, HCDR2, HCDR3, LCDR1, LCDR2 and LCDR3 sequences of a reference binding molecule (such as any one of the antibodies illustrated in FIG. 3 or FIG. 4 or Table 3), wherein any one or more of said HCDR1, HCDR2, HCDR3, LCDR1, LCDR2 and LCDR3 sequences comprises 1, 2 or 3 amino acid changes, compared to the respective CDR sequences of the reference binding molecule. A binding molecule may comprise all six of the HCDR1, HCDR2, HCDR3, LCDR1, LCDR2 and LCDR3 sequences of a reference binding molecule (such as any one of the antibodies illustrated in FIG. 3 or FIG. 4), except for having 1, 2 or 3 amino acid changes, e.g. substitutions, in any one of said CDR sequences. The binding molecule may comprise 1, 2 or 3 amino acid changes, e.g. substitutions, in any one or more of said light chain CDRs and/or any one or more of said heavy chain CDRs. The binding molecule may comprise 1, 2 or 3 amino acid changes, e.g. substitutions, in any one or more of HCDR1, HCDR2, LCDR1, LCDR2 and LCDR3. The binding molecule may comprise 1, 2 or 3 amino acid changes, e.g. substitutions, in LCDR1.

The foregoing can be applied to any of the antibodies illustrated in FIG. 3 or FIG. 4, or Table 4, or to any of the binding molecules described herein, wherein the amino acid differences are defined relative to the CDR sequences thereof, and wherein the variant binding molecule binds to the same target antigen as said binding molecules, and preferably exhibits the same antigen cross-reactivity. Thus, the reference binding molecule in any of the embodiments herein may be an antibody having a VH and VL sequences of any of the antibodies illustrated in FIG. 3 or FIG. 4 or binding molecules of Table 3, or an antibody having the set of six CDRs of any of the antibodies illustrated in FIG. 3 or FIG. 4 or Table 4.

The amino acid difference may be an amino acid substitution, insertion or deletion. In some embodiments the amino acid difference is a conservative amino acid substitution as described herein.

In some embodiments, the binding molecule comprises all six of the HCDR1, HCDR2, HCDR3, LCDR1, LCDR2 and LCDR3 sequences as indicated for any one of the antibodies illustrated in FIG. 3 or FIG. 4, or Table 4 or as indicated above, or a functional variant of any thereof. For example, such a binding molecule may comprise all six of the HCDR1, HCDR2, HCDR3, LCDR1, LCDR2 and LCDR3 sequences as indicated for any one of the antibodies illustrated in FIG. 3 or FIG. 4 or Table 4 or as indicated above, wherein any one or more of said HCDR1, HCDR2, HCDR3, LCDR1, LCDR2 and LCDR3 sequences comprises 1, 2 or 3 amino acid changes, e.g. substitutions, compared to the respective sequences as recited in FIG. 3 or FIG. 4 or Table 4 or above. A binding molecule may comprise all six of the HCDR1, HCDR2, HCDR3, LCDR1, LCDR2 and LCDR3 sequences as indicated for any one of the antibodies illustrated in FIG. 3 or FIG. 4 or binding molecules of Table 3 or as indicated above, except for having 1, 2 or 3 amino acid changes, e.g. substitutions, in any one of said CDR sequences. The binding molecule may comprise 1, 2 or 3 amino acid changes, e.g. substitutions, in any one or more of said light chain CDRs and/or any one or more of said heavy chain CDRs. The binding molecule may comprise 1, 2 or 3 amino acid changes, e.g. substitutions, in any one or more of HCDR1, HCDR2, LCDR1, LCDR2 and LCDR3. The binding molecule may comprise 1, 2 or 3 amino acid changes, e.g. substitutions, in LCDR1.

A binding molecule of the invention may comprise the heavy chain variable region (VH) and the light chain variable region (VL) of any antibody as shown in FIG. 3 or FIG. 4 or binding molecule of Table 3.

For example, in some embodiments, the binding molecule comprises:
- a) a VH region amino acid sequence comprising SEQ ID NO: 51 and a VL region amino acid sequence comprising SEQ ID NO: 52;
- b) a VH region amino acid sequence comprising SEQ ID NO: 51 and a VL region amino acid sequence comprising SEQ ID NO: 53;
- c) a VH region amino acid sequence comprising SEQ ID NO: 51 and the VL region amino acid sequence comprising SEQ ID NO: 54;
- d) a VH region amino acid sequence comprising SEQ ID NO: 51 and a VL region amino acid sequence comprising SEQ ID NO: 55 (DVVMTQTPLSLPVSLGDQASISCRSSQSLVHX$_1$NX$_2$NTYLHWYLQKPGQSPKLLIYKVSNRFSGVPDRFSGSGSGTDFTLKISRVEAEDLGVFFCSQSTHVPWTFGGGTKLEIK wherein (a) X$_1$ and X$_2$ are each any amino acid (SEQ ID NO: 76); or (b) X$_1$ is P or S and X$_2$ is R, T or G (SEQ ID NO: 77)); or
- e) a VH region amino acid sequence comprising SEQ ID NO: 56 and a VL region amino acid sequence comprising SEQ ID NO: 57.

In some embodiments, the binding molecule comprises:
- a) a VH region amino acid sequence comprising SEQ ID NO: 58 and a VL region amino acid sequence comprising SEQ ID NO: 59; or
- b) a VH region amino acid sequence comprising SEQ ID NO: 60 and a VL region amino acid sequence comprising SEQ ID NO: 61.

The present invention encompasses binding molecules as described herein comprising the recited VH and VL region sequences (reference binding molecules), as well as functional variants thereof. A functional variant binds to the same target antigen as the reference binding molecule, and preferably exhibits the same antigen cross-reactivity as the reference binding molecule. The functional variants may have a different affinity for the target antigen when compared to the reference binding molecule, but substantially the same affinity is preferred.

The VH region sequence of a binding molecule may have at least 80%, at least 85%, at least 90%, at least 95%, at least 98% or at least 99% sequence identity to the corresponding VH region sequence of a reference binding molecule. The VL region sequence of a binding molecule may have at least 80%, at least 85%, at least 90%, at least 95%, at least 98% or at least 99% sequence identity to the corresponding VL region sequence of a reference binding molecule.

In some embodiments, the CDRs of such a binding molecule are identical to the CDRs of the reference binding molecule, and the differences all lie outside those CDRs, e.g. the differences between the binding molecule and the reference binding molecule are in the framework regions of the VH and/or VL sequences.

In some embodiments, the CDRs of such a binding molecule are functional variants, as described above. In some embodiments, such a binding molecule comprises amino acid differences in one or more CDRs and amino acid differences in one or more framework regions compared with the VH and/or VL sequences of the corresponding reference binding molecule.

In some embodiments a binding molecule has the same framework sequences as the reference binding molecules. In another embodiment the binding molecule comprises a framework region having at most 2, preferably at most 1 amino acid difference (when compared to a corresponding reference framework sequence). Thus, each framework region may have at most 2, preferably at most 1 amino acid difference (when compared to a corresponding reference framework sequence).

In some embodiments a binding molecule may have at most 5, 4 or 3 amino acid differences total in the framework regions thereof when compared to a corresponding reference binding molecule, with the proviso that there is at most 2 (preferably at most 1) amino acid differences per framework region. Such a binding molecule may have at most 2 (more preferably at most 1) amino acid differences total in the framework regions thereof when compared to a corresponding reference binding molecule, with the proviso that there is at most 2 amino acid differences per framework region. Such a binding molecule may have at most 2 (more preferably at most 1) amino acid differences total in the framework regions thereof when compared to a corresponding reference binding molecule, with the proviso that there is at most 1 amino acid difference per framework region.

Thus, a binding molecule may comprise a VH region and a VL region as described herein, wherein: the VH region has at most 14 amino acid differences (at most 2 amino acid differences in each CDR and at most 2 amino acid differences in each framework region) when compared to the VH region of a reference binding molecule herein; and the VL region has at most 14 amino acid differences (at most 2 amino acid differences in each CDR and at most 2 amino acid differences in each framework region) when compared to the VL region of a reference binding molecule herein; wherein the variant binding molecule binds to the same target antigen as the reference binding molecule, and preferably exhibits the same antigen cross-reactivity as the reference binding molecule.

Said variant VH or VL regions may be referred to as "functional equivalents" of the reference VH or VL regions.

In some embodiments a binding molecule may comprise a VH region and a VL region as described herein, wherein: the VH region has at most 7 amino acid differences (e.g. at most 1 amino acid difference in each CDR and at most 1 amino acid difference in each framework region) when compared to a VH region of a reference binding molecule herein; and the VL region has at most 7 amino acid differences (e.g. at most 1 amino acid difference in each CDR and at most 1 amino acid difference in each framework region) when compared to a VL region of a reference binding molecule herein; wherein the variant binding molecule binds to the same target antigen as the reference binding molecule, and preferably exhibits the same antigen cross-reactivity as the reference binding molecule.

In some embodiments, the binding molecule comprises:
a) a VH region comprising the amino acid sequence of SEQ ID NO: 51, or a sequence having at least 80%, 85%, 90%, 95%, 98% or 99% sequence identity thereto; and
b) a VL region comprising the amino acid sequence of SEQ ID NO: 55 or a sequence having at least 80%, 85%, 90%, 95%, 98% or 99% sequence identity thereto, wherein (i) $X_1$ and $X_2$ of SEQ ID NO: 55 are each any amino acid (SEQ ID NO: 76); or (ii) $X_1$ of SEQ ID NO: 55 is P or S and $X_2$ of SEQ ID NO: 55 is R, T or G (SEQ ID NO: 77).

For example, in some embodiments, the binding molecule comprises:
a) a VH region comprising the amino acid sequence of SEQ ID NO: 51, or a sequence having at least 80%, 85%, 90%, 95%, 98% or 99% sequence identity thereto; and
b) a VL region comprising the amino acid sequence of SEQ ID NO: 76 or a sequence having at least 80%, 85%, 90%, 95%, 98% or 99% sequence identity thereto.

For example, in some embodiments, the binding molecule comprises:
a) a VH region comprising the amino acid sequence of SEQ ID NO: 51, or a sequence having at least 80%, 85%, 90%, 95%, 98% or 99% sequence identity thereto; and
b) a VL region comprising the amino acid sequence of SEQ ID NO: 77 or a sequence having at least 80%, 85%, 90%, 95%, 98% or 99% sequence identity thereto.
c) In some embodiments, the binding molecule comprises:
d) a VH region comprising the amino acid sequence of SEQ ID NO: 51, or a sequence having at least 80%, 85%, 90%, 95%, 98% or 99% sequence identity thereto; and
e) a VL region comprising the amino acid sequence of SEQ ID NO: 52, or a sequence having at least 80%, 85%, 90%, 95%, 98% or 99% sequence identity thereto.

In some embodiments, the binding molecule comprises:
a) a VH region comprising the amino acid sequence of SEQ ID NO: 51, or a sequence having at least 80%, 85%, 90%, 95%, 98% or 99% sequence identity thereto; and
b) a VL region comprising the amino acid sequence of SEQ ID NO: 53, or a sequence having at least 80%, 85%, 90%, 95%, 98% or 99% sequence identity thereto.

In some embodiments, the binding molecule comprises:
a) a VH region comprising the amino acid sequence of SEQ ID NO: 51, or a sequence having at least 80%, 85%, 90%, 95%, 98% or 99% sequence identity thereto; and
b) a VL region comprising the amino acid sequence of SEQ ID NO: 54, or a sequence having at least 80%, 85%, 90%, 95%, 98% or 99% sequence identity thereto.

In some embodiments, the binding molecule comprises:
a) a VH region comprising the amino acid sequence of SEQ ID NO: 56, or a sequence having at least 80%, 85%, 90%, 95%, 98% or 99% sequence identity thereto; and
b) a VL region comprising the amino acid sequence of SEQ ID NO: 57, or a sequence having at least 80%, 85%, 90%, 95%, 98% or 99% sequence identity thereto.

In some embodiments, the binding molecule comprises:
a) a VH region comprising the amino acid sequence of SEQ ID NO: 58, or a sequence having at least 80%, 85%, 90%, 95%, 98% or 99% sequence identity thereto; and
b) a VL region comprising the amino acid sequence of SEQ ID NO: 59, or a sequence having at least 80%, 85%, 90%, 95%, 98% or 99% sequence identity thereto.

In some embodiments, the binding molecule comprises:
a) a VH region comprising the amino acid sequence of SEQ ID NO: 60, or a sequence having at least 80%, 85%, 90%, 95%, 98% or 99% sequence identity thereto; and
b) a VL region comprising the amino acid sequence of SEQ ID NO: 61, or a sequence having at least 80%, 85%, 90%, 95%, 98% or 99% sequence identity thereto.

In some embodiment, the binding molecule comprises:
a) a VH region comprising an amino acid sequence having at least 80%, 85%, 90%, 95%, 98%, 99% or 100% sequence identity to a reference amino acid sequence of SEQ ID NO: 51, 56, 58, 60, or a functional variant thereof; and
b) a VL region comprising an amino acid sequence having at least 70%, 75%, 80%, 90%, 95% or 100% sequence identity to a reference amino acid sequence of SEQ ID NO: 52, 53, 54, 55, 57, 59, 61, or a functional variant thereof, wherein (i) $X_1$ and $X_2$ of SEQ ID NO: 55 are each any amino acid (SEQ ID NO: 76); or (ii) $X_1$ of SEQ ID NO: 55 is P or S and $X_2$ of SEQ ID NO: 55 is R, T or G (SEQ ID NO: 77).

The foregoing can be applied to any of the antibodies illustrated in FIG. 3 or FIG. 4 or binding molecules of Table 3, or to any of the binding molecules described herein, wherein the amino acid differences are defined relative to the VH and/or VL sequences thereof, and wherein the binding molecule binds to the same target antigen as said binding molecules, and preferably exhibits the same antigen cross-reactivity. Thus, the reference binding molecule in any of the embodiments herein may be an antibody having a VH and VL sequence of any of the antibodies illustrated in FIG. 3 or FIG. 4 or binding molecules of Table 3.

The amino acid difference may be an amino acid substitution, insertion or deletion. In some embodiments the amino acid difference is a conservative amino acid substitution as described herein.

The binding molecule of the invention may be provided in isolated form.

In some embodiments, the binding molecule of the invention is an immunoglobulin molecule. In some embodiments, the binding molecule is an antibody, or an antigen-binding fragment thereof.

In particular, an antibody is a protein including at least one or two, heavy (H) chain variable regions (abbreviated herein as VH), and at least one or two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FW). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987). Preferably, each VH and VL region is composed of three CDRs and four FWs, arranged from amino-terminus to carboxy-terminus in the following order: FW1, CDR1, FW2, CDR2, FW3, CDR3, FW4.

The heavy or light chain of the antibody can further include all or part of a heavy or light chain constant region. In some embodiments, the binding molecule comprises all or part of a heavy chain constant region of SEQ ID NO: 78 and all or part of a light chain constant region of SEQ ID NO: 79. In some embodiments, the binding molecule comprises a heavy chain constant region and a light chain constant region as shown in Table 7. The binding molecule may comprise a functional fragment of a heavy chain constant region and/or a light chain constant region as shown in Table 7, such as a fragment wherein the binding molecule retains the ability to bind to one or more Fc receptors, as described herein. In some embodiments the binding molecule may comprise a heavy chain constant region and a light chain constant region as shown in Table 7, and may further comprise a VH region and a VL region as disclosed herein, e.g. the VH and VL sequences of any of the antibodies illustrated in FIG. 3 or FIG. 4 or binding molecules of Table 1. In some embodiments, the binding molecule is an antibody that is a tetramer of two heavy immunoglobulin chains and two light immunoglobulin chains, wherein the heavy and light immunoglobulin chains are interconnected by, e.g., disulfide bonds. The heavy chain constant region includes three domains, CH1, CH2 and CH3. In some embodiments, the binding molecule has a heavy chain constant region of SEQ ID NO: 78. The light chain constant region is comprised of one domain, CL. In some embodiments, the binding molecule has a light chain constant region of SEQ ID NO: 79. The variable region of the heavy and light chains contains a binding domain that interacts with an antigen.

The "Kabat numbering system" is generally used when referring to a residue in the variable region (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop, when numbered using the Kabat numbering convention, varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The table below lists the positions of the amino acids comprising the variable regions of the antibodies in each system.

TABLE 1

Positions of the amino acids comprising the variable regions of the antibodies

| Region | Kabat | AbM | Chothia |
| --- | --- | --- | --- |
| LCDR1 | L24-L34 | L24-L34 | L24-L34 |
| LCDR2 | L50-L56 | L50-L56 | L50-L56 |
| LCDR3 | L89-L97 | L89-L97 | L89-L97 |
| HCDR1[1] | H31-H35B | H26-H35B | H26-H32 . . . 34 |
| HCDR1[2] | H31-H35 | H26-H35 | H26-H32 |
| HCDR2 | H50-H65 | H50-H58 | H52-H56 |
| HCDR3 | H95-H102 | H95-H102 | H95-H102 |

[1]Kabat Numbering
[2]Chothia Numbering

ImMunoGeneTics (IMGT) also provides a numbering system for the immunoglobulin variable regions, including the CDRs. See, e.g., Lefranc, M. P. et al., Dev. Comp. Immunol. 27: 55-77(2003). The IMGT numbering system is based on an alignment of more than 5,000 sequences, structural data, and characterization of hypervariable loops and allows for easy comparison of the variable and CDR regions for all species. According to the IMGT numbering schema, HCDR1 is at positions 26 to 35, HCDR2 is at positions 51 to 57, HCDR3 is at positions 93 to 102, LCDR1 is at positions 27 to 32, LCDR2 is at positions 50 to 52, and LCDR3 is at positions 89 to 97.

The term "antibody" includes intact immunoglobulins of types IgA, IgG, IgE, IgD, IgM (as well as subtypes thereof), wherein the light chains of the immunoglobulin may be of types kappa or lambda. The binding molecule of the invention may be, or may comprise, a full-length antibody, or may be or comprise an antigen-binding fragment thereof. The term antigen binding fragment, as used herein, refers to a portion of an antibody that binds to CCR9, e.g., a molecule in which one or more immunoglobulin chains is not full length, but which binds to CCR9. In some embodiments, the antigen-binding fragment is one or more selected from a Fv fragment, an Fab fragment, an F(ab')2 fragment, an Fab' fragment, a dsFv fragment, an scFv fragment, an sc(Fv)2 fragment, a dAb fragment, a single chain antibody, or a combination thereof. For example, in some embodiments, the antigen-binding fragment is a Fab fragment. In some embodiments, the binding molecule comprises a Fab domain.

The antibodies of the invention or antigen-binding fragments thereof may have any antibody format. In some embodiments, the antibody has the "conventional" format described above. Alternatively, the antibody can be in some embodiments a Fab fragment. The antibody or antigen-binding fragment according to the invention can also be a Fab', an Fv, an scFv, an Fd, a V NAR domain, an IgNAR, an intrabody, an IgG CH2, a minibody, a single-domain antibody, an Fcab, an scFv-Fc, F(ab')2, a di-scFv, a bi-specific T-cell engager (BiTE®), a F(ab')3, a tetrabody, a triabody, a diabody, a DVD-Ig, an (scFv)2, or a mAb2.

In some embodiments, the binding molecule is a monoclonal antibody (mAb). In some embodiments, the binding molecule is a polyclonal antibody.

A "monoclonal antibody" (mAb) refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals.

In some embodiments, the antibody or antigen binding fragment is one or more selected from a murine antibody, a humanised antibody, a chimeric antibody, a fully human antibody, a monoclonal antibody, a polyclonal antibody, a recombinant antibody, a multispecific antibody, or a combination thereof. In some embodiments, the antibody or antigen binding fragment is a humanised antibody. In some embodiments, an antibody of the invention does not induce an anti-human antibody response, for example, a murine anti-human antibody response.

The antibodies of the invention and antigen-binding fragments thereof may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to the human patient.

Especially preferred are human or humanized antibodies, especially as recombinant human or humanized antibodies. The term "humanised antibody" refers to an antibody derived from a non-human (e.g., murine) immunoglobulin, which has been engineered to contain minimal non-human (e.g., murine) sequences. Typically, humanised antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region residues of a human immunoglobulin are replaced with the corresponding residues in an antibody from a non-human species that has the desired specificity, affinity, and capability.

Humanised antibodies can be further modified by the substitution of additional residues either in the Fv framework region and/or within the replaced non-human residues to refine and optimize antibody specificity, affinity, and/or capability. In general, humanised antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanised antibody can also comprise at least a portion of an immunoglobulin constant region or domain (Fc), typically that of a human immunoglobulin. Examples of methods used to generate humanised antibodies are described in U.S. Pat. Nos. 5,225,539 or 5,639,641.

In some embodiments, an antibody of the invention is a human antibody. The term "human antibody" means an antibody produced in a human or an antibody having an amino acid sequence corresponding to an antibody produced in a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

In some embodiments, an antibody of the invention is a chimeric antibody. The term "chimeric antibodies" refers to antibodies in which the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

There are five major classes of heavy chain constant region, classified as IgA, IgG, IgD, IgE and IgM, each with characteristic effector functions designated by isotype. For example, IgG is separated into four subclasses known as IgG1, IgG2, IgG3, and IgG4. Ig molecules interact with multiple classes of cellular receptors. For example, IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The antibodies of the invention or antigen-binding fragments thereof may be any isotype, i.e. IgA, IgD, IgE, IgG and IgM, and synthetic multimers of the four-chain immunoglobulin (Ig) structure. In preferred embodiments, the antibodies or antigen-binding fragments thereof are IgG isotype. The antibodies or antigen-binding fragments can be any IgG subclass, for example IgG1, IgG2, IgG3, or IgG4 isotype. In preferred embodiments, the antibodies or antigen-binding fragments thereof are of an IgG1 or IgG2 isotype.

In some embodiments, the antibodies comprise a heavy chain constant region that is of IgG isotype. In some embodiments, the antibodies comprise a portion of a heavy chain constant region that is of IgG isotype. In some embodiments, the IgG constant region or portion thereof is an IgG1, IgG2, IgG3, or IgG4 constant region. Preferably, the IgG constant region or portion thereof is an IgG1 or IgG2 constant region. Antibody molecules can also have other formats, e.g. IgG1 with YTE (Dall'Acqua et al. (2002) J.

Immunology, 169: 5171-5180; Dall'Acqua et al. (2006) J Biol. Chem. 281 (33):23514-24) and/or TM mutations (Oganesyan et al. (2008) Acta Cryst D64:700-4) in the Fc region.

The antibodies of the invention or antigen-binding fragments thereof may comprise a lambda light chain or a kappa light chain. Engineered antibodies and antigen-binding fragments thereof include those in which modifications have been made to framework residues within the VH region and/or VL region. Such modifications may improve the properties of the antibody, for example to decrease the immunogenicity of the antibody and/or improve antibody production and purification.

The binding molecules of the invention, include both intact and modified forms of the binding molecules disclosed herein. For example, a binding molecule of the invention can be functionally linked (e.g. by chemical coupling, genetic fusion, noncovalent association, or otherwise) to one or more other molecular entities, such as a pharmaceutical agent, a detection agent, and/or a protein or peptide that can mediate association of a binding molecule disclosed herein with another molecule (e.g. a streptavidin core region or a polyhistidine tag) Non-limiting examples of detection agents include: enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase, e.g., horseradish peroxidase; dyes; fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates, e.g., Europium etc., (Perkin Elmer and Cis Biointernational); chemoluminescent labels or chemiluminescers, such as isoluminol, luminol and the dioxetanes; bio-luminescent labels, such as luciferase and luciferin; sensitizers; coenzymes; enzyme substrates; radiolabels, including but not limited to, bromine77, carbon14, cobalt57, fluorine8, gallium67, gallium68, hydrogen3 (tritium), indium111, indium113m, iodine123m, iodine125, iodine126, iodine131, iodine133, mercury107, mercury203, phosphorous32, rhenium99m, rhenium101, rhenium105, ruthenium95, ruthenium97, ruthenium103, ruthenium105, scandium47, selenium75, sulphur35, technetium99, technetium99m, tellurium121m, tellurium122m, tellurium125m, thulium165, thulium167, thulium168 and yttrium199; particles, such as latex or carbon particles, metal sol, crystallite, liposomes, cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a Botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The binding molecules of the invention also include derivatives that are modified (e.g., by the covalent attachment of any type of molecule to the binding molecule) such that covalent attachment does not prevent the binding molecule from binding to its target (e.g. epitope), or otherwise impair the biological activity of the binding molecule. Suitable derivatives may be produced by methods that include, but are not limited to fucosylation, glycosylation, acetylation, PEGylation, phosphorylation, and amidation.

Further embodiments are multispecific binding molecule (bispecific, trispecific etc.) and other conjugates, e.g. with cytotoxic small molecules. The binding molecules of the present invention, including antibodies of the present invention, can be obtained using conventional techniques known to persons skilled in the art and their utility confirmed by conventional binding studies—exemplary methods are described in Examples 3 and 4. By way of example, a simple binding assay is to incubate the cell expressing an antigen with the antibody. If the antibody is tagged with a fluorophore, the binding of the antibody to the antigen can be detected by FACS analysis.

Antibodies of the present invention can be raised in various animals including mice, rats, rabbits, goats, sheep, monkeys or horses. Antibodies may be raised following immunisation with individual capsular polysaccharides, or with a plurality of capsular polysaccharides. Blood isolated from these animals contains polyclonal antibodies—multiple antibodies that bind to the same antigen. Antigens may also be injected into chickens for generation of polyclonal antibodies in egg yolk. To obtain a monoclonal antibody that is specific for a single epitope of an antigen, antibody-secreting lymphocytes are isolated from an animal and immortalized by fusing them with a cancer cell line. The fused cells are called hybridomas, and will continually grow and secrete antibody in culture. Single hybridoma cells are isolated by dilution cloning to generate cell clones that all produce the same antibody; these antibodies are called monoclonal antibodies. Methods for producing monoclonal antibodies are conventional techniques known to those skilled in the art (see e.g. Making and Using Antibodies: A Practical Handbook. GC Howard. CRC Books. 2006. ISBN 0849335280). Polyclonal and monoclonal antibodies are often purified using Protein A/G or antigen-affinity chromatography.

The antibody or antigen binding fragment thereof of the invention may be prepared as a monoclonal anti-CCR9 antibody, which can be prepared using hybridoma methods, such as those described by Kohler and Milstein, Nature 256:495 (1975). Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or an in vitro binding assay, e.g., radioimmunoassay (RIA) or enzyme-linked immunosorbent assay (ELISA), can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid using known methods.

Alternatively, the binding molecule (e.g. a monoclonal antibody) can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or antigen-binding fragments thereof of the desired species can be isolated from phage display libraries expressing CDRs of the desired species as described in McCafferty et al., Nature 348:552-554 (1990); Clackson et al., Nature, 352:624-628 (1991); and Marks et al., J. Mol. Biol. 222:581-597 (1991).

The polynucleotide(s) encoding a binding molecule of the invention can further be modified in a number of different manners using recombinant DNA technology to generate alternative binding molecules. In some embodiments, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the antibody or antigen-binding fragment thereof is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated. See, e.g., Cole et al., Monoclonal Antibodies and Cancer Therapy, Alan R. Liss, p. 77 (1985); Boemer et al., J. Immunol. 147 (1):86-95 (1991); U.S. Pat. No. 5,750,373.

In some embodiments, the antibody or antigen-binding fragment thereof can be selected from a phage library, where that phage library expresses human antibodies, as described, for example, in Vaughan et al., Nat. Biotech. 14:309-314 (1996); Sheets et al., Proc. Natl. Acad. Sci. USA, 95:6157-6162 (1998); Hoogenboom and Winter, J. Mol. Biol. 227: 381 (1991); and Marks et al., J. Mol. Biol. 222:581 (1991). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., J. Molec. Biol. 376:1182-1200 (2008), each of which is incorporated by reference in its entirety.

Affinity maturation strategies and chain shuffling strategies are known in the art and can be employed to generate high affinity human antibodies or antigen-binding fragments thereof. See Marks et al., BioTechnology 10:779-783 (1992), incorporated by reference in its entirety.

In some embodiments, the antibody or antigen binding fragment thereof (e.g. an monoclonal antibody) can be a humanised antibody. Methods for engineering, humanizing or resurfacing non-human or human antibodies can also be used and are well known in the art. A humanised, resurfaced or similarly engineered antibody can have one or more amino acid residues from a source that is non-human, e.g., but not limited to, mouse, rat, rabbit, non-human primate, or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. Suitably, the CDR residues may be directly and most substantially involved in influencing CCR9 binding. Accordingly, part or all of the non-human or human CDR sequences are preferably maintained while the non-human sequences of the variable and constant regions can be replaced with human or other amino acids.

Antibodies can also optionally be humanised, resurfaced, engineered or human antibodies engineered with retention of high affinity for the antigen CCR9 and other favourable biological properties. To achieve this goal, humanised (or human) or engineered anti-CCR9 antibodies and resurfaced antibodies can be optionally prepared by a process of analysis of the parental sequences and various conceptual humanised and engineered products using three-dimensional models of the parental, engineered, and humanised sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as CCR9. In this way, FW residues can be selected and combined from the consensus and import sequences so that the desired antibody characteristic, such as increased affinity for the target antigen(s), is achieved.

Humanization, resurfacing or engineering of anti-CCR9 antibodies or antigen-binding fragments thereof of the present invention can be performed using any known method, such as but not limited to those described in, Jones et al., Nature 321:522 (1986); Riechmann et al., Nature 332:323 (1988); Verhoeyen et al., Science 239:1534 (1988); Sims et al., J. Immunol. 151: 2296 (1993); Chothia and Lesk, J. Mol. Biol. 196:901 (1987); Carter et al., Proc. Natl. Acad. Sci. USA 89:4285 (1992); Presta et al., J. Immunol. 151:2623 (1993); U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; International Application Nos. PCT/US98/16280; PCT/US96/18978; PCT/US91/09630; PCT/US91/05939; PCT/US94/01234; PCT/GB89/01334; PCT/GB91/01134; PCT/GB92/01755; International Patent Application Publication Nos. WO90/14443; WO90/14424; WO90/14430; and European Patent Publication No. EP 229246; each of which is entirely incorporated herein by reference, including the references cited therein.

Anti-CCR9 humanised antibodies and antigen-binding fragments thereof can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In some embodiments, a fragment (e.g. antibody fragment) of the antibody (e.g. anti-CCR9 antibody) is provided. Various techniques are known for the production of antibody fragments. Traditionally, these fragments are derived via proteolytic digestion of intact antibodies, as described, for example, by Morimoto et al., J. Biochem. Biophys. Meth. 24:107-117 (1993) and Brennan et al., Science 229:81 (1985). In some embodiments, anti-CCR9 antibody fragments are produced recombinantly. Fab, Fv, and scFv antibody fragments can all be expressed in and secreted from *E. coli* or other host cells, thus allowing the production of large amounts of these fragments. Such anti-CCR9 antibody fragments can also be isolated from the antibody phage libraries discussed above. The anti-CCR9 antibody fragments can also be linear antibodies as described in U.S. Pat. No. 5,641,870. Other techniques for the production of antibody fragments will be apparent to the skilled practitioner.

According to the present invention, techniques can be adapted for the production of single-chain antibodies specific to CCR9. See, e.g., U.S. Pat. No. 4,946,778). In addition, methods can be adapted for the construction of Fab expression libraries to allow rapid and effective identification of monoclonal Fab fragments with the desired specificity for CCR9, or derivatives, fragments, analogs or homologs thereof. See, e.g., Huse et al., Science 246:1275-1281 (1989). Antibody fragments can be produced by techniques known in the art including, but not limited to: F(ab')2 fragment produced by pepsin digestion of an antibody molecule; Fab fragment generated by reducing the disulfide bridges of an F(ab')2 fragment; Fab fragment generated by the treatment of the antibody molecule with papain and a reducing agent; or Fv fragments.

A modified binding molecule (e.g. antibody or antigen-binding fragment thereof as provided herein) can comprise any type of binding region that provides for the association of the binding molecule with CCR9. In this regard, the binding region may be a variable region, that can comprise or be derived from any type of mammal that can be induced to mount a humoral response and generate immunoglobulins against the desired antigen. As such, the variable region of an anti-CCR9 antibody or antigen-binding fragment thereof can be, for example, of human, murine, non-human primate (e.g., cynomolgus monkeys, macaques, etc.) or lupine origin. In some embodiments, both the variable and constant regions of the modified antibody or antigen-binding fragment thereof are human. In some embodiments, the variable regions of a compatible antibody (usually derived from a non-human source) can be engineered or specifically tailored to improve the binding properties or reduce the immunogenicity of the molecule. In this respect, variable regions useful in the present invention can be humanised or otherwise altered through the inclusion of imported amino acid sequences.

In some embodiments, the variable domains in both the heavy and light chains of an antibody or antigen-binding fragment thereof are altered by at least partial replacement of one or more CDRs and/or by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It is not necessary to replace all of the CDRs with the complete CDRs from the donor variable region to transfer the antigen-binding capacity of one variable domain to another. Rather, it is only necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art to carry out routine experimentation to obtain a functional antibody with reduced immunogenicity.

Alterations to the variable region notwithstanding, those skilled in the art will appreciate that a modified antibody or antigen-binding fragment thereof of this invention can comprise an antibody (e.g., full-length antibody or antigen-binding fragment thereof) in which at least a fraction of one or more of the constant region domains has been deleted or otherwise altered so as to provide desired biochemical characteristics such as increased effector function including improved ability to induce ADCC when compared with an antibody of approximately the same immunogenicity comprising a native or unaltered constant region. In some embodiments, the constant region of the modified antibody will comprise a human constant region. Modifications to the constant region compatible with this invention comprise additions, deletions or substitutions of one or more amino acids in one or more domains. That is, a modified antibody disclosed herein can comprise alterations or modifications to one or more of the three heavy chain constant domains (CH1, CH2 or CH3) and/or to the light chain constant domain (CL). In some embodiments, a modified constant region wherein one or more domains are partially or entirely deleted are contemplated. In some embodiments, a modified antibody will comprise domain deleted constructs or variants wherein the entire CH2 domain has been removed (ΔCH2 constructs). In some embodiments, the omitted constant region domain can be replaced by a short amino acid spacer (e.g., 10 residues) that provides some of the molecular flexibility typically imparted by the absent constant region.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics: 1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

The present invention further embraces variants and equivalents that are substantially homologous to a binding molecule of the invention (e.g. an antibody, such as a murine, chimeric, humanised or human antibody, or antigen-binding fragments thereof). These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

TABLE 2

| Conservative amino acid substituions | |
|---|---|
| Basic | arginine, lysine, histidine |
| Acidic | glutamic acid, aspartic acid |
| Polar | glutamine, asparagine |
| Hydrophobic | leucine, isoleucine, valine |
| Aromatic | phenylalanine, tryptophan, tyrosine |
| Small | glycine, alanine, serine, threonine, methionine |

In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the binding molecules of the present invention. A limited number of non-conservative amino acids, amino acids that are not encoded by the genetic code, and unnatural amino acids may be substituted for polypeptide amino acid residues. The binding molecules of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and amino-acylating tRNA are known in the art. Transcription and translation of plasmids containing nonsense mutations is carried out in a cell free system comprising an E. coli S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in Xenopus oocytes by microinjection of mutated mRNA and chemically amino-acylated suppressor tRNAs (Turcatti et al., J. Biol. Chem. 271:19991-8, 1996). Within a third method, E. coli cells are cultured in the absence of a natural amino acid that is to be replaced (e.g., phenylalanine) and in the presence of desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of binding molecules of the present invention.

Essential amino acids in the binding molecules of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labelling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the binding molecules of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

5.2 Compositions

Also provided herein are compositions comprising a binding molecule of the invention. The composition may comprise any binding molecule as described herein. The composition may comprise more than one binding molecule as described herein.

In another aspect, there is provided a composition comprising a binding molecule that binds to CCR9, wherein said binding molecule is capable of (i) inhibiting binding of CCL25 to CCR9, and (ii) mediating antibody dependent cell-mediated cytotoxicity against a CCR9-expressing cell to which it binds.

A composition as described herein may be a pharmaceutical composition, such as a composition comprising a binding molecule of the present invention and further comprising at least one pharmaceutically acceptable carrier or diluent. The term "pharmaceutical composition" refers to a preparation that is in such form as to permit the biological activity of the active ingredient to be effective, and which contains no additional components which are unacceptably toxic to a subject to which the composition would be administered. Such composition can be sterile, and can comprise a pharmaceutically acceptable carrier, such as physiological saline. Suitable pharmaceutical compositions can comprise one or more of a buffer (e.g., acetate, phosphate or citrate buffer), a surfactant (e.g., polysorbate), a stabilizing agent (e.g., human albumin), a preservative (e.g., benzyl alcohol), and absorption promoter to enhance bioavailability, and/or other conventional solubilizing or dispersing agents.

In some embodiments, a pharmaceutical composition of the invention can comprise a pharmaceutically acceptable, non-toxic, sterile carrier such as physiological saline, non-toxic buffers, preservatives and the like. Suitable formulations for use in the therapeutic methods disclosed herein are described in Remington's Pharmaceutical Sciences, 22nd ed., Ed. Lloyd V. Allen, Jr. (2012).

In some embodiments, a pharmaceutical composition of the invention may be comprised within one or more formulation selected from a capsule, a tablet, an aqueous suspension, a solution, a nasal aerosol, or a combination thereof.

In some embodiments, the pharmaceutical composition comprises more than one type of binding molecule of the invention. For example, a pharmaceutical composition may comprise two or more selected from an antibody, an antigen-binding fragment, or a combination thereof.

The term "a pharmaceutically effective amount" of a binding molecule means an amount sufficient to achieve effective binding to a target and to achieve a benefit, e.g., to ameliorate symptoms of a disease or condition or to detect a substance or a cell.

In some embodiments, a pharmaceutical composition may comprise a buffer (e.g., acetate, phosphate or citrate buffer), a surfactant (e.g., polysorbate), optionally a stabilizer agent (e.g., human albumin), etc.

Suitably, the binding molecule of the invention binds to CCR9 molecule with sufficient affinity such that the binding molecule is useful as a therapeutic agent or a diagnostic reagent in targeting CCR9.

5.3 Therapeutic Methods

The invention also relates to using the binding molecules and compositions of the invention in therapeutic methods. The invention provides a binding molecule of the invention for use in such therapeutic methods, e.g. a binding molecule of the invention for use in a method of treating the human or animal body by therapy. Where therapeutic methods and uses are described herein with reference to the binding molecule of the invention, also encompassed are the same methods and uses where the binding molecule is present in a composition, such as a pharmaceutical composition, such as a pharmaceutical composition as described herein.

Thus, the invention embraces the above defined binding molecule and the above defined pharmaceutical composition for use in a method of treating a CCR9-mediated disease or condition.

In one aspect, there is provided a binding molecule of the invention for use in treating a CCR9-mediated disease or condition. Also provided is a composition of the invention, e.g., a pharmaceutical composition of the invention, for use in treating a CCR9-mediated disease or condition. Further provided is the use of a binding molecule of the invention in the manufacture of a medicament for the treatment of a CCR9-mediated disease or condition.

In another aspect there is provided a method of treating a CCR9-mediated disease or condition in a subject, the method comprising administering to the subject an effective amount of a binding molecule of the invention In one aspect, there is provided a binding molecule for use in treating a CCR9-mediated disease or condition in a subject wherein said binding molecule is capable of (i) inhibiting binding of CCL25 to CCR9, and (ii) mediating antibody dependent cell-mediated cytotoxicity against a CCR9-expressing cell to which it binds.

In one aspect, there is provided a method of treating a CCR9-mediated disease or condition in a subject, the method comprising administering to the subject an effective amount of a binding molecule which binds to CCR9, wherein said binding molecule is capable of (i) inhibiting binding of CCL25 to CCR9, and (ii) mediating antibody dependent cell-mediated cytotoxicity against a CCR9-expressing cell to which it binds.

In some embodiments of any of the treatment aspects, the CCR9-mediated disease or condition that is treated is an inflammatory bowel disease.

In some embodiments, the binding molecule is capable of depleting CCR9-expressing cells in the subject, for example, in the gut of the subject. Without being bound by theory, this may be due to the ability of the binding molecule to prevent migration of a CCR9-expressing cell from the periphery into the gut of a subject and/or due to the ability of the binding molecule to induce death of a CCR9-expressing cell to which it binds.

Thus, in one aspect, there is provided a method of depleting CCR9-expressing cells in a subject in need thereof comprising administering to the subject an effective amount of a binding molecule of the invention.

In some embodiments, the CCR9 polypeptide is comprised within a CCR9 polypeptide sequence, or a fragment thereof.

A "CCR9 polypeptide" may comprise the full length polypeptide sequence of CCR9, or may comprise a fragment of CCR9 of any length of the full length polypeptide sequence of CCR9 (e.g. comprising a polypeptide sequence of 5%, 15%, 25%, 35%, 45%, 55%, 65%, 75%, 85% or 95% of the full length polypeptide sequence of CCR9) which comprises an epitope which can bind (e.g. be bound by) a binding molecule of the invention.

The binding molecule may advantageously be used in methods for detecting a CCR9 epitope, and associated methods of diagnosis.

The term "treat" or "treating" as used herein encompasses therapeutic measures that cure, slow down, alleviate symptoms of, and/or halt progression of a diagnosed pathologic condition or disorder. Thus, those in need of treatment include those already with the disorder. Preferably, the term "treat" or "treating" as used herein means corrective treatment. The term "treat" or "treating" encompasses treating inflammatory bowel disease, and treating symptoms thereof and diseases/disorder associated therewith. In some embodiments the term "treat" or "treating" refers to a symptom of IBD, such as inflammation in the gut, abdominal pain, diarrhea, blood in the stool. In some embodiments, a subject is successfully "treated" for a CCR9-mediated disease or disorder (e.g., inflammatory bowel disease), according to the methods provided herein if the patient shows, e.g., total, partial, or transient alleviation or elimination of symptoms associated with the CCR9-mediated disease or disorder (e.g., inflammatory bowel disease). "Treat" or "treatment" also includes prophylactic treatment, e.g. to prevent the onset of disease, such as to prevent the onset of IBD.

To "prevent" refers to prophylactic or preventative measures that prevent and/or slow the development of a targeted pathologic condition or disorder. Thus, those in need of prevention include those prone to have or susceptible to the disorder. In some embodiments, a disease or disorder (e.g., inflammatory bowel disease) is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

The terms "subject", "individual" and "patient" are used interchangeably herein to refer to a mammalian subject. In some embodiments the "subject" is a human, domestic animals, farm animals, sports animals, and zoo animals, e.g., humans, non-human primates, dogs, cats, guinea pigs, rabbits, rats, mice, horses, cattle, etc. In some embodiments, the subject is a cynomolgus monkey (*Macaca fascicularis*). In preferable embodiments, the subject is a human. In methods of the invention, the subject may not have been previously diagnosed as having inflammatory bowel disease. Alternatively, the subject may have been previously diagnosed as having inflammatory bowel disease. The subject may also be one who exhibits disease risk factors, or one who is asymptomatic for inflammatory bowel disease. The subject may also be one who is suffering from or is at risk of developing inflammatory bowel disease. Thus, in some embodiments, a method of the invention may be used to confirm the presence of inflammatory bowel disease in a subject. For example, the subject may previously have been diagnosed with inflammatory bowel disease by alternative means. In some embodiments, the subject has been previously administered an inflammatory bowel disease therapy.

In some embodiments, methods of treatment of the invention comprise one or more administration step selected from oral, intravenous, intraarterial, intraperitoneal, intramuscular, subcutaneous, rectal, or vaginal, inhalation, topical, or a combination thereof.

In some embodiments, the binding molecule is delivered directly to the site of the adverse cellular population (e.g. thereby increasing the exposure of the diseased tissue to the therapeutic agent). In some embodiments, the administration is directly to the airway, e.g., by inhalation or intranasal administration.

In some embodiments, the inflammatory bowel disease is Crohn's disease, such as ileal or ileocolonic Crohn's disease. In some embodiments, the inflammatory bowel disease is ulcerative colitis.

5.4 Detection Methods

In a further aspect, there are provided methods for detecting the presence or absence of a CCR9 polypeptide. A binding molecule of the invention may be used in such methods.

In some embodiments, a method of detecting the presence or absence of a CCR9 polypeptide comprises:
- a) contacting a sample with a binding molecule of the invention to provide a binding molecule-antigen complex;
- b) detecting the presence or absence of said binding molecule-antigen complex;
- c) wherein the presence of the binding molecule-antigen complex confirms the presence of a CCR9 polypeptide.

In some embodiments, any of steps (i)-(iii) above are performed ex vivo or in vitro. In some embodiments, all of steps (i)-(iii) above are performed ex vivo or in vitro. In some embodiments, any of steps (i)-(iii) above are performed in vivo.

The binding molecule may be any binding molecule described herein, e.g. a binding molecule comprising a set of six CDRs as illustrated for any antibody in FIG. 3 or FIG. 4 or Table 4, or a binding molecule comprising a VH and VL as illustrated for any antibody in FIG. 3 or FIG. 4 or binding molecules of Table 3.

In some embodiments, the detection methods described herein are carried out in vitro. In some embodiments, the detection methods described herein are carried out ex vivo. In some embodiments, the detection methods described herein are carried out on a sample from a subject, such as a sample that has previously been obtained from the subject. The detection methods may, or may not, include a step of obtaining the sample from the subject. Suitably, a "sample" is a sample obtained from a subject (e.g. biopsy), cell line, tissue culture, or other source of cells potentially expressing CCR9. In some embodiments, a sample is a biopsy from a subject. Said biopsy may be from the gut of a subject suffering from an inflammatory bowel disease, or from the gut of a subject at risk of suffering from an inflammatory bowel disease. The sample may be an isolated sample from a subject.

The invention embraces a corresponding use of the binding molecule of the invention for detecting a CCR9 polypeptide (e.g. CCR9 polypeptide epitope).

In some embodiments, the presence of binding molecule-antigen complex is indicative of the presence of an inflammatory bowel disease, and the absence of the binding molecule-antigen complex is indicative of the absence of an inflammatory bowel disease.

In some embodiments, the inflammatory disease is an inflammatory bowel disease comprising a cell expressing a CCR9 polypeptide (e.g. CCR9 polypeptide epitope).

Thus, the present invention embraces use of the binding molecule of the invention in methods of diagnosing a subject with an inflammatory bowel disease, preferably wherein said inflammatory bowel disease comprises a CCR9-expressing cell.

In some embodiments, a method of detection or method of diagnosis may comprise measuring the expression level of CCR9 in a sample from a subject, and comparing the measured CCR9 expression level with a reference CCR9 level, wherein an increase in the measured CCR9 expression level compared to the reference CCR9 level is indicative of the presence of inflammatory bowel disease. In some embodiments, said reference CCR9 level is the expression level of CCR9 in a non-IBD (e.g. normal) sample of the same type, such as of the same tissue type.

A "binding molecule-antigen complex" means a complex (e.g. macromolecular complex) comprising an antigen which is bound to its respective binding molecule, e.g. CCR9 which is bound to a binding molecule of the invention. The term "binding molecule-antigen complex" may be used synonymously with the terms "bound CCR9-binding molecule complex" and "binding molecule bound to CCR9".

A binding molecule-antigen complex may be detected by any means known to the skilled person. In some embodiments, the binding molecule is labelled with a detectable label. Said label may be an epi-fluorescent label.

In some embodiments, a binding molecule-antigen complex is detected by means of a secondary (e.g. detection) antibody which binds the binding molecule and/or binding molecule-antigen complex.

Suitably, said secondary antibody comprises a detection means, such as a tag/label to aid detection. Said detection means is preferably conjugated to the secondary antibody. Examples of suitable labels include detectable labels such as radiolabels or fluorescent or coloured molecules, enzymatic markers or chromogenic markers—e.g. dyes that provide a visible colour change upon binding of the detection antibody to an antigen. By way of example, the label may be fluorescein-isothiocyanate (FITC), R-phycoerythrin, Alexa 532, CY3 or digoxigenin. The label may be a reporter molecule, which is detected directly, such as by detecting its fluorescent signal, or by exposure of the label to photographic or X-ray film. Alternatively, the label is not directly detectable, but may be detected, for example, in a two-phase system. An example of indirect label detection is binding of an antibody to the label.

In some embodiments, said secondary antibody comprises a fluorescent tag, and a binding molecule-antigen complex is detected by the florescence emitted from a, binding molecule-antigen-secondary antibody complex. A "binding molecule-antigen-secondary antibody complex" means a complex comprising an antigen (e.g. CCR9) which has become bound to a binding molecule, wherein said complex has further become bound by a secondary antibody which binds said binding molecule and/or binding molecule-antigen complex.

Suitably, a binding molecule-antigen complex is detected when the signal (e.g., fluorescence) emitted from the detection label is greater than the signal detected in a control comprising no binding molecule (e.g. no binding molecule which binds a CCR9). Said control may alternatively comprise a CCR9, but the sample is not applied to said control.

In another aspect, there is provided a second binding molecule that binds to CCR9 wherein said second binding molecule does not compete for binding to CCR9 with a first binding molecule.

The first binding molecule may be any binding molecule as disclosed herein that binds to CCR9. A suitable first binding molecule may be a binding molecule as illustrated in FIG. 4. A suitable first binding molecule may be a binding molecule comprising the VH and VL of any binding molecule illustrated in Table 3, or comprising a set of six CDRs (HCDR1, HCDR2, HCDR3, LCDR1, LCDR2, and LCDR3) of any binding molecule illustrated in Table 4. A suitable first binding molecule may be a binding molecule that:

a) comprises a heavy chain variable (VH) region having a set of CDRs HCDR1, HCDR2 and HCDR3 and a light chain variable (VL) region having a set of CDRs LCDR1, LCDR2 and LCDR3, of an antibody as shown in FIG. 4;

b) comprises a heavy chain variable (VH) region and a light chain variable (VL) region of an antibody shown in FIG. 4;

c) comprises a heavy chain variable (VH) region sequence of SEQ ID NO: 51 and a light chain variable (VL) region sequence of SEQ ID NO: 55, wherein (i) $X_1$ and $X_2$ of SEQ ID NO: 55 are each any amino acid (SEQ ID NO: 76); or (ii) $X_1$ of SEQ ID NO: 55 is P or S and $X_2$ of SEQ ID NO: 55 is R, T or G (SEQ ID NO: 77); or d) comprises a heavy chain variable (VH) region sequence of SEQ ID NO: 51 and a light chain variable (VL) region sequence of SEQ ID NO: 52, 53 or 54; or e) comprises a heavy chain variable (VH) region sequence of SEQ ID NO: 56 and a light chain variable (VL) region sequence of SEQ ID NO: 57.

Advantageously, the invention embraces the use of the second binding molecule (which does not compete for binding with the first binding molecule) to determine the abundance of CCR9-expressing cells in a sample which has been contacted with the first binding molecule.

Thus, there is provided a method of assessing the depletion of CCR9-expressing cells by a first binding molecule, the method comprising:

a) contacting said first binding molecule with a population of cells, wherein the population of cells comprises CCR9-expressing cells and immune effector cells, under conditions suitable to allow for antibody dependent cell-mediated cytotoxicity by the effector cells;

b) contacting said population of cells with a second binding molecule that binds to CCR9, and that does not compete for binding to CCR9 with the first binding molecule of step (i);

c) detecting CCR9-expressing cells in the population of cells that are bound by the second binding molecule of (ii);

d) comparing the amount of CCR9-expressing cells detected in step (iii) with the amount of CCR9-expressing cells in the original cell population used in step (i), and thereby determining the amount of CCR9-expressing cells that were depleted in step (i).

In some embodiments, the second binding molecule comprises the VH and VL sequences illustrated in Table 6, or the set of six CDRs illustrated in Table 6. For example, the first binding molecule may comprise the VH and VL of any binding molecule illustrated Table 3, or comprising a set of six CDRs of any binding molecule illustrated in Table 4, and the second binding molecule may comprise the VH and VL sequences illustrated in Table 6, or the set of six CDRs illustrated in Table 6.

In some embodiments, the second binding molecule is a binding molecule as described herein that binds CCR9 and that comprises:

a) a HCDR1 of SEQ ID NO: 44, or a functional variant thereof;

b) a HCDR2 of SEQ ID NO: 45, or a functional variant thereof;

c) a HCDR3 of SEQ ID NO: 46, or a functional variant thereof;

d) a LCDR1 of SEQ ID NO: 47, or a functional variant thereof; a LCDR2 of SEQ ID NO: 5, or a functional variant thereof; and e) a LCDR3 of SEQ ID NO: 48, or a functional variant thereof, wherein a functional variant is as defined herein In some embodiments, the second binding molecule is a binding molecule that binds to CCR9 and that comprises a heavy chain variable (VH) region having a set of CDRs HCDR1, HCDR2 and HCDR3 and a light chain variable (VL) region having a set of CDRs LCDR1, LCDR2 and LCDR3, wherein the VH region amino acid sequence comprises HCDR1 of SEQ ID NO: 44, HCDR2 of SEQ ID NO: 45 and HCDR3 of SEQ ID NO: 46, and wherein the VL region amino acid sequence comprises LCDR1 of SEQ ID NO: 47, LCDR2 of SEQ ID NO: 5 and LCDR3 of SEQ ID NO: 48.

In some embodiments, the second binding molecule is a binding molecule that binds to CCR9 and that comprises:

a) a VH region comprising the amino acid sequence of SEQ ID NO: 72, or a sequence having at least 80%, 85%, 90%, 95%, 98% or 99% sequence identity thereto; and b) a VL region comprising the amino acid sequence of SEQ ID NO: 73, or a sequence having at least 80%, 85%, 90%, 95%, 98% or 99% sequence identity thereto.

5.5 Polynucleotides, Vectors and Host Cells

In another aspect, there is provided a polynucleotide comprising a nucleic acid sequence encoding a binding molecule of the invention.

In some embodiments, the polynucleotide is an isolated polynucleotide.

In some embodiments, where the binding molecule comprises more than one polypeptide chain (e.g. where the binding molecule is an immunoglobulin molecule or fragment thereof, comprising at least one heavy chain and at least one light chain), the polynucleotide encodes one, some, or all of the polypeptide chains of the binding molecule. For example, the polynucleotide may encode the heavy chain polypeptide and the light chain polypeptide of a binding molecule. In some embodiments, the polynucleotide encodes a VH region of a binding molecule. In some embodiments, a polynucleotide of the invention encodes a VL region of a binding molecule. In some embodiments, the polynucleotide encodes a VH region and a VL region of a binding molecule.

In some embodiments, the polynucleotide further encodes a leader sequence (e.g. which functions as a secretory sequence for controlling transport of a polypeptide from the cell).

Variants of a polynucleotide described above are embraced by the invention. Polynucleotide variants can contain alterations in the coding regions, non-coding regions, or both. In some embodiments, a polynucleotide variant comprises an alteration that produces silent substitutions, additions, or deletions, but does not alter the properties or activities of the encoded polypeptide. In some embodiments, a polynucleotide variant is produced by a silent substitution due to the degeneracy of the genetic code. A polynucleotide variant can be produced for a variety of reasons, e.g., to optimize codon expression for a particular host (change codons in the human mRNA to those preferred by a bacterial host such as E. coli).

In another aspect there is provided a vector comprising the polynucleotide of the invention operably associated with a promoter; or comprising a polynucleotide encoding the VH region of a binding molecule of the invention and a polynucleotide encoding the VL region of a binding molecule of the invention wherein said polynucleotides are operably associated with one or more promoter(s). As used herein, the term "promoter" means any nucleic acid sequence that regulates the expression of a polynucleotide sequence by driving transcription of the polynucleotide sequence. As used herein, the term "operably associated" and "operatively linked" means that the promoter is in a correct functional location and/or orientation in relation to a polynucleotide sequence it regulates to control transcriptional initiation and/or expression of that sequence. In some embodiments, the nucleic acid sequences encoding the VH region and VL region are operably associated with the same promoter. In some embodiments, the nucleic acid sequences encoding the VH region and VL region are each operably associated with a separate promoter. In some embodiments, the separate promoters are promoters of the same type. In some embodiments, the separate promoters are promoters of different types.

Examples of vectors include viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Once assembled into the vector, the polynucleotide of the invention can be operatively linked to a promoter appropriate for expression of the polypeptide in a desired host.

A vector may comprise additional nucleic acid sequence(s) which control expression of the polynucleotide. For example, a vector may comprise one or more of an enhancer and a repressor sequence. As used herein, the term "enhancer" means a nucleic acid sequence that binds one or more proteins to increase transcriptional activation of a polynucleotide. As used herein, the term "repressor" means a nucleic acid sequence that binds one or more proteins to decrease transcriptional activation of a polynucleotide.

Another aspect provided herein is a host cell comprising a polynucleotide of the invention or a polynucleotide as disclosed herein, or a host cell comprising a vector of the invention or a vector as disclosed herein wherein the host cell is capable of producing a polypeptide encoded by the polynucleotide or vector.

Another aspect provided herein is a method of producing a binding molecule of the invention comprising expressing a polynucleotide or vector of the invention in a host cell. For example, in some embodiments, the method comprises culturing a host cell under conditions suitable for producing a binding molecule of the invention encoded by a polynucleotide or vector present in the host cell.

Suitable host cells for expression of a binding molecule of the invention include a prokaryote, yeast, insect, or higher eukaryotic cells (preferably wherein the polynucleotide is under the control of appropriate promoters). Prokaryotes include gram negative or gram positive organisms, for example E. coli or bacilli. Higher eukaryotic cells include established cell lines of mammalian origin as described herein. Cell-free translation systems can also be employed. In some embodiments, the host cell is a cell that does not fucosylate the Fc region of the binding molecule. In some embodiments, the host cell is a cell that expresses an enzyme which diverts the fucose pathway to produce GDP-D-rhamnose.

5.6 Afucosylation

Antibody effector function may be modified through the generation of antibodies with altered glycosylation patterns. For example, an antibody can be made that has an altered type of glycosylation, such as an afucosylated/hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 describes a cell line with a functionally disrupted FUT8 gene, which encodes a fucosyl transferase, such that antibodies expressed in such a cell line exhibit hypofucosylation. PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also [5]). PCT Publication WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GleNac structures which results in increased ADCC activity of the antibodies (see also [6]). WO 2011/035884 A1 describes processes for producing molecules lacking fucose on their glycomoieties. WO 2011/035884 A1 particularly describes cells for producing molecules, wherein the cells comprise at least one enzyme that uses GDP-6-deoxy-D-lyxo-4-hexulose as a substrate, wherein the enzyme converts the substrate to GDP-D-rhamnose, GDP-D-perosamine, GDP-deoxy-D-talose, GDP-6-deoxy-Daltrose, or GDP-4-keto-3,6-dideoxy-D-mannose.

5.7 Kits and Further Assays

In one aspect, there is provided a kit comprising a binding molecule of the invention. There is further embraced use of said kit in the methods of the present invention.

In some embodiments, a kit further comprises an isolated (e.g. purified) antigen or a cell expressing an antigen. For example, the kit may further comprise an isolated (e.g. purified) CCR9, or a cell expressing CCR9. In some embodiments, the kit comprises one or more containers. In some embodiments, the kit comprises all of the components necessary and/or sufficient to perform a detection assay as described herein, including all controls, directions for performing assays, and any necessary software for analysis and presentation of results.

A binding molecule of the invention can be used in assays for immunospecific binding by any method known in the art. The immunoassays that can be used include, but are not limited to, competitive and non-competitive assay systems using techniques such as Western blot, RIA, ELISA, ELISPOT, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays.

A binding molecule of the invention can be employed histologically, as in immunofluorescence, immunoelectron microscopy, or non-immunological assays, for example, for in situ detection of CCR9 or conserved variants or peptide fragments thereof. In situ detection can be accomplished by removing a histological specimen from a patient, and applying thereto a labelled binding molecule of the invention, e.g., applied by overlaying the labelled binding molecule onto a biological sample. Through the use of such a procedure, it is possible to determine not only the presence of CCR9, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

TABLE 3

Amino acid sequence of the VH and VL regions of exemplary binding molecules of the invention.

| Binding molecule | | VH/VL amino acid sequence | SEQ ID |
| --- | --- | --- | --- |
| AB243L00326 | VH | QVQLVQSGAEVKKPGASVKVSCKASGYTFTSYWMHWVRQAPGQGLEWIGVIYPG NSDTRYNQKFKGRVTITRDTSASTAYMELSSLRSEDTAVYYCTRDYYSNYVYYY AMDYWGQGTTVTVSS | 51 |
| | VL | DIVMTQTPLSLPVTPGEPASISCRSSQSLVHPNRNTYLHWYLQKPGQSPQLLIY KVSNRFSGVPDRFSGSGSGTDFTLKISRVEAEDVGVYYCSQSTHVPWTFGQGTK LEIK | 52 |
| AB243L00331 | VH | QVQLVQSGAEVKKPGASVKVSCKASGYTFTSYWMHWVRQAPGQGLEWIGVIYPG NSDTRYNQKFKGRVTITRDTSASTAYMELSSLRSEDTAVYYCTRDYYSNYVYYY AMDYWGQGTTVTVSS | 51 |
| | VL | DIVMTQTPLSLPVTPGEPASISCRSSQSLVHSNTNTYLHWYLQKPGQSPQLLIY KVSNRFSGVPDRFSGSGSGTDFTLKISRVEAEDVGVYYCSQSTHVPWTFGQGTK LEIK | 53 |
| AB1020243-fgl | VH | QVQLVQSGAEVKKPGASVKVSCKASGYTFTSYWMHWVRQAPGQGLEWIGVIYPG NSDTRYNQKFKGRVTITRDTSASTAYMELSSLRSEDTAVYYCTRDYYSNYVYYY AMDYWGQGTTVTVSS | 51 |
| | VL | DIVMTQTPLSLPVTPGEPASISCRSSQSLVHSNGNTYLHWYLQKPGQSPQLLIY KVSNRFSGVPDRFSGSGSGTDFTLKISRVEAEDVGVYYCSQSTHVPWTFGQGTK LEIK | 54 |

TABLE 3-continued

Amino acid sequence of the VH and VL regions of exemplary binding molecules of the invention.

| Binding molecule | | VH/VL amino acid sequence | SEQ ID |
|---|---|---|---|
| AB1020243 | VH | EVQLQQSGTVLARPGASVKMSCKASGYTFTSYWMHWVKQRPGQGLEWIGVIYPG NSDTRYNQKFKGKAKLTAVTSATTAYMELSSLTNEDSAVYYCTRDYYSNYVYYY AMDYWGQGTSVTVSS | 56 |
| | VL | DVVMTQTPLSLPVSLGDQASISCRSSQSLVHSNGNTYLHWYLQKPGQSPKLLIY KVSNRFSGVPDRFSGSGSGTDFTLKISRVEAEDLGVFFCSQSTHVPWTFGGGTK LEIK | 57 |
| AB1020011 | VH | EVQLVESGGGLVKPGGSRKLSCAASGFTFRDYGMHWVRQAPERGLEWVAYINSG SSAIYYADTVKGRFTISRDNTKNTLFLQMTSLRSEDTAMYYCARAGTAYWGQGT LVTVSA | 58 |
| | VL | DVVMTQTPLTLSVTFGQPASISCKSSQSLLDSDGKTYLNWLLQRPGQSPKRLIY QVSRLDSGVPDRFTGSGSGTDFTLKIIRVEAEDLGVYYCWQGSHFPRTFGGGTK LEIK | 59 |
| AB1020229 | VH | EVQLVESGGGLVQPKGSLKLSCAASGFTFNTYAMYWVRQAPGKGLEWVARIRSK SSNFATYYADSVKDRFTISRDDSQSMLYLQMNNLKTEDTAMYYCVR GGSDYWGQGTTLTVSS | 60 |
| | VL | DVVMTQTPLSLSVTIGQPASISCKSCQCLLYSDGKTYLNWLQQRPGQSPKRLMY QVSKLDPGIPDRFSGSGSETDFTLKISRVEAEDLGVYFCLQGTYYPYTFGSGTK LEIK | 61 |
| AB1020227 | VH | EVQLVESGGRLVQPKGSLKLSCAASGFTFNTYAMYWIRQAPGKGLEWVARIRSK SNNYATYYADSVKDRFTISRDDSQSMLYLQMNNLKTEDTAMYYCVRGGGFDYWG QGTTLTVSS | 62 |
| | VL | DVVMTQTPLSLSVTIGQPASISCKSSQSLLYSDGKTYLNWLQQRPGQSPKRLMY QVSKLDPGIPDRFSGSGSETDFTLKISRVEAEDLGVYYCLQGTYYPFTFGTGTK LEIK | 63 |
| AB1020234 | VH | EVQLVESGGGLVKPGGSLKLSCAASGFTFSSYAMSWVRQTPEKRLEWVATISDG GSYTYYPDNVKGRFTISRDNAKNNLYLQMSHLKSEDTAMYYCAR DPRYYFDYWGQGTTLTVSS | 64 |
| | VL | DVVMTQTPLSLPVSLGDQASISCRSSQSLVHSNGNTYLHWYLQKPGQSPKLLIY KVSNRFSGVPDRFSGSGSGTDFTLKISRVEAEDLGVYFCSQSTHVPWTFGGGTK LEIK | 65 |
| AB1020264 | VH | QVQLQQPGAELVKPGASVKLSCKASGYTFTSYWMHWVKQRPGRGLEWIGRIDPN SGGTKYNEKFKSKATLTVDKPSSTAYMQLSSLTSEDSAVYYCARGGLVYYFDYW GQGTTLTVSS | 66 |
| | VL | DVVMTQTPLSLPVSLGDQASISCRSSQSLVHSNGNTYLYWYLQKPGQSPKLLIY RVSNRFSGVPDRFSGSGSGTDFTLKISRVEAEDLGVYFCFQGTHVPHTFGSGTK LEIK | 67 |
| AB1020283 | VH | EVKLEESGGGLVQPGGSMKLSCVASGFSFSNYWMNWVRQSPEKGLEWVAQIRLK SDNYATHYAESVKGRFTISRDDSKSSVYLQMNNLRAEDTGIYYCTERPFSYWGQ GTLVTVSA | 68 |
| | VL | DVLMTQTPLSLPVSLGDQASISCRSSQSIVHSNGNTYLEWYLQKPGQSPKLLIY KVSNRFSGVPDRFSGSGSGTDFTLKISRVEAEDLGVYYCFQGSHVPLTFGAGTK LELK | 69 |
| AB1020310 | VH | EVQLQQSGPELVKPGASVKMSCKASGYTFTSYVMHWVKQKPGQGLEWIGYINPY NDGTKYNEKFKGKATLTSDKSSSTAYMELSSLTSEDSAVYYCAR NGGRGYAMDYWGQGTSVTVSS | 70 |
| | VL | DVLMTQTPLSLPVSLGDQASISCRSSQSIVHSNGNTYLEWYLQKPGQSPKLLIY KVSNRFSGVPDRFSGSGSGTDFTLKISRVEAEDLGVYYCFQGSHVPPTFGGGTK LEIK | 71 |
| AB1020069 | VH | EVKLEESGGGLVQPGGSMKLSCVASGFTFSNYWMNWVRQSPEKGLEWVAQIRLK SDNYATHYAESVKGRFTISKDDSKSSVYLQMNNLRAEDTGIYYCTE RPFAYWGQGTLVTVSS | 74 |
| | VL | DVLMTQTPLSLPVSLGDQASISCRSSQSIVHSNGNTYLEWYLQKPGQSPKLLIY KVSKRLSGVPDRFSGSGSGTEFTLKISRVEAEDLGVYYCFQGSHVPLTFGAGTK LELK | 75 |

TABLE 4

Amino acid sequence of the CDRs of the exemplary binding molecules

| Binding molecule | CDR | Amino acid sequence | SEQ ID | CDR | Amino acid sequence | SEQ ID |
|---|---|---|---|---|---|---|
| AB243L00326 | HCDR1 | SYWMH | 1 | LCDR1 | RSSQSLVHPNRNTYLH | 20 |
|  | HCDR2 | VIYPGNSDTRYNQKFKG | 2 | LCDR2 | KVSNRFS | 5 |
|  | HCDR3 | DYYSNYVYYYAMDY | 3 | LCDR3 | SQSTHVPWT | 6 |
| AB243L00331 | HCDR1 | SYWMH | 1 | LCDR1 | RSSQSLVHSNTNTYLH | 21 |
|  | HCDR2 | VIYPGNSDTRYNQKFKG | 2 | LCDR2 | KVSNRFS | 5 |
|  | HCDR3 | DYYSNYVYYYAMDY | 3 | LCDR3 | SQSTHVPWT | 6 |
| AB1020243-fg1 | HCDR1 | SYWMH | 1 | LCDR1 | RSSQSLVHSNGNTYLH | 22 |
|  | HCDR2 | VIYPGNSDTRYNQKFKG | 2 | LCDR2 | KVSNRFS | 5 |
|  | HCDR3 | DYYSNYVYYYAMDY | 3 | LCDR3 | SQSTHVPWT | 6 |
| AB1020243 | HCDR1 | SYWMH | 1 | LCDR1 | RSSQSLVHSNGNTYLH | 21 |
|  | HCDR2 | VIYPGNSDTRYNQKFKG | 2 | LCDR2 | KVSNRFS | 5 |
|  | HCDR3 | DYYSNYVYYYAMDY | 3 | LCDR3 | SQSTHVPWT | 6 |
| AB1020011 | HCDR1 | DYGMH | 7 | LCDR1 | KSSQSLLDSDGKTYLN | 10 |
|  | HCDR2 | YINSGSSAIYYADTVKG | 8 | LCDR2 | QVSRLDS | 11 |
|  | HCDR3 | AGTAY | 9 | LCDR3 | WQGSHFPRT | 12 |
| AB102229 | HCDR1 | TYAMY | 13 | LCDR1 | KSCQCLLYSDGKTYLN | 16 |
|  | HCDR2 | RIRSKSSNFATYYADSVKD | 14 | LCDR2 | QVSKLDP | 17 |
|  | HCDR3 | GGSDY | 15 | LCDR3 | LQGTYYPYT | 18 |
| AB1020227 | HCDR1 | TYAMY | 13 | LCDR1 | KSSQSLLYSDGKTYLN | 25 |
|  | HCDR2 | RIRSKSNNYATYYADSVKD | 23 | LCDR2 | QVSKLDP | 17 |
|  | HCDR3 | GGGFDY | 24 | LCDR3 | LQGTYYPFT | 26 |
| AB1020234 | HCDR1 | SYAMS | 27 | LCDR1 | RSSQSLVHSNGNTYLH | 22 |
|  | HCDR2 | TISDGGSYTYYPDNVKG | 28 | LCDR2 | KVSNRFS | 5 |
|  | HCDR3 | DPRYYFDY | 29 | LCDR3 | SQSTHVPWT | 6 |
| AB1020264 | HCDR1 | SYWMH | 1 | LCDR1 | RSSQSLVHSNGNTYLY | 32 |
|  | HCDR2 | RIDPNSGGTKYNEKFKS | 30 | LCDR2 | RVSNRFS | 33 |
|  | HCDR3 | GGLVYYFDY | 31 | LCDR3 | FQGTHVPHT | 34 |
| AB1020283 | HCDR1 | NYWMN | 35 | LCDR1 | RSSQSIVHSNGNTYLE | 38 |
|  | HCDR2 | QIRLKSDNYATHYAESVKG | 36 | LCDR2 | KVSNRFS | 5 |
|  | HCDR3 | RPFSY | 37 | LCDR3 | FQGSHVPLT | 39 |
| AB1020310 | HCDR1 | SYVMH | 40 | LCDR1 | RSSQSIVHSNGNTYLE | 38 |
|  | HCDR2 | YINPYNDGTKYNEKFKG | 41 | LCDR2 | KVSNRFS | 5 |
|  | HCDR3 | NGGRGYAMD | 42 | LCDR3 | FQGSHVPPT | 43 |
| AB1020069 | HCDR1 | NYWMN | 35 | LCDR1 | RSSQSIVHSNGNTYLE | 38 |
|  | HCDR2 | QIRLKSDNYATHYAESVKG | 36 | LCDR2 | KVSKRLS | 50 |
|  | HCDR3 | RPFAY | 49 | LCDR3 | FQGSHVPL | 39 |

5.8 Example 1—CCR9 Expression in Various Cells and Tissues

Cells were isolated from various tissues in human and from cynomolgus monkey. The proportion of cells from a given tissue and/or of a given cell type that expressed CCR9 was determined using flow cytometry.

As illustrated in FIG. 1A, cells expressing both CCR9 and CD4 were found in the colon, ileum and thymus of both human and cynomolgus tissue, and also found in the mesenteric lymph node in cynomolgus tissue. In contrast, CCR9+CD4+ cells were only present at a low level in the blood. It was also found that CCR9 mRNA was co-expressed with CD3+ cells of the cynomolgus ileum (data not shown).

CCR9 expression was assessed in human tissue. The greatest proportion of CCR9-expressing cells was found in CD4+ T cells of the thymus (76% of cells expressing CCR9), with high levels also being seen in CD4+ T cells (47% of cells expressing CCR9) and CD8+ T cells (37% of cells expressing CCR9) of the ileum of IBD patients. Some CCR9 expression was also seen in cells of the colon of IBD patients that were CD4+ T cells (9% of cells expressing CCR9) or CD8+ T cells (12% of cells expressing CCR9), with only low numbers of CCR9-expressing cells in the CD4+ and CD8+ T cells in the blood (<5%) of IBD patients. CCR9 expression was seen in 28% of B cells in the blood, with a lower level (11% and 16% respectively) in B cells in the colon and ileum. Only very low numbers of monocytes, dendritic cells (DCs) and plasmacytoid dendritic cells (pDCs) expressed CCR9 (<5%).

FIG. 1B shows the percentage of B cells expressing CCR9 in the ileum (left chart) and colon (right chart) of healthy and IBD patients. For each B cell type (naïve B cell, memory B cell, plasma cell), the results from healthy subjects are provided on the left and the results for IBD patients are provided on the right. It was found that there was a decrease in the number of B cells expressing CCR9 in IBD, with the greatest decrease observed in memory B cells. It is hypothesised that this may be due to high CCR9 ligand expression driving receptor internalisation in IBD.

FIG. 1C shows the percentage of T effector cells and T regs from the colon or ileum of healthy subjects or from IBD patients that express CCR9. For each tissue type indicated, the % of T effector cells expressing CCR9 is show on the left, and the % of Tregs expressing CCR9 is shown on the right. It was found that there was no apparent difference in the T effector/Treg ratio in either tissue type between healthy and IBD patients.

5.9 Example 2—Association of CCR9 with Pro-Inflammatory Cytokine Expression

Co-expression of the pro-inflammatory cytokines IFN-γ, IL-4, and IL-17 was assessed in human CD4+CCR9+ and CD4+CCR9− cells using flow cytometry. Cells were isolated from human colon or Ileum and were treated with PMA/ionomycin and Brefeldin A (a protein transport inhibitor) for 4 hours to stimulate cytokine production. CD4+ T cells were identified by gating based on single live cells that were CD45+, CD3+ and CD8−. It was found that CD4+ CCR9+ cells express higher levels of pro-inflammatory cytokines than CD4+CCR9− cells (FIG. 2A). The difference in levels between the CD4+CCR9− cells and CD4+CCR9+ cells was greatest for the expression of IL-17 (in the range of two-fold to six-fold increase), although the average difference was still around two to three-fold for both IL-4 and IFN-γ (FIG. 2B).

5.10 Example 3—Generation of Anti-CCR9 Antibodies

Anti-CCR9 antibodies were generated using hybridoma technology following immunization of CD1 mice with alternating human CCR9 and mouse CCR9 over expressing HEK cell lines. Three groups of mice were used. For Group 1, mice were immunised with alternating CHO and HEK cells over-expressing hCCR9; Group 2 mice were immunised with alternating HEK cells over-expressing hCCR9 and HEK cells over-expressing mCCR9; Group 3 mice were immunised with HEK cells over-expressing mCCR9. The recombinant cell lines were administered at 1e7 cells/100 μL diluted in PBS, emulsified with equal volumes of complete Freund's adjuvant, and injected into the mice at two sites, 100 μL per site. For the subsequent three injections, the cells were emulsified in Freund's incomplete adjuvant and injections performed as above. The final boost was carried out on day 24, by injecting 200 μL of cells in PBS intraperitoneally.

Tail vein bleeds were obtained from mice before immunisation, on day 13 after the first immunization, and on day 20 after second immunisation. The IgG titres to human CCR9, mouse CCR9 and the parental HEK and CHO cells were determined by serum ELISA. The animals with the highest antigen specific titres were taken forward for hybridoma generation.

5.10.1 Assessment of Mouse Immune Response to hCCR9 and mCCR9

The individual mouse serum IgG titres to hCCR9 and mCCR9 were determined by ELISA. The hCCR9 and mCCR9 HEK and CHO cell lines described above, along with parental HEK and CHO cells were coated on to 96 well Poly-D-Lysine microtitre plates at a 40,000 cells/well and cultured overnight at 37° C. in a $CO_2$ incubator. After overnight incubation, the supernatant was removed and the cells fixed for 5 min in 3.7% solution of formaldehyde/PBS at RT. All subsequent incubations were carried out at room temperature. After removal of the formaldehyde solution, the wells were then blocked by addition of 3% marvel/PBS blocking buffer. After 1 h, the blocking buffer was removed, the wells washed with PBS again and the serum samples added in a dilution series (50 μL per well starting from a 1:200 dilution). After incubating for 1 h, the wells were washed three times with PBS supplemented with 0.05% (v/v) Tween 20. A Europium-labelled anti-mouse IgG at 1:500 in Delfia assay buffer (Perkin Elmer) was then added to the wells at 50 μL per well. Following a further 1 h incubation and five washes as above, Enhancement solution (Perkin Elmer) was added to the wells at 50 ul per well, the plates were incubated at RT for 10 min on an orbital shaker. The plates were then read using a PerkinElmer EnVision 2103 multilabel plate reader.

The serum titration curves for hCCR9, mCCR9, as well as parental HEK and CHO cells were plotted and the respective area under the curves (AUC) calculated.

5.10.2 Monoclonal Mouse IgG Isolation

Four days after the final boost, lymph nodes were aseptically harvested, and cells were isolated by mechanical disruption and counted. These cells were mixed with SP2/0 myeloma cells and fused using an electrofusion apparatus. The resultant fusions were mixed with a methylcellulose-based semi-solid media and plated out into OmniTray plates. The semi-solid media comprised CloneMatrix and DMEM supplemented with 20% FCS, 10% BM Condimed H1, 1 mM sodium pyruvate and OPI media supplement, 2% hypoxanthine azaserine and FITC conjugated goat anti-mouse IgG. The cells in semi-solid media were cultured for 13 days at 37° C. in a 5% $CO_2$ incubator. During this incubation period, clonal colonies are formed from a single progenitor hybridoma cell. These colonies secrete IgG that is trapped in the vicinity of the colony by the FITC conjugated anti-IgG present in the semi-solid media. The resultant immune complex formation can be observed around the cell as a fluorescent 'halo' when visualised by ClonePix FL colony picker (Molecular Devices). These haloed colonies are then picked into 96 well microtitre plates.

After 3-5 days in culture, the supernatants of the picked colonies were harvested and screened for CCR9 binding.

5.10.3 DNA Sequencing and Purification of Mouse IgGs

Messenger RNA (mRNA) was extracted from hybridoma cells using magnetic oligo (dT) particles and reverse transcribed into cDNA. PCR amplification was performed using poly-C and constant region VH or VL primers specific to all mouse IgG subclasses.

5.10.4 Mouse IgG Purifications

Cells were propagated in 24 well plates and overgrown in serum free HL-1 medium supplemented with HyperZero and glutamine. After 10 days, the supernatants were transferred to 96 well master blocks and mouse IgGs of all subclasses (IgG1, IgG2a, IgG2b and IgG3) were purified from overgrown cell culture supernatants on ProPlus resin (Phynexus) using Perkin Elmer Minitrack. The captured mouse IgGs were eluted with 75 μL of 100 mM HEPES, 140 mM NaCl pH 3.0 then neutralised with an equal volume of 200 mM HEPES pH 8.0. The purified IgGs were quantified using an absorbance reading at 280 nm in UV-Star 384 well plate.

5.10.5 Reformatting of Mouse IgGs

Mouse hybridoma IgG clones were molecularly reformatted to generate constructs expressing mouse VH and VL domains and the relevant mouse IgG constant domains for each hybridoma essentially as described by Persic et al 1997 [7] with the following modifications. An OriP fragment was included in the expression vectors to facilitate use with CHO-transient cells and to allow episomal replication. The VH domain was cloned into the relevant vector containing the mouse heavy chain constant domains and regulatory elements to express whole IgG1 heavy chain in mammalian cells. Similarly, the VL domain was cloned into a vector for the expression of the appropriate mouse light chain (lambda or kappa) constant domains and regulatory elements to express whole IgG light chain in mammalian cells. To obtain IgGs, mammalian suspension CHO cells were transiently transfected with the heavy and light chain IgG vectors. IgGs were expressed and secreted into the medium. Harvests were filtered prior to purification, then IgG was purified using Protein A chromatography. Culture supernatants were loaded on a column of appropriate size of Ceramic Protein A (Pall 20078-036) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using Nap10 columns (GE Lifesciences 17-0854-02) and the concentration of IgG was determined spectrophotometrically using an extinction coefficient based on the amino acid sequence of the IgG [8]. The purified IgG were analysed for purity using SDS-PAGE. Purified IgGs were screened for binding to human CCR9 on HEK cells.

FIG. 3 shows the amino acid sequences of the variable heavy chain (FIG. 3A) and variable light chain (FIG. 3B) sequences for nine unique hits identified in this screen. cDNA for AB1020243, for example, was prepared from clone ZY10OI-A02 and the sequence for the VH and VL domains determined. FW=framework region. The locations of the CDRs are underlined as indicated by Kabat assignment (Kabat et al, Sequences of Immunological Interest, 5th Ed. Public Health Service, National Institutes of Health, Bethesda, Md. (1991)). The VH and VL sequences of humanized AB1020243 (AB1020243-fgl) are illustrated in FIG. 4, where they are aligned with the original chimeric sequences.

To further improve the potency and effectiveness of AB1020243, directed scanning mutagenesis of H & L CDRs was performed. CDRs were mutated by site-directed mutagenesis of mammalian expression vectors with low-redundancy biased nucleotide (NNC) codon mixtures, designed to maximize the abundance of alternative amino acids (aa) whilst eliminating undesirable amino acids (Met, Trp) from the library. 566 CDR variants were produced and CDR-optimised versions of humanised AB1020243 were generated. The screening library was expressed in CHO-cells from 24-well deep plates before protein A purification of variants. Following the identification of improved variants, intra and inter-CDR recombination was performed by site-directed mutagenesis to combine beneficial variants into the final lead antibody candidates as a-fuc huIgG1. The VH and VL sequences of CDR optimised antibodies AB243LO0331 and AB243LO0326 are illustrated in FIG. 4, where they are aligned with the parent sequences from AB1020243, and with the humanised form of AB1020243. The LCDR1 residues that have been modified are shown in bold, underlined text.

5.11 Example 4—Assessment of CCR9 Binding and Potency 5.11.1 Cell Binding

Binding of the antibodies to CCR9-expressing cells was assessed using HEK cells overexpressing human CCR9A, or using Molt4 cells. The Molt4 cell line is derived from human T cells and is known to express CCR9 [9]. Test antibodies were diluted to a concentration of 10 μg/mL in PBS supplemented with 1% Fetal Bovine Serum. Antibodies were titrated as single point using three-fold titrations over 8 points on a 96 well plate and cells were stained at 4° C. for 20 min. Cells were washed and stained with a secondary goat anti mouse or human IgG PE at 2.5 μg/ml in sterile PBS+1% FBS serum at 4 C for 20 minutes FIG. 5A shows that at least AB1020243, AB1020229, and AB1020011 bound to the Molt4 cells. Binding to Molt4 cells was compared with binding to Jurkat cells, which do not express human CCR9. As illustrated in FIG. 5B, binding to Molt4 cells was similar to that seen in FIG. 5A, whereas no significant binding to Jurkat cells was detected.

The antibody AB1020243 (hybridoma mIgG) was also tested for binding to different forms of CCR9. Briefly, test antibody was diluted to a concentration of 60 ug/mL in assay buffer containing Hanks Balanced Salt solution (Sigma HB264) plus 0.1% Bovine Serum Albumin (Sigma A9576). Antibody was titrated in duplicate using single fold titrations over 24 points on a 384 black clear bottomed, non-binding microplate (Corning® NBS™ 3655) so that the final volume of test antibody was 10 uL per well. The secondary detection antibody Alexa Fluor 647 labelled human IgG (H+L) (Jackson Immuno-Research; 209-665-082) was prepared according to the manufacturer's instructions and diluted 1:1000 in assay buffer as described above. The secondary detection antibody was dispensed to the assay plate containing test antibodies using a Multidrop dispenser (Thermo Scientific) in a volume of 10 uL per well.

Figure 6:
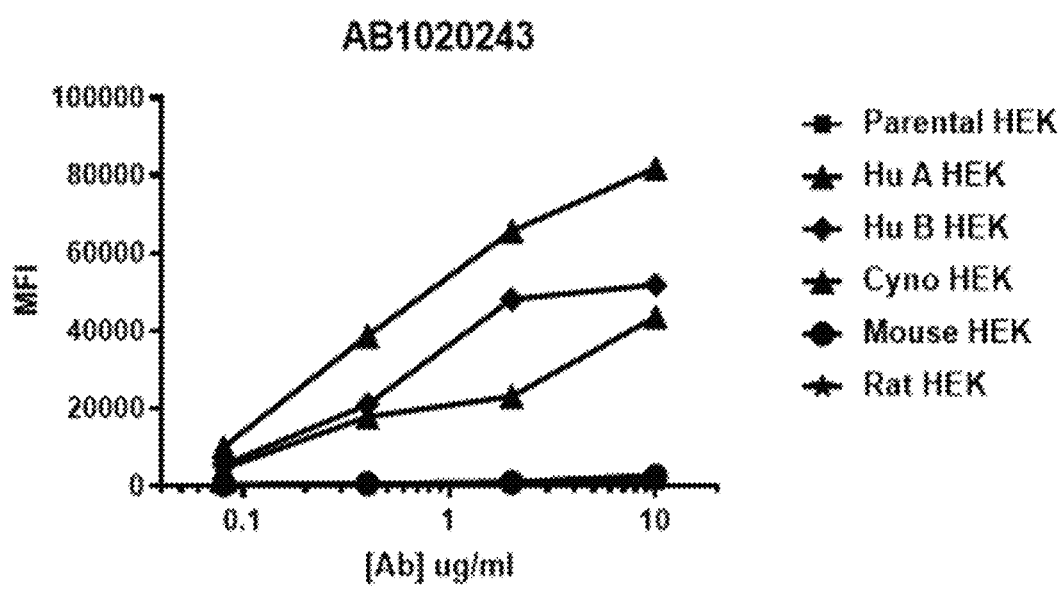

Transfected HEK CCR9 overexpressing cell lines or un-transfected parental control cells were suspended in assay buffer at a concentration of $1 \times 10^6$ cells per ml, and 10 uL of cells were dispensed to the assay plate containing test antibody and secondary antibody using a Multidrop dispenser (Thermo Scientific). Assay plates were incubated overnight at 4° C. and were read on a Mirrorball® (laser scanning fluorescence cytometer; TTP-Labtech) using excitation at 488 nm and emission using the FL4 channel (667-685 nm). Data was plotted in GraphPad Prism version 8.0.0 for Windows (GraphPad Software, San Diego, Calif. USA) and expressed as Log (mg/mL antibody) v's Fluorescence (FL4) counts. As illustrated in FIG. 6, it showed good binding of AB1020243 to both human forms of CCR9 (CCR9A and CCR9B) and to cynomolgus CCR9. It showed little or no binding to mouse or rat CCR9.

5.11.2 In Vitro ADCC Bioassay

The potency and effector function of the antibodies was assessed using an NK cell activation assay, as follows: All potency assays were run at an Effector (NK-92 MI CD16a NFAT cells) to Target (Molt4; HEK CCR9 over expressing cells or Jurkat cells) ratio of 5:1. The Effector NK-92 cell line does not naturally express the FcγRIIIa receptor (CD16). A modified form of NK-92 was used that overexpresses the high affinity (ha) CD16 V158 FcγRIIIa receptor, which has increased binding to Fc domains (Boissel et al Proceedings of the 107th Annual Meeting of the American Association for Cancer Research; 2016 Apr. 16-20; New Orleans, La. Philadelphia (Pa.): AACR; Cancer Res 2016; 76(14 Suppl): Abstract 2302). This receptor allows the NK cells to cross-link to the target cells via the antibody that is bound to the target cells. The NK-92 cells used also express a NFAT luciferase reporter, which can be used as a surrogate for effector function. Binding of the target-bound antibody to the NK cell induces activation of the NFAT transcription factor, which drives a luciferase reporter gene. The luminescence signal is proportional to the ADCC activity.

Both target and effector cells were prepared in assay media containing Advanced RPMI (Gibco™; 12633) with 10% Ultra Low IgG FBS (Gibco™; 16250-078). Target cells were resuspended at a concentration of $8 \times 10^5$ cells per mL and effector cells were re-suspended at a concentration of 8×10⁶ cells per mL. Test antibodies were diluted to a concentration of 60 μg/mL and duplicate 4-fold titrations were performed over 12 points on a 384 well polypropylene microplate (Greiner Bio-one International; 781280).

Target cells were dispensed into 384 well white clear bottom tissue culture treated plates (Corning®3560) using a Multidrop dispenser (Thermo Scientific) in a volume of 12.5 μL per well. Test antibodies (6.25 μL per well) were then added to target cell containing plates using a Bravo Automated Liquid Handling Platform (Agilent). Target cells and antibodies were pre-incubated for 30 minutes at 37° C. in a $O_2/CO_2$ incubator. Effector cells were then added using a Multidrop dispenser (Thermo Scientific) in a volume of 6.25 μL per well. Assay plates containing target cells, effector cells and antibodies were incubated for a further 5 hours at 37° C. in a $O_2/CO_2$ incubator.

At the end of the incubation period the Luciferase detection reagent was prepared according to the manufacturer's instructions (Steady-Glo® Luciferase Assay System; Promega E2520), and 25 μL was dispensed to each well using manual pipetting. Assay plates were covered in foil and allowed to undergo lysis for 20 minutes at room temperature on plate shaker. Assay plates were read on an EnVision® 2105 multimode plate reader (Perkin Elmer) using the ultra-sensitive luminescence mode. Data was analysed in GraphPad Prism version 8.0.0 for Windows (GraphPad Software, San Diego, Calif. USA) using a four-parameter log (agonist) vs response logistic equation. Data was expressed as Log (Molar) antibody concentration v's response (Counts per second).

FIG. 7 shows the NK cell activation by (afucosylated) antibodies when bound to the MOLT4/HEK cells. The afucosylated forms of the antibodies were produced from a dual expression cassette, whereby the heavy chain IgG expression is co-expressed with the RMD enzyme to produce afucosylated protein in CHO cells. Potency of the AB1020243 afuc antibody when bound to the HEK cells expressing human CCR9A was measured as 0.5 nM. Potency of the humanised AB1020243 afuc antibody when bound to the Molt4 cells was measured as 0.8 nM.

5.11.3 PBMC Killing Assay

The antibodies were serial titrated (10-fold) with a start concentration of 10 μg/mL over 8 points. Antibodies were added to 1×10⁶ human peripheral blood mononuclear cells (PBMCs) in u-bottom 96 well plate and incubated overnight. The following day, the percentage of remaining CCR9-expressing CD4 T cells was measured by flow cytometry using a non-competing CCR9 antibody. The VH/VL and CDR sequences of the non-competing antibody are shown in Table 5 and Table 6. As illustrated in FIG. 8, antibodies AB1020243, AB1020229 and AB1020011 all showed killing of CCR9+ PBMC. The EC50 (n=4) for AB1020243 afuc was measured as 2.6 nM.

TABLE 5

Amino acid sequences of the VH and VL regions of the non-competing CCR9 antibody.

| Binding molecule | | VH/VL amino acid sequence | SEQ ID |
|---|---|---|---|
| AB1020105 | VH | EVKLEESGGGLVQPGGSMKLSCVASGFTFNKYWMNWVRQSPEKGLEWVVQIKL KSDNYATHYAESVKGRFAISRDDSKSSVYLQANNLRAEDTGIYYCTLRPFTYW GQGTLVTVSA | 72 |
| | VL | DVLMTQNPLSLPVSLGDQASISCRSSQSIIHSNGNTYLEWYLQKPGQSPKLLI YKVSNRFSGVPDRFSGSGSGTDFTLKISRVEAEDLGVYYCFQGSHVPWTFGGG TKLEIK | 73 |

TABLE 6

Amino acid sequences of the CDRs of the non-competing CCR9 antibody.

| Binding molecule | CDR | Amino acid sequence | SEQ ID | CDR | Amino acid sequence | SEQ ID |
|---|---|---|---|---|---|---|
| AB1020105 | HCDR1 | KYWMN | 44 | LCDR1 | RSSQSIIHSNGNTYLE | 47 |
| | HCDR2 | QIKLKSDNYATHYAESVKG | 45 | LCDR2 | KVSNRFS | 5 |
| | HCDR3 | RPFTY | 46 | LCDR3 | FQGSHVPWT | 48 |

TABLE 7

Amino acid sequences of heavy and light chain constant region

| Constant region | Amino acid sequence | SEQ ID |
|---|---|---|
| Heavy chain | ASTKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKV | 78 |

TABLE 7-continued

Amino acid sequences of heavy and light chain constant region

| Constant region | Amino acid sequence | SEQ ID |
|---|---|---|
| | SNKALPAPIEKTISKAKGQPREPQVYTLPPSREEMTKNQVSLTCLVKGFYPSDIAVEWESNG QPENNYKTTPPVLDSDGSFFLYSKLTVDKSRWQQGNVFSCS VMHEALHNHYTQKSLSLSPGK | |
| Light chain | RTVAAPSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFN RGEC | 79 |

5.12 Example 5—Properties of Humanised AB1020243

Humanised AB1020243 was produced as in Example 3. In all experiments described hereforth the humanised AB1020243 was in an afucosylated form produced from a dual expression cassette, whereby the heavy chain IgG expression is co-expressed with GDP-6-deoxy-D-lyxo-4-hexulose reductase (RMD) to produce afucosylated protein in CHO cells.

5.12.1 CCR9 Cross-Reactivity of Humanised AB1020243

The binding of the parent AB1020243 antibody (chimeric) was compared with that of the humanised version based on the methods described in Example 4.

As illustrated in FIG. 9, the humanised antibody ("human") retained similar binding to the parent AB1020243 ("chimeric") against cynomolgus CCR9 and HEK cells expressing human CCR9B (FIG. 9A and FIG. 9B). No significant binding was seen against the parent HEK JI cell line, which does not express CCR9 (FIG. 9G). Even at higher concentrations, humanised AB1020243 showed no significant off target binding to CXCR1 (FIG. 9C), CXCR2 (FIG. 9D), CCR5 (FIG. 9E) or CCR8 (FIG. 9F).

5.12.2 Humanised AB1020243 Retains High Potency

Humanisation of AB1020243 surprisingly led to no significant change in potency in the NK cell activation assay (FIG. 10). The chimeric and humanised forms of AB1020243 afuc produced the same degree of activation of the NK-92 cell line described above using MOLT4 cells. This is contrasted with a benchmark afucosylated mouse anti-CCR9 IgG1 antibody (3C3, ATCC HB-12653) for which a large reduction in potency was observed following humanisation. Similarly, humanisation did not alter the potency of AB1020243 afuc bound to HEK cells overexpressing cynomolgus CCR9A.

It was also found that kinetic properties of the AB1020243 afuc antibody were not significantly changed by humanisation. CCR9+ live cell measurements were made using fluorescently labelled antibodies, using Ligand Tracer technology. Briefly, on-cell affinities were measured on a LigandTracer instrument (Ridgeview Instruments) using a 633 nm fluorescence detector, at room temperature (~22° C.). IgGs in human IgG1 format were specifically labelled with DyLight 650 Maleimide fluorophore on an engineered cycteine residue on the CH2 region of the IgG. The labelled IgG were added to circular Nunclon D plate, with pre-adhered discrete spots of CHO K1 parent (control) and CCR9-expressing CHO K1 cells. IgG binding and dissociation fluorescence profiles were measured on the instrument and then analysed with a Bivalent (1:2) type fit model within TraceDrawer software (Ridgeview Instruments). The off-rate ($k_d$) of AB1020243 afuc was measured as $3.85 \times 10^{-5}$ $s^{-1}$, and this remained similar after humanisation, being measured as $4.3 \times 10^{-5}$ $s^{-1}$. This is consistent with there being no potency reduction observed upon humanisation (FIG. 10B).

5.12.3 Ability to Compete with CCL25

Humanised AB1020243 was tested for its ability to compete with CCL25 in an HTRF IP-One Gq assay (Cis-Bio; 62IPAPEB). The IP-One assay is a competitive immunoassay that uses terbium cryptate-labelled anti-IP1 Mab and d2-labeled IP1. IP1 is a downstream metabolite of the IP cascade and accumulates in cells following Gq receptor activation and is stable in the presence of LiCl. LiCl is added to the cell stimulation buffer, causing the accumulation of IP1 upon receptor activation.

Test antibodies were buffer exchanged into IP-one buffer (Krebs Ringer solution+LiCl) and were serially diluted from neat in IP-one buffer using a one plus one dilution series over 16 points (in triplicate) on a 384 well polypropylene microplate (Greiner Bio-one International; 781280) and 3.5 mL of each antibody was added to white 384 shallow plates (Costar; 4513) using a Bravo Automated Liquid Handling Platform (Agilent). MOLT 4 cells were harvested and re-suspended in IP-One assay buffer to $5.4 \times 10^6$ cells/mL and 7.5 μL of cells were dispensed to the antibody containing plates using a Multidrop dispenser (Thermo Scientific) so that the final cell concentration was 40,000 cells/well. Antibodies were pre-incubated with cells for 30 minutes. Recombinant Human CCL25/TECK Protein (R&D systems; 9046-TK) was reconstituted to 200 nM according to the manufactures instructions and 3.5 uL was dispensed to the antibody and cells containing plates using a Multidrop dispenser (Thermo Scientific), so that the final assay concentration was 50 nM. Assay plates were incubated at 37 C for 90 minutes, before being processed according to the IP-One HTRF protocol using the reagents provided with the kit. FIG. 11 shows that humanised AB1020243 and the CDR optimised antibodies 234LO0331 and 243LO0326 retain similar abilities to compete with CCL25 as the parent chimeric AB1020243 antibody. The antibodies of the present invention therefore contrast with previous described mouse CCR9 antibodies 92R and 91 R that do not, for example, inhibit CCL25 induced migration of CCR9+ MOLT-4 cells and only partial compete with CCL25 for binding to MOLT-4 cells [4].

5.13 Example 6—Properties of CDR Optimised Antibodies

As set out in Example 3, CDR optimised forms of humanised AB1020243 were produced. In all experiments described herein the CDR optimised antibodies were in an afucosylated form. The CDR optimized antibodies were formatted to reduce the risk of Asn deamidation in LCDR1.

5.13.1 CCR9 Binding

CDR-optimised AB1020243 was tested for its ability to bind to different forms of CCR9 and to different cell types, based on the methods described in Example 4. As illustrated in FIG. 12, 243LO0326 and the parent antibody AB1020243 showed similar binding to both human isotypes CCR9A and CCR9B, and to cynomolgus CCR9A. Both 243LO0326 and 243LO0331 showed no significant binding to either mouse or rat CCR9, even at high concentrations (data not shown). 243LO0326 and the parent antibody AB1020243 also failed to show any off-target receptor binding to CCR5, CCR8, CXCR1 or CXCR2.

5.13.2 Affinity

As shown in FIG. 13A, 243LO0326 remained bound to the membrane over an extended period of time, with the majority of the antibody remaining on the cell surface after 5 hours at 37° C. In comparison, the amount of the parental antibody AB1020243 bound to the cell surface dropped off significantly in the first hour. Affinity ($K_D$) was measured using Ligand Tracer as 0.09 nM for 243LO0326 and 3.4 nM for AB1020243. Briefly, on-cell affinities were measured on a LigandTracer instrument (Ridgeview Instruments) using a 633 nm fluorescence detector, at room temperature (~22° C.). IgGs in human IgG1 format were specifically labelled with DyLight 650 Maleimide fluorophore on an engineered cyteine residue on the CH2 region of the IgG. The labelled IgG were added to circular Nunclon D plate, with pre-adhered discrete spots of CHO K1 parent (control) and CCR9-expressing CHO K1 cells. IgG binding and dissociation fluorescence profiles were measured on the instrument and then analysed with a Bivalent (1:2) type fit model within TraceDrawer software (Ridgeview Instruments).

As shown in FIG. 13B, only a slight reduction in CCR9 receptor level was seen on the membrane with antibody treatment. For comparison, CCL25 treatment induced a major decrease in CCR9 receptor on the membrane. It was further shown that the anti-CCR9 antibodies were able to prevent CCL25 induced internalisation (FIG. 19).

5.13.3 Potency

CDR-optimised AB1020243 was tested for its ability to induce NK cell activation and PBMC killing as described in Example 4. FIG. 14A shows the effects of antibodies in the NK cell activation assay. It was found that 243LO0326 was more potent than the parent antibody AB1020243. FIG. 14B shows the killing of PBMC by 243LO0326 and by the parental antibody AB1020243. 243LO0326 showed an improved potency, with an EC50 of 4 pM, compared to an EC50 of 200 pM for AB1020243. FIG. 14C shows that 243LO0346 has a similar ability to induce killing of both human and cynomolgus CD4+CCR9+ PBMC, with an EC50 measured at 4-5 pM using human PBMC and an EC50 of 30 pM using cynomolgus PBMC.

5.13.4 Afucosylation

Afucosylation of the anti-CCR9 antibodies enhances cell killing, as shown in the ADCC NK cell activation assay (FIG. 15A). The impact of the level of fucosylation on potency of the antibody (243LO0326) was assessed in an fucosylation spiking study using the in vitro ADCC bioassay (see section 5.11.2). ADCC potency of the antibody was retained compared to 100% afucosylated molecules for up to about 10% fucosylation. Acceptable potency was retained for fucosylation of up to 50% (FIG. 15B).

TABLE 8

ADCC activity of fucosylated vs. afucosylated species - spiking study

| Sample[1] | % RP (95% CI)[2] |
|---|---|
| Tox (SP21-051) | 102% (83-125%) |
| ~5% fuc | 103% (88-121%) |
| ~10% fuc | 102% (86-121%) |
| ~20% fuc | 75% (62-91%) |
| ~50% fuc | 50% (42-59%) |
| ~100% fuc | NR[3] |

[1]Approximate fucosylation levels, Tox fuc levels = 0.8%
[2]% RP (relative potency) is a combined value from two independent assay runs
[3]NR = non-reportable - sample does not meet suitability criteria, due to severe potency loss

5.14 Example 7—In Vitro and In Vivo Effects

5.14.1 Antibody Depletion of CCR9+ Cells in Cynomolgus Monkeys

Monkeys were injected intravenously with a single dose of isotype control antibody and 10 mg/kg of 243LO0326. The percentage of CCR9+ memory CD4+ T cells was assessed in the blood at various time points. FIG. 16A shows that there was a decrease in CCR9+ cells present in the blood at day 15 with 10 mg/kg 243LO0326 completely abolishing CCR9+ cells at this timepoint. Particularly, at high and low doses (10 mg/kg), 243LO0326 depleted CCR9+ T cells in the peripheral blood (FIG. 16B), illeum (FIG. 16C) and mucosa (FIG. 16D). The depletion of CCR9+ T cells was tissue and cell specific (FIG. 17). 243LO0326 selectively depleted CCR9+ gut lymphocytes with relative sparing of extra-intestinal populations, having no impact on thymus T cells.

5.14.2 Gut Explant Model 6 mm punch biopsies of the gut mucosal layer were taken from healthy human subjects and human subjects with inflammatory bowel disease as described in Vadstrup et al. [10]. Explant tissue was cultured in the presence or absence of 243LO0326 for 12-84 hours. The percentage of CCR9+ cells was assessed along with key mediators of inflammation: IL-6, GM-CSF and IL-22. FIG. 18 shows that treatment with the antibody depleted CCR9+ CD4+ cells (FIG. 18A) and reduced inflammatory mediators (FIG. 18B to FIG. 18D) in each of the explants tested. Explant tissue from one of the healthy subjects also showed high levels of IL-6, GM-CSF and IL-22 which were decreased upon anti-CCR9 treatment.

5.15 Example 7—Anti-CCR9 Antibodies Block CCL25 Induced CCR9 Internalisation

IHC data surprisingly suggest that there is quantitatively lower expression of CCR9 in inflamed Crohn's ileum. Ex vivo, CCR9 internalises following activation by CCL25, which is expressed at higher levels in inflamed Crohn's ileum. This suggests that in the inflamed gut, CCR9 on pathogenic T cells is internalised following activation by CCL25. Cells that express CCR9 in Crohn's ileum nonetheless show pro-inflammatory and resident memory phenotypes.

In an assay to detect internalisation of CCR9, the CDR optimized afucosylated antibody 243LO0326 was able to prevent CCL25 induced internalisation at a concentration of 2 nM (FIG. 19). CCL25 induced internalisation was assessed by FACS. Advantageously, blocking CCL25-induced internalisation prevents receptor recycling. The antibodies of the invention thus advantageously induce ADCC, block CCL25 ligation of the CRR9 receptor, and prevent CCL25 induced CCR9 receptor recycling on CCR9 expressing T cells.

5.16 Conclusion

Together, these data show that anti-CCR9 treatment is a viable treatment option for patients with IBD. CRR9+ T cells expressing proinflammatory cytokines are expressed in the gut and blood of patients with inflammatory bowel disease (FIG. 1 and FIG. 2). The anti-CCR9 antibodies described above bind human CCR9 on CCR9 expressing T cells (FIG. 5 and FIG. 6). Afucosylated versions of these antibodies activate NK cells to promote ADCC (FIG. 7 and FIG. 15), leading to targeted cell killing (FIG. 8). Humanisation of one of the antibody clones surprisingly did not reduce the affinity of the antibody for human CCR9 compared to the chimeric parent antibody (FIG. 9), maintained the ability to activate NK cells (FIG. 10A), and retained the ability to compete with CCL25 (FIG. 11).

Further CDR optimization of one of the humanised antibodies was performed. These CDR optimised, afucosylated antibodies (243L00326 and 243L00331) bound membrane bound CCR9 for an extended period of time compared to the parent antibody and had an affinity ($K_D$) of 0.09 to 3.4 nM (FIG. 13). The CDR optimized antibodies were further able to induce NK cell activation and PBMC killing. 243L00326 was more potent than AB1020243 (FIG. 14). 243L00326 is further able to inhibit CCL25 induced CCR9 internalisation (FIG. 19). 243L00326 treatment also decreases CCR9 T cells in the blood (FIG. 16). 243L00326 treatment of gut explant tissue from IBD patients depletes CCR9+CD4+ cells (FIG. 16A) and reduces inflammatory mediators (FIG. 16B to FIG. 16D). 243L00326 is thus highly potent, and specific to CCR9. Cell depletion occurs via ADCC; however, in the absence of ADCC effector cells, such as NK cells, 243L00326 also blocks binding between CCR9 and its ligand CCL25.

Given that the CCR9 antibodies disclosed herein are able to bind both isoforms of hCCR9, CCR9A and CCRB, and compete with CCL25 for binding to CCR9, the epitope is expected to be located within the extracellular N-terminus of CCR9B, i.e. amino acid positions 1-36 of CCR9B: MAD-DYGSESTSSMEDYVNFNFTDFYCEKNNVRQFAS (SEQ ID NO: 80), corresponding to amino acid positions 13-48 of CCR9A (Table 9, Table 10, FIG. 20).

TABLE 9

Antibody epitope sequence

| | Sequence | SEQ ID |
|---|---|---|
| N-terminus sequence overlap of CCR9A and CCR9B | MADDYGSESTSSMEDYVNFNFTDFYCE KNNVRQFAS | 80 |

TABLE 10

Sequence of hCCR9 isoforms

| Isoform | Sequence | SEQ ID |
|---|---|---|
| CCR9A | MTPTDFTSPIPNMADDYGSESTSSMEDYVNFNFTDFYCEKNNVRQFASHFLPPLYWLVFI VGALGNSLVILVYWYCTRVKTMTDMFLLNLAIADLLFLVTLPFWAIAAADQWKFQTFMCK VVNSMYKMNFYSCVLLIMCISVDRYIAIAQAMRAHTWREKRLLYSKMVCFTIWVLAAALC IPEILYSQIKEESGIAICTMVYPSDESTKLKSAVLTLKVILGFFLPFVVMACCYTIIIHT LIQAKKSSKHKALKVTITVLTVFVLSQFPYNCILLVQTIDAYAMFISNCAVSTNIDICFQ VTQTIAFFHSCLNPVLYVFVGERFRRDLVKTLKNLGCISQAQWVSFTRREGSLKLSSMLL ETTSGALSL | 81 |
| CCR9B | *MADDYGSESTSSMEDYV NFNFTDFYCEKNNVRQFAS*HFLPPLYWLVFIVGALGNS LVILVYWYCTRVKTMTDMFLLNLAIADLLFLVTLPFWAIAAADQWKFQTFMCKVVNSMYKM NFYS CVLLIMCISVDRYIAIAQAMRAHTWREKRLLYSKMVCFTIWVLAAALCIPEILYSQIKEE SGIAICTMVYPSDESTKLKSAVLTLKVILGFFLPFVVMACCYTIIIHTLIQAKKSSKHKA LKVTITVLTVFVLSQFPYNCILLVQTIDAYAMFISNCAVSTNIDICFQVTQTIAFFHSCL NPVLYVFVGERFRRDLVKTLKNLGCISQAQWVSFTRREGSLKLSSMLLETTSGALSL | 82 |

The CCR9 targeting antibodies disclosed herein are able to both block binding of CCL25 to CCR9 and to deplete CCR9+ T cells. In inflammatory autoimmune disease of the gut, the antibodies disclosed herein are expected to both deplete CCR9+ pathogenic T cells in blood and gut tissue and to block binding of CCL25 to CCR9 where pathogenic T cells are not fully depleted. This dual mechanism of action is expected to provide a sustained treatment effect. Specific depletion of CCR9+ gut tropic effector memory T cells will induce and sustain durable remission and deliver disease modification.

REFERENCES

[1] M. F. Neurath, Nat Rev Immunol 14, 329 (2014).

[2] M. Gajendran et al., Dis Mon 64, 20 (2018).

[3] J. Torres et al., J Crohns Colitis 14, 4 (2020).

[4] B. Somovilla-Crespo et al., Frontiers in Immunology 9, (2018).

[5] R. L. Shields et al., J Biol Chem 277, 26733 (2002).

[6] P. Umana et al., Nat Biotechnol 17, 176 (1999).

[7] L. Persic et al., Gene 187, 9 (1997).

[8] C. N. Pace et al., Protein Sci 4, 2411 (1995).

[9] J. Minowada, T. Ohnuma, and G. E. Moore, JNCI: Journal of the National Cancer Institute 49, 891 (1972).

[10] K. Vadstrup et al., PLOS ONE 11, e0155335 (2016).

The invention claimed is:

1. A binding molecule that binds to C-C motif chemokine receptor 9 (CCR9) and comprises a heavy chain variable (VH) region having a set of CDRs HCDR1, HCDR2 and HCDR3 and a light chain variable (VL) region having a set of CDRs LCDR1, LCDR2 and LCDR3, wherein
   (a) the VH region amino acid sequence comprises HCDRI of SEQ ID NO: 1, HCDR2 of SEQ ID NO: 2 and HCDR3 of SEQ ID NO: 3, and wherein the VL region amino acid sequence comprises LCDRI of SEQ ID NO: 4, LCDR2 of SEQ ID NO: 5 and LCDR3 of SEQ ID NO: 6;
   (b) the VH region amino acid sequence comprises HCDR1 of SEQ ID NO: 7, HCDR2 of SEQ ID NO: 8 and HCDR3 of SEQ ID NO: 9, and wherein the VL region amino acid sequence comprises LCDRI of SEQ ID NO: 10, LCDR2 of SEQ ID NO: 11 and LCDR3 of SEQ ID NO: 12; or
   (c) the VH region amino acid sequence comprises HCDRI of SEQ ID NO: 13, HCDR2 of SEQ ID NO: 14 and HCDR3 of SEQ ID NO: 15, and wherein the VL region amino acid sequence comprises LCDRI of SEQ ID NO: 16, LCDR2 of SEQ ID NO: 17 and LCDR3 of SEQ ID NO: 18.

2. The binding molecule of claim 1, wherein:
   (i) the VH region amino acid sequence comprises SEQ ID NO: 51 and; the VL region amino acid sequence comprises SEQ ID NO: 52;
   (ii) the VH region amino acid sequence comprises SEQ ID NO: 51, and; the VL region amino acid sequence comprises SEQ ID NO: 53;
   (iii) the VH region amino acid sequence comprises SEQ ID NO: 51 and; the VL region amino acid sequence comprises SEQ ID NO: 54;
   (iv) the VH region amino acid sequence comprises SEQ ID NO: 51; and the VL region amino acid sequence comprises SEQ ID NO: 55; or
   (v) the VH region amino acid sequence comprises SEQ ID NO: 56, and; the VL region amino acid sequence comprises SEQ ID NO: 57.

3. The binding molecule of claim 1, wherein:
   (i) the VH region amino acid sequence comprises SEQ ID NO: 58; and wherein the VL region amino acid sequence comprises SEQ ID NO: 59; or
   (ii) the VH region amino acid sequence comprises SEQ ID NO: 60; and the VL region amino acid sequence comprises SEQ ID NO: 61.

4. The binding molecule of claim 1, wherein the binding molecule is an anti-CCR9 antibody, or an antigen-binding fragment thereof.

5. The binding molecule of claim 1, which is:
   (a) an IgG immunoglobulin or a fragment thereof; or
   (b) an IgG1 immunoglobulin or a fragment thereof.

6. The binding molecule of claim 1, wherein said binding molecule comprises an immunoglobulin Fc domain, or a fragment thereof that retains the ability to bind to one or more Fc receptors.

7. The binding molecule of claim 6, wherein the immunoglobulin Fc domain or fragment:
   (a) is an IgG Fc domain or fragment thereof;
   (b) is a human IgG Fc domain or fragment thereof;
   (c) is a human IgG1 Fc domain or fragment thereof;

(d) is modified compared to the corresponding wild-type Fc domain, wherein said modification leads to an increased affinity for one or more Fcγ receptors;
(e) is modified compared to the corresponding wild-type Fc domain, wherein said modification leads to an enhanced antibody dependent cell-mediated cytotoxicity response; and/or
(f) comprises an afucosylated N-linked glycan at amino acid position 297.

8. The binding molecule of claim 1, wherein the binding molecule is:
(a) afucosylated;
(b) afucosylated at amino acid position 297; or
(c) present in a composition comprising multiple copies of said binding molecule, wherein at least 50%, 75%, 80%, 90%, 95%, 98%, 99% or 100% of the copies of the binding molecule in the composition are afucosylated.

9. The binding molecule of claim 1, wherein the binding molecule:
(a) binds to human CCR9;
(b) binds to human CCR9A and human CCR9B;
(c) binds to cynomolgus CCR9; and/or
(e) does not bind to CCR5, CCR8, CXCR1 or CXCR2.

10. The binding molecule of claim 1 wherein the binding molecule:
(a) is capable of mediating antibody dependent cell-mediated cytotoxicity against a CCR9-expressing cell to which it binds;
(b) is capable of mediating antibody dependent cell-mediated cytotoxicity against a CCR9-expressing lymphocyte to which it binds;
(c) can be bound by an FcγR;
(d) can be bound by FcγRIIIa;
(e) is capable of cross-linking an immune effector cell to a CCR9-expressing cell;
(f) is capable of cross-linking an immune effector cell to a CCR9-expressing cell and activating antibody dependent cell-mediated cytotoxicity by the effector cell;
(g) is capable of inhibiting CCL25 induced CCR9 receptor internalisation;
(h) is capable of inhibiting CCL25 mediated migration of CCR9 expressing T cells to the gut, (i) is capable of cross-linking an immune effector cell to a CCR9-expressing cell and activating antibody dependent cell-mediated cytotoxicity by the effector cell, thereby causing lysis of the CCR9-expressing cell; and/or (j) is capable of depleting CCR9-expressing cells in a population of cells comprising CCR9-expressing cells and immune effector cells.

11. The binding molecule of claim 1, wherein the binding molecule is capable of binding to human CCR9 with an affinity (KD) of about 0.1 nM.

12. An isolated polynucleotide encoding the binding molecule of claim 1.

13. The binding molecule of claim 4, wherein the anti-CCR9 antibody, or antigen-binding fragment thereof is humanised or chimeric.

* * * * *